United States Patent
Druzgala et al.

(10) Patent No.: US 7,022,722 B2
(45) Date of Patent: *Apr. 4, 2006

(54) MATERIALS AND METHODS FOR THE TREATMENT OF DIABETES, HYPERLIPIDEMIA, HYPERCHOLESTEROLEMIA, AND ATHEROSCLEROSIS

(75) Inventors: Pascal Druzgala, Santa Rosa, CA (US); Peter G. Milner, Los Altos Hills, CA (US); Jurg R. Pfister, Los Altos, CA (US)

(73) Assignee: ARYx Therapeutics, Inc., Fremont, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 10/759,617

(22) Filed: Jan. 16, 2004

(65) Prior Publication Data

US 2005/0075379 A1 Apr. 7, 2005

Related U.S. Application Data

(62) Division of application No. 09/841,351, filed on Apr. 24, 2001, now Pat. No. 6,680,387.

(60) Provisional application No. 60/281,982, filed on Apr. 6, 2001, provisional application No. 60/199,146, filed on Apr. 24, 2000.

(51) Int. Cl.
*A61K 31/426* (2006.01)
*A61K 31/427* (2006.01)

(52) U.S. Cl. .................. 514/369; 514/824; 514/866

(58) Field of Classification Search ................ 514/369
See application file for complete search history.

(56) References Cited

U.S. PATENT DOCUMENTS

| | | | |
|---|---|---|---|
| 4,287,200 A | 9/1981 | Kawamatsu et al. |
| 4,340,605 A | 7/1982 | Kawamatsu et al. |
| 4,376,777 A | 3/1983 | Kawamatsu et al. |
| 4,438,141 A | 3/1984 | Kawamatsu et al. |
| 4,444,779 A | 4/1984 | Kawamatsu et al. |
| 4,461,902 A | 7/1984 | Kawamatsu et al. |
| 4,572,912 A | 2/1986 | Yoshioka et al. |
| 4,687,777 A | 8/1987 | Meguro et al. |
| 4,703,052 A | 10/1987 | Eggler et al. |
| 4,725,610 A | 2/1988 | Meguro et al. |
| 4,873,255 A | 10/1989 | Yoshioka et al. |
| 4,897,393 A | 1/1990 | Iijima et al. |
| 4,897,405 A | 1/1990 | Alessi et al. |
| 4,918,091 A | 4/1990 | Cantello et al. |
| 4,948,900 A | 8/1990 | Iijima et al. |
| 5,002,953 A | 3/1991 | Hindley |
| 5,061,717 A | 10/1991 | Clark et al. |
| 5,120,754 A | 6/1992 | Clark et al. |
| 5,132,317 A | 7/1992 | Cantello et al. |
| 5,194,443 A | 3/1993 | Hindley |
| 5,223,522 A | 6/1993 | Clark et al. |
| 5,232,925 A | 8/1993 | Hindley |
| 5,260,445 A | 11/1993 | Hindley |
| 5,480,896 A | 1/1996 | Malamas et al. |
| 5,677,330 A | 10/1997 | Abraham et al. |
| 5,955,616 A | 9/1999 | Ohtani et al. |
| 6,037,359 A | 3/2000 | Shinkai |
| 6,121,288 A | 9/2000 | Matsui et al. |
| 2002/0045620 A1 | 4/2002 | Druzgala et al. |
| 2003/0027798 A1 | 2/2003 | Druzgala et al. |
| 2003/0064972 A1 | 4/2003 | Druzgala et al. |

FOREIGN PATENT DOCUMENTS

| | | |
|---|---|---|
| EP | 0 306 228 A1 | 3/1989 |
| EP | 0 419 035 A1 | 3/1991 |
| EP | 0 528 734 A1 | 2/1993 |
| EP | 0 549 365 A1 | 6/1993 |
| EP | 0 603 419 A1 | 6/1994 |
| EP | 0 684 242 A1 | 11/1995 |
| EP | 0 801 063 A1 | 10/1997 |
| EP | 0 848 004 A1 | 6/1998 |
| EP | 0 919 232 A1 | 6/1999 |
| EP | 0 930 299 A1 | 7/1999 |
| EP | 0 953 355 A1 | 11/1999 |
| EP | 0 992 503 A1 | 4/2000 |
| EP | 1 048 659 A1 | 11/2000 |
| ES | 2 154 551 A1 | 4/2001 |
| WO | WO 89/08651 | 9/1989 |
| WO | WO 91/07107 | 5/1991 |
| WO | WO 92/02520 | 2/1992 |
| WO | WO 93/21166 A1 | 10/1993 |
| WO | WO 97 32863 A1 | 9/1997 |

(Continued)

OTHER PUBLICATIONS

Database Caplus 'Online! Chemical Abstracts Service,' Columbus, Ohio, USA; Database Accession No. 127:248106, XP002222346, Torii Pharmaceutical Co., Ltd., Japan, 1997.

(Continued)

*Primary Examiner*—Barbara P. Badio
(74) *Attorney, Agent, or Firm*—McDonnell Boehnen Hulbert & Berghoff LLP

(57) ABSTRACT

The subject invention provides pharmaceutical compounds useful in the treatment of Type II diabetes. These compounds are advantageous because they are readily metabolized by the metabolic drug detoxification systems. Particularly, thiazolidinedione analogs that have been designed to include esters within the structure of the compounds are provided. This invention is also drawn to methods of treating disorders, such as diabetes, comprising the administration of therapeutically effective compositions comprising compounds that have been designed to be metabolized by serum or intracellular hydrolases and esterases. Pharmaceutical compositions of the ester-containing thiazolidinedione analogs are also taught.

260 Claims, 18 Drawing Sheets

FOREIGN PATENT DOCUMENTS

| | | |
|---|---|---|
| WO | WO 98/45291 A1 | 10/1998 |
| WO | WO 00/18759 A1 | 4/2000 |
| WO | WO 01/00566 | 1/2001 |
| WO | WO 01 02377 A1 | 1/2001 |
| WO | WO 01/16122 A1 | 3/2001 |
| WO | WO 01/16132 A1 | 3/2001 |
| WO | WO 01/81328 A2 | 11/2001 |
| WO | WO 02/24689 A1 | 3/2002 |
| WO | WO 02/44127 A1 | 6/2002 |

OTHER PUBLICATIONS

Database Chemcats, AsInEx Compound Collection, Moscow, Russia; Accession No. 2001:694380, May 10, 2001; XP002222347.

Database Chemcats, Pharma Library Collection, Nanosyn Combinational Synthesis, Inc., Mountain View, CA, USA; Accession No. 2001:54111, May 14, 2001; XP002222348.

Database Chemcats, Ambinter Exploratory Library, Paris, France; Accession No. 2001:1116502, Jan. 21, 2002; XP002222349.

Database Crossfire Beilstein; Beilstein Registry No.: 6526484; Beilstein Institut zur Foerderung der Chemischen Wissenschaften; XP-002230540; Frankfurt am Main, DE. 1994.

Database Caplus 'Online! Chemical Abstracts Service,' Columbus, OH, USA; Database accession No. 128:13261, XP002181181 RN 199167-77-6 and 199167-79-8 and JP 09301963 A (Kyorin Pharmaceutical Co., Ltd.) Nov. 25, 1997.

Database Caplus 'Online! Chemical Abstracts Service,' Columbus, OH, USA; Database acession No. 127:161819, XP002181182, RN 193544-82-0 and JP 09165371 A (Sankyo Co., Ltd.), Jun. 24, 1997.

Cantello, B., et al., "[[ω-(Heterocyclylamino) alkoxy] benzyl]-2,4-thiazolinediones as Potent Antihyperglycemic Agents", *J. Med. Chem.* (1994), 37:3977-3985; XP-001094112; American Chemical Society.

Chen, L., et al., "Focused Library Approach for Identification of N-Acylphenylalanines as VCAM/VLA-4 Antagonists", *Bioorg. Med. Chem. Lett.* (2002), 12:1679-1682; XP-002230539; Elsevier Science Ltd.

Haigh, D., et al., "Non-thiazolidinedione Antihyperglycaemic Agents. Part 3: The effects of stereochemistry on the potency of α-Methoxy-β-phenypropanoic Acids", *Bioorg. Med. Chem.* (1999), 7:821-830; XP-000995637; Elsevier Science Limited.

Henke, B., et al., "N-(2-Benzolphenyl)-L-tyrosine PPARγ Agonists. 1. Discovery of a Novel Series of Potent Antihyperglycemic and Antihyperlipidemic Agents", *J. Med. Chem.* (1998), 41:5020-5036; XP-000864731; American Chemical Society.

*Patent Abstracts of Japan* (2001), vol. 2000, No. 19.

Rahbar, S., et al., "Novel Inhibitors of Advanced Glycation Endproducts", *Biochem. Biophys. Reas. Comm.* (1999), 262: 651-656; XP-000946146; Academic Press.

Kletzien, R.F., et al., "Enhancement of Adipocyte Differentiation by an Insulin-Sensitizing Agent," *Molecular Pharmacology* (Feb. 1, 1992) 41(2):393-8, XP002081233, The American Society for Pharmacology and Experimental Therapeutics.

Sohda, T., et al., "Studies on Antidiabetic Agents, II. Synthesis of 5-[4-(1-Methylcyclohexylmethoxy)-benzyl] thiazolidine-2,4-dione (ADD-3878) and its Derivatives," *Chem. Pharm. Bull.* (1982) 30(10):3580-3600, XP002042079.

Unangst, P.C., et al., "Synthesis and Biological Evaluation of 5-[[(3,5-Bis(1,1-dimethylethyl)-4-hydroxy phenyl] methylene]oxazoles, -thiazoles, and -imidazoles: Novel Dual 5-Lipoxygenase and Cyclooxygenase Inhibitors with Antiinflammatory Activity," *J. Med. Chem.* (1994) 37(2): 322-8, XP002127023, American Chemical Society.

Crespi, C., "Higher-throughput screening with human cytochromes P450", *Current Opinion in Drug Discovery & Development*, (1999) 2(1): 15-19., Current Drugs Ltd.

Suzuki et al., Chemical Abstracts, vol. 122 :174262, 1995.

Khalli et al., Chemical Abstracts, vol. 110 :38850, 1989.

Crespi, C.L., et al., "Microtiter Plate Assays for Inhibition of Human, Drug-Metabolizing Cytochromes P450," *Anal. Biochem.* (1997) 248:188-190, Pub: Aademic Press.

Favreau, L.V., et al., "Improved Reliability of the Rapid Microtiter Plate Assay Using Recombinant Enzyme in Predicting CYP2D6 Inhibition in Human Liver Microsomes," *Drug Metab. & Dispos.* (1999) 27(4):436-439, Pub: The American Society for Pharmacology & Experimental Therapeutics.

Houston, J.B., "Utility of in Vitro Drug Metabolism Data in Predicting in Vivo Metabolic Clearance," *Biochem. Pharmacol*, (1994) 47(9):1469-79; Pub: Elsevier Science Ltd., Great Britian.

Irvine, J.D., et al., "MDCK (Madin-Darby Canine Kidney) Cells: A Tool for Membrane Permeability Screening," *J. Pharm. Sci.* (1999) 88(1):28-33, Pub: American Chemical Society and American Pharmacological Society.

Korzekwa, K.R., et al., "Evaluation of Atypical Cytochrome P450 Kinetics With Two-Substrate Models: Evidence That Multiple Substrates Can Simultaneously Bind to Cytochrome P450 Active Sites," *Biochemistry* (1998) 37: 4137-47.

Kostrubsky, V.E., et al., "Effect of Taxol on Cytochrome P450 3A and Acetaminophen Toxicity in Cultured Rat Hepatocytes: Comparison to Dexamethasone," *Toxicol. & Appl. Pharmacol*. (1997) 142:79-86, Article No. TO968023; Pub: Academic Press.

Stewart, B.H., et al., "Comparison of Intestinal Permeabilities Determined in Multiple in Vitro and in Situ Models: Relationship to Absorption in Humans," *Pharm. Res*. (1995) 12(5):693-99; Pub: Plenum Publishing Corp.

Swanson, H.I. and Bradfield, C.A., "The AH-Receptor: Genetics, Structure and Function," *Pharmacogenetics* (1993) 3:213-30; Pub: Chapman & Hall.

Tiller, P.R., et al., "Immobilized Human Serum Albumin: Liquid Chromatography/Mass Sepctrometry as a Method of Determining Drug-Protein Binding," *Rapid Comm. in Mass Spectrometry* (1995) 9:261-3; Pub: John Wiley & Sons, Ltd.

i) NaNO₂ and HCl in water. (ii) methyl acrylate and cuprous oxide.
(iii) Thiourea/NaOAc. (iv) HCl in water. (v) BBr₃ in methylene chloride.

(i) DCC/DMAP in methylene chloride

▭−COOH and ▭−OH = X as described in Table I.

R₁ as in Tables II to V
R₂ and R₃ = H or CH₃

(i) Et₃N/Ac₂O/DMAP, then H₂O/KOH pH9.0. (ii) 6N HCl, then MeOH/SOCl₂. (iii) R₁COCl/Et₃N.
(iv) H₂SO4 (cat) in EtOAc. (v) LiOH in MeOH/H₂O. (vi) LAH/THF. (vii) B₂H₆, or SOCl₂ then NaBH₄.

R1 as in Tables II to V (i) NaNO₂/AcOH. (ii) Zn powder. (iii) R₁COCl/Et₃N. (iv) H₂SO₄ (cat) in EtOAc. (v) LAH/THF. (vi) LiOH in MeOH/H₂O.

R1 as in Tables II to V (i) NaNO₂/AcOH. (ii) Zn powder. (iii) R₁COCl/Et₃N. (iv) H₂SO₄ (cat) in EtOAc. (v) NaBH₄.
(vi) CH₃MgBr in THF.

$R_1$ as in Tables II to V
$R_2$ and $R_3$ = H or $CH_3$ (i) Lawesson's reagent. (ii) Toluene/Δ (iii) LAH/THF. (iv) LiOH in MeOH/H₂O.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) $Et_3N$/THF. (ii) DCC/DMAP in methylene chloride.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) $Et_3N$/THF. (ii) DCC/DMAP in methylene chloride.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) $Et_3N$/THF. (ii) DCC/DMAP in methylene chloride.

P and Q = H or double bond
Y = 2-Benzoxazolyl, 2-Benzothiazolyl, 2-Pyridyl, 4,5-Dimethyl-2-thiazolyl,
(R)-6-Hydroxy-2,5,7,8-tetramethylchromanyl-2-methyl,
(S)-6-Hydroxy-2,5,7,8-tetramethylchromanyl-2-methyl (i) $Et_3N$/THF. (ii) DCC/DMAP in methylene chloride.

P and Q = H or double bond
Y = (R)-6-Hydroxy-2,5,7,8-tetramethylchroman-2-carbonyl,
(S)-6-Hydroxy-2,5,7,8-tetramethylchroman-2-carbonyl,
(R)-2,3-Dihydro-2,2,5,6,7-pentamethyl-5-hydroxy-benzofuran-3-carbonyl,
(R)-2,3-Dihydro-2,2,5,6,7-pentamethyl-5-hydroxy-benzofuran-3-carbonyl.

(i) DCC/DMAP in methylene chloride. (ii) LiOH in MeOH/H2O.
(iii) DCC/DMAP in methylene chloride.

P and Q = H or double bond
Y = (R)-6-Hydroxy-2,5,7,8-tetramethylchroman-2-carbonyl,
(S)-6-Hydroxy-2,5,7,8-tetramethylchroman-2-carbonyl,
(R)-2,3-Dihydro-2,2,5,6,7-pentamethyl-5-hydroxy-benzofuran-3-carbonyl,
(R)-2,3-Dihydro-2,2,5,6,7-pentamethyl-5-hydroxy-benzofuran-3-carbonyl.

(i) DCC/DMAP in methylene chloride.

P and Q = H or double bond
Y = (R)-6-Hydroxy-2,5,7,8-tetramethylchroman-2-carbonyl,
(S)-6-Hydroxy-2,5,7,8-tetramethylchroman-2-carbonyl,
(R)-2,3-Dihydro-2,2,5,6,7-pentamethyl-5-hydroxy-benzofuran-3-carbonyl,
(R)-2,3-Dihydro-2,2,5,6,7-pentamethyl-5-hydroxy-benzofuran-3-carbonyl.

(i) DCC/DMAP in methylene chloride. (iii) LiOH in MeOH/H2O.
(iii) DCC/DMAP in methylene chloride.

P and Q = H or double bond
Y = (R)-6-Hydroxy-2,5,7,8-tetramethylchroman-2-carbonyl, (S)-6-Hydroxy-2,5,7,8-tetramethylchroman-2-carbonyl, (R)-2,3-Dihydro-2,2,5,6,7-pentamethyl-5-hydroxy-benzofuran-3-carbonyl, (R)-2,3-Dihydro-2,2,5,6,7-pentamethyl-5-hydroxy-benzofur 3-carbonyl.

(i) DCC/DMAP in methylene chloride.

(i) EDC in methylene chloride. (ii) SOCl₂. (iii) H₂/Pd/C. (iv) DCC/DMAP/1 in methylene ch

MATERIALS AND METHODS FOR THE TREATMENT OF DIABETES, HYPERLIPIDEMIA, HYPERCHOLESTEROLEMIA, AND ATHEROSCLEROSIS

CROSS-REFERENCE TO RELATED APPLICATIONS

This application is a Divisional application of U.S. patent application Ser. No. 09/841,351, filed Apr. 24, 2001 now U.S. Pat. No. 6,680,387, which claims the benefit of U.S. Provisional Application 60/199,146, filed Apr. 24, 2000 and 60/281,982, filed Apr. 6, 2001, the disclosures of which are each incorporated by reference in their entireties, including all figures, tables, and chemical structures.

BACKGROUND OF THE INVENTION

Diabetes is one of the most prevalent chronic disorders worldwide with significant personal and financial costs for patients and their families, as well as for society. Different types of diabetes exist with distinct etiologies and pathogeneses. For example, diabetes mellitus is a disorder of carbohydrate metabolism, characterized by hyperglycemia and glycosuria and resulting from inadequate production or utilization of insulin.

Noninsulin-dependent diabetes mellitus (NIDDM), often referred to as Type II diabetes, is a form of diabetes that occurs predominantly in adults who produce adequate levels of insulin but who have a defect in insulin-mediated utilization and metabolism of glucose in peripheral tissues. Overt NIDDM is characterized by three major metabolic abnormalities: resistance to insulin-mediated glucose disposal, impairment of nutrient-stimulated insulin secretion, and overproduction of glucose by the liver. It has been shown that for some people with diabetes a genetic predisposition results from a mutation in the gene(s) coding for insulin and/or the insulin receptor and/or insulin-mediated signal transduction factor(s), thereby resulting in ineffective insulin and/or insulin-mediated effects thus impairing the utilization or metabolism of glucose.

For people with Type II diabetes, insulin secretion is often enhanced, presumably to compensate for insulin resistance. Eventually, however, the B-cells fail to maintain sufficient insulin secretion to compensate for the insulin resistance. Mechanisms responsible for the B-cell failure have not been identified, but may be related to the chronic demands placed on the B-cells by peripheral insulin resistance and/or to the effects of hyperglycemia. The B-cell failure could also occur as an independent, inherent defect in "pre-diabetic" individuals.

NIDDM often develops from certain at risk populations. One such population is individuals with polycystic ovary syndrome (PCOS). PCOS is the most common endocrine disorder in women of reproductive age. This syndrome is characterized by hyperandrogenism and disordered gonadotropin secretion producing oligo- or anovulation. Recent prevalence estimates suggest that 5–10% of women between 18–44 years of age (about 5 million women, according to the 1990 census) have the full-blown syndrome of hyperandrogenism, chronic anovulation, and polycystic ovaries. Despite more than 50 years since its original description, the etiology of the syndrome remains unclear. The biochemical profile, ovarian morphology, and clinical features are non-specific; hence, the diagnosis remains one of exclusion of disorders, such as androgen-secreting tumors, Cushing's Syndrome, and late-onset congenital adrenal hyperplasia. PCOS is associated with profound insulin resistance resulting in substantial hyperinsulinemia. As a result of their insulin resistance, PCOS women are at increased risk to develop NIDDM.

NIDDM also develops from the at risk population of individuals with gestational diabetes mellitus (GDM). Pregnancy normally is associated with progressive resistance to insulin-mediated glucose disposal. In fact, insulin sensitivity is lower during late pregnancy than in nearly all other physiological conditions. The insulin resistance is thought to be mediated in large part by the effects of circulating hormones such as placental lactogen, progesterone, and cortisol, all of which are elevated during pregnancy. In the face of the insulin resistance, pancreatic B-cell responsiveness to glucose normally increases nearly 3-fold by late pregnancy, a response that serves to minimize the effect of insulin resistance on circulating glucose levels. Thus, pregnancy provides a major "stress-test" of the capacity for B-cells to compensate for insulin resistance.

Other populations thought to be at risk for developing NIDDM include persons with Syndrome X; persons with concomitant hyperinsulinemia; persons with insulin resistance characterized by hyperinsulinemia and by failure to respond to exogenous insulin; and persons with abnormal insulin and/or evidence of glucose disorders associated with excess circulating glucocorticoids, growth hormone, catecholamines, glucagon, parathyroid hormone, and other insulin-resistant conditions.

Failure to treat NIDDM can result in mortality due to cardiovascular disease and in other diabetic complications including retinopathy, nephropathy, and peripheral neuropathy. There is a substantial need for a method of treating at risk populations such as those with PCOS and GDM in order to prevent or delay the onset of NIDDM thereby bringing relief of symptoms, improving the quality of life, preventing acute and long-term complications, reducing mortality and treating accompanying disorders of the populations at risk for NIDDM.

For many years, treatment of NIDDM has involved a program aimed at lowering blood sugar with a combination of diet and exercise. Alternatively, treatment of NIDDM can involve oral hypoglycemic agents, such as sulfonylureas alone or in combination with insulin injections. Recently, alpha-glucosidase inhibitors, such as a carboys, have been shown to be effective in reducing the postprandial rise in blood glucose (Lefevre, et al., Drugs 1992; 44:29–38). In Europe and Canada another treatment used primarily in obese diabetics is metformin, a biguanide.

Compounds useful in the treatment of the various disorders discussed above, and methods of making the compounds, are known and some of these are disclosed in U.S. Pat. No. 5,223,522 issued Jun. 29, 1993; U.S. Pat. No. 5,132,317 issued Jul. 12, 1992; U.S. Pat. No. 5,120,754 issued Jun. 9, 1992; U.S. Pat. No. 5,061,717 issued Oct. 29, 1991; U.S. Pat. No. 4,897,405 issued Jan. 30, 1990; U.S. Pat. No. 4,873,255 issued Oct. 10, 1989; U.S. Pat. No. 4,687,777 issued Aug. 18, 1987; U.S. Pat. No. 4,572,912 issued Feb. 25, 1986; U.S. Pat. No. 4,287,200 issued Sep. 1, 1981; U.S. Pat. No. 5,002,953, issued Mar. 26, 1991; U.S. Pat. Nos. 4,340,605; 4,438,141; 4,444,779; 4,461,902; 4,703,052; 4,725,610; 4,897,393; 4,918,091; 4,948,900; 5,194,443; 5,232,925; and 5,260,445; WO 91/07107; WO 92/02520; WO 94/01433; WO 89/08651; and JP Kokai 69383/92. The compounds disclosed in these issued patents and applications are useful as therapeutic agents for the treatment of diabetes, hyperglycemia, hypercholesterolemia, and hyperlipidemia. The teachings of these issued patents are incorporated herein by reference in their entireties.

Drug toxicity is an important consideration in the treatment of humans and animals. Toxic side effects resulting from the administration of drugs include a variety of conditions that range from low-grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is typically the result of metabolic activity upon the drug and the subsequent excretion of the drug from the body. Metabolic activity can take place within the vascular supply and/or within cellular compartments or organs. The liver is a principal site of drug metabolism. The metabolic process can be categorized into synthetic and nonsynthetic reactions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

One of the drugs used to treat Type II diabetes is troglitazone. The major side effects of troglitazone are nausea, peripheral edema, and abnormal liver function. Other reported adverse events include dyspnea, headache, thirst, gastrointestinal distress, insomnia, dizziness, incoordination, confusion, fatigue, pruritus, rash, alterations in blood cell counts, changes in serum lipids, acute renal insufficiency, and dryness of the mouth. Additional symptoms that have been reported, for which the relationship to troglitazone is unknown, include palpitations, sensations of hot and cold, swelling of body parts, skin eruption, stroke, and hyperglycemia. Accordingly, forms of glitazones which have fewer, or no, adverse effects (i.e., less toxicity) are desirable.

The principal difference between the compounds of the present invention and related compounds is the presence of a carboxyl group, either OOC— or COO—, directly attached to the 4-position of the phenyl ring. In the literature, thiazolidinediones having similar therapeutic properties have an ether function at the 4-position of the phenyl ring instead of a carboxyl group.

The presence of the carboxyl group has significant consequences for the biological behavior of these new compounds. The present compounds are primarily metabolized by hydrolytic enzymatic systems, whereas compounds having an ether function are metabolized only by oxidative enzymes. Hydrolytic enzymatic systems are ubiquitous, non-oxidative, not easily saturable, and non-inducible, and, therefore, reliable. By contrast, oxidative systems are mediated by the P-450 isozymes. These systems are localized, mainly, in the liver, saturable and inducible (even at low concentrations of therapeutic compounds) and therefore are highly unreliable.

The compounds of the subject invention do not rely on saturable hepatic systems for their metabolism and elimination, whereas the prior art compounds exert a heavy bio-burden on hepatic functions, especially in the presence of other drugs that rely on similar enzymes for detoxification. Thus, the present compounds have a much more desirable toxicity profile than prior art compounds, especially when considering liver toxicity and potentially fatal drug-drug interactions.

Upon metabolism by plasma and tissue esterases, the compounds of this invention are hydrolyzed into 2 types of molecules: 1) an alcohol or a phenol, and 2) a carboxylic acid. Therefore, any compound that yields compound 1, compound 2, compound 3, or compound 4, as defined in Table I, as a primary metabolite falls under the definition of this invention. This concept is illustrated in FIG. 1, taking compound 9 (of Table I) and compound 145 (of Table X) as specific examples of compounds giving 1 and 3, respectively, upon non-oxidative metabolism by esterases.

BRIEF SUMMARY OF THE INVENTION

The subject invention provides materials and methods for the safe and effective treatment of diabetes, hyperlipidemia, hypercholesterolemia, and atherosclerosis. In a preferred embodiment, the subject invention provides therapeutic compounds for the treatment of diabetes. The compounds of the subject invention can be used to treat at-risk populations, such as those with PCOS and GDM, in order to prevent or delay the onset of NIDDM thereby bringing relief of symptoms, improving the quality of life, preventing acute and long-term complications, reducing mortality and treating accompanying disorders.

Advantageously, the subject invention provides compounds that are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of treatment for Type II diabetes, hyperlipidemia, hypercholesterolemia, and atherosclerosis.

In a further embodiment, the subject invention pertains to the breakdown products that are formed when the therapeutic compounds of the subject invention are acted upon by esterases. These breakdown products can be used as described herein to monitor the clearance of the therapeutic compounds from a patient.

In yet a further embodiment, the subject invention provides methods for synthesizing the therapeutic compounds of the subject invention.

BRIEF DESCRIPTION OF THE TABLES

Figure 1:
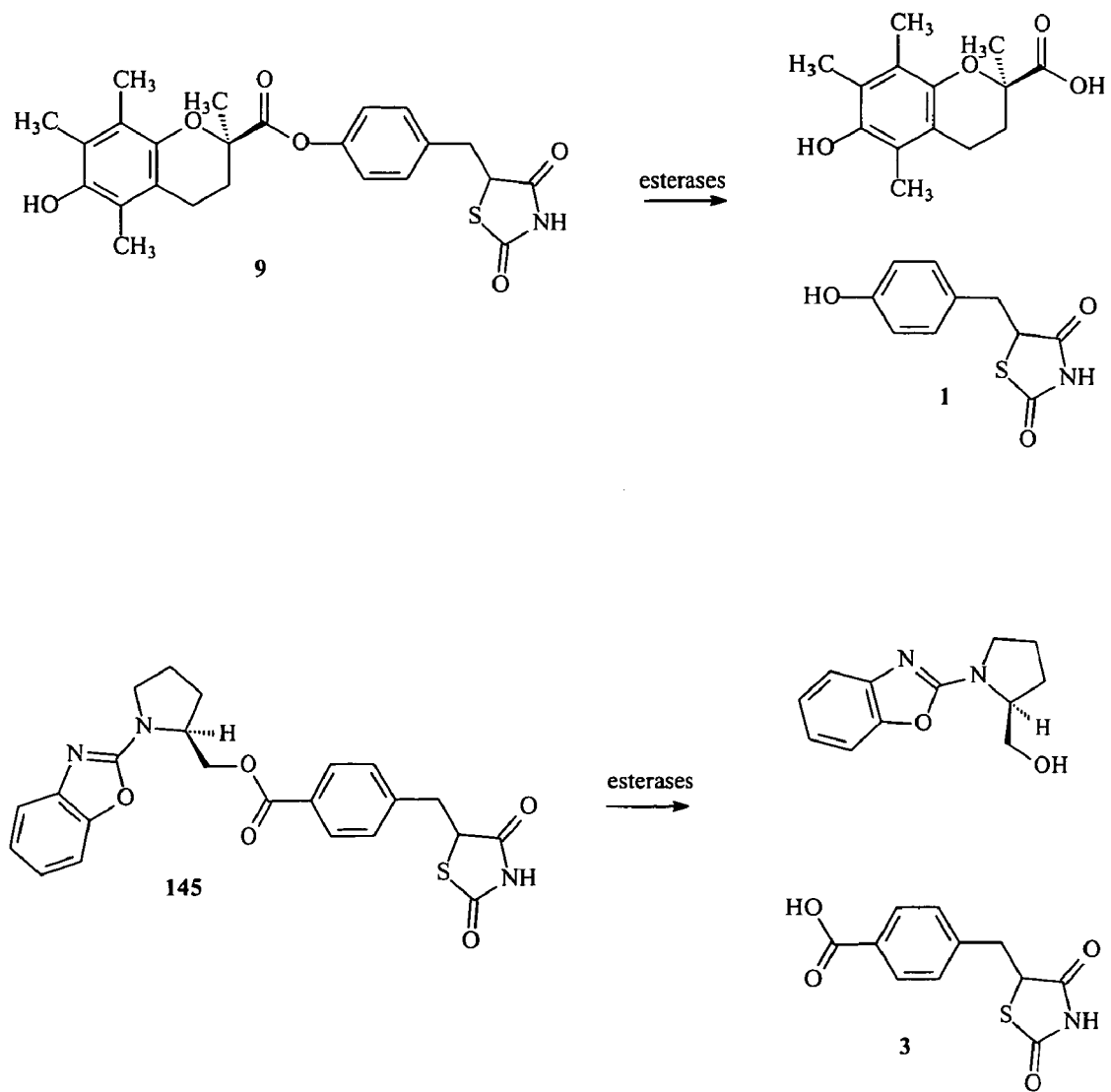
FIG. 1 depicts exemplary metabolic breakdown products resulting from the actions of esterases on compounds of the invention.

Tables I–XXII depict exemplary compounds according to the invention. The term "db" indicates a double bond between P and Q.

Table XXIII illustrates the effects of exemplary compounds on serum glucose and insulin levels in NIDDM mice.

DETAILED DISCLOSURE OF THE INVENTION

The subject invention provides materials and methods for the treatment of non-insulin dependent diabetes mellitus (NIDDM), hyperlipidemia, hypercholesterolemia, and atherosclerosis. Advantageously, the therapeutic compounds of the subject invention are stable in storage but have a shorter half-life in the physiological environment than other drugs which are available for treatment of diabetes; therefore, the compounds of the subject invention can be used with a lower incidence of side effects and toxicity, especially in patients having elevated liver function or compromised liver function.

In a preferred embodiment of the subject invention, therapeutic compounds are provided which are useful in the treatment of diabetes, hyperlipidemia, hypercholesterolemia, and atherosclerosis and which contain an ester group which is acted upon by esterases thereby breaking down the compound and facilitating its efficient removal from the treated individual. In a preferred embodiment the therapeutic compounds are metabolized by the Phase I drug detoxification system and are exemplified by the compound of Formula I.

The compounds of Formula I can be generally described as 5-benzyl- or 5-benzylidene-thiazolidine-2,4-dione compounds having a carboxyl group directly attached to the para-position of the phenyl ring. These compounds represent a new class of chemical compounds having therapeutic properties for the treatment of type-II diabetes mellitus, atherosclerosis, hypercholesterolemia, and hyperlipidemia.

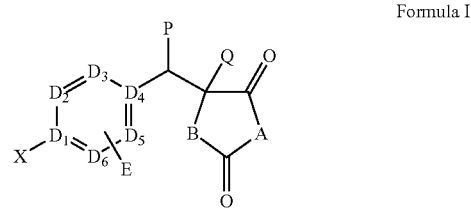

Formula I

For compounds of Formula I:
A and B may be the same or different and are C, N, NO, NH, SO$_{0-2}$, O;
D$_1$–D$_6$ can be the same or different and are C, N, S, or O;
E can be attached to one or more of the atoms located at D$_1$–D$_6$;
P and Q can be a double bond; or
P, Q, and E can be the same or different and are a moiety selected from the group consisting of H, C$_{1-10}$ alkyl, substituted alkyl groups, substituted or unsubstituted carboxylic acids, substituted or unsubstituted carboxylic esters, halogen, carboxyl, hydroxyl, phosphate, phosphonate, aryl, CN, OH, COOH, $NH_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_1$-1 alkyl, halogen, OH, $NH_2$, CN, $NO_2$, COOH, or $SO_{2-4}$. Exemplary heterocyclic groups include, but not limited to, morpholine, triazole, imidazole, pyrrolidine, piperidine, piperazine, pyrrole, dihydropyridine, aziridine, thiazolidine, thiazoline, thiadiazolidine or thiadiazoline.

Substituted carboxylic acids, substituted carboxylic esters, and substituted alkyl groups can be substituted at any available position with a moiety selected from the group consisting of $C_{1-10}$ alkyl, halogen, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

X is —OH, —COOH, or a substituted carboxylic group having the carboxyl moiety OOC— or COO— directly attached to the phenyl ring of the compound of Formula I. The carboxylic acid group can be substituted with a moiety selected from the group consisting of alkyloxycarbonyl, alkylcarbonyloxy, aryloxycarbonyl, arylcarbonyloxy, heteroalkyloxycarbonyl, heteroalkylcarbonyloxy, heteroaryloxycarbonyl, and heteroarylcarbonyloxy each of which is, optionally, substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. In other embodiments, the substituted carboxylic group can be substituted with a moiety selected from the group consisting of $C_{1-10}$ alkyl, CN, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$. Exemplary heterocyclic groups include, but are not limited to, morpholine, triazole, imidazole, pyrrolidine, piperidine, piperazine, pyrrole, dihydropyridine, aziridine, thiazolidine, thiazoline, thiadiazolidine, and thiadiazoline.

In specific embodiments, X can be hydroxyl, hydroxycarbonyl, 1-methyl-1-cyclohexylcarbonyloxy, 1-methyl-1-cyclohexylmethoxycarbonyl, 5-ethyl-2-pyridyl-acetoxy, 5-ethyl-2-pyridylmeth-oxy-carbonyl, (R)-6-hydroxy-2,5,7,8-tetramethyl-chroman-2-carboxy, (S)-6-hydroxy-2,5,7,8-tetramethylchroman-2-carboxy, (R)-6-hydroxy-2,5,7,8-tetra-methylchroman-2-ylmethoxy-carbonyl, (S)-6-hydroxy-2,5,7,8-tetramethylchroman-2-ylmethoxycarbonyl, (R)-5-hydroxy-2,2,4,6,7-pentamethyl-2,3-dihydrobenzofuran- 3-carboxy, (S)-5-hydroxy-2,2,4,6,7-pentamethyl-2,3-dihydro-benzofuran-3-carboxy, (R)-5-hydroxy-2,2,4,6,7-penta-methyl-2,3-dihydrobenzofuran-3-methoxycarbonyl, (S)-5-hydroxy-2,2,4,6,7-pentamethyl-2,3-dihydrobenzofuran-3-methoxycarbonyl, 2-hydroxybenzoyloxy, or 2,4-dihydroxybenzoyloxy.

In other embodiments, X can be

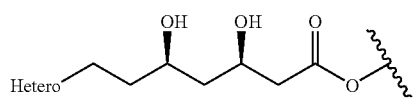

wherein Hetero is an aromatic, cyclic, or alicyclic moiety that can contain heteroatoms. In certain specific embodiments, Hetero is an aromatic, cyclic, or alicyclic moiety that contains heteroatoms that are generally part of the structure of the statin-family of lipid lowering agents. Preferred examples include, but are not limited to, 2-(4-fluorophenyl)-5-(1-methylethyl)-3-phenyl-4-[(phenylamino)carbonyl]-1-(1H-pyrrol)yl, a component of atorvastatin, and 1,2,3,7,8,8a-hexahydro-1-(2-methylbutanoyl)oxy-3,7-dimethyl-8-naphthalenyl, a component of lovastatin.

Alternatively, X can be

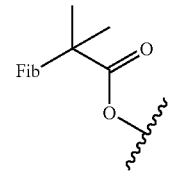

wherein Fib is an aromatic, cyclic, or alicyclic moiety that can contain heteroatoms. In certain specific embodiments, Fib moieties are part of the fibrate-family of lipid lowering agents. Preferred examples include, but are not limited to 4-(4-chlorobenzoyl)phenoxy, a component of fenofibric acid, 4-chlorophenoxy, a component of clofibric acid, and 3-(2,5-xylyloxy)-1-propyl, a component of gemfibrozil.

Alternatively, X can be

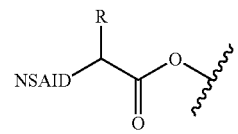

wherein R is hydrogen or methyl, and in which NSAID means an aromatic, alkyl, or cycloalkyl moiety that may contain heteroatoms and that are generally part of the family of non-steroidal anti-inflammatory agents. Preferred examples include, but are not limited to 4-(2-methyl-1-propyl)phenyl, 2-(2,6-dichloro-1-phenyl)aminophenyl, 6'-methoxy-2'-naphthyl, and 6'-methoxy-2'-naphthylmethyl.

In another embodiment, X can be

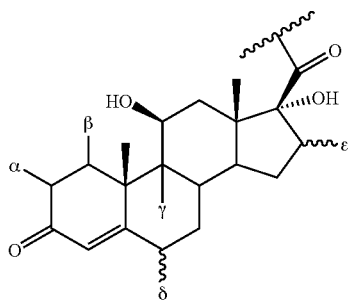

where α and β are hydrogen or α and β form a bond, and where γ, δ, and ε, are independently hydrogen, hydroxy, fluoro, chloro, or methyl.

Alternatively, X can be

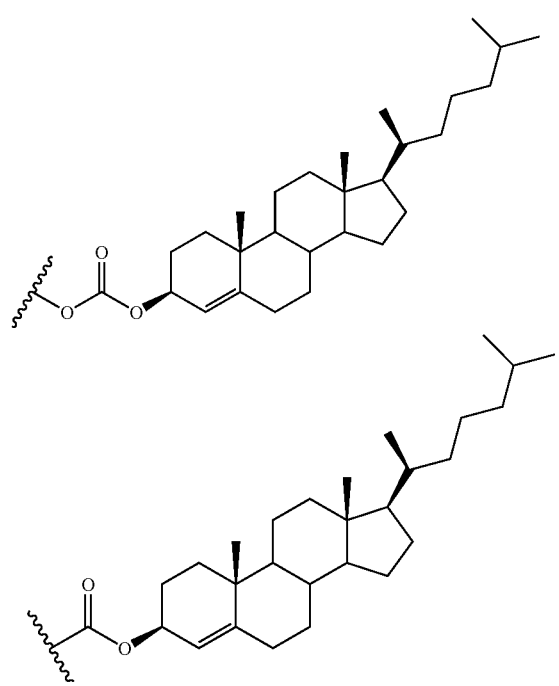

X can also be of the general formula

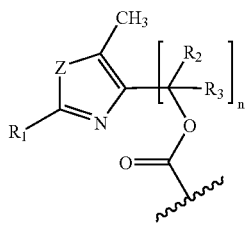

In such embodiments, n is 0 or 1, $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, 2-hydroxybenzoyl, or 2,4-dihydroxybenzoyl.

Other embodiments provide compounds wherein X is

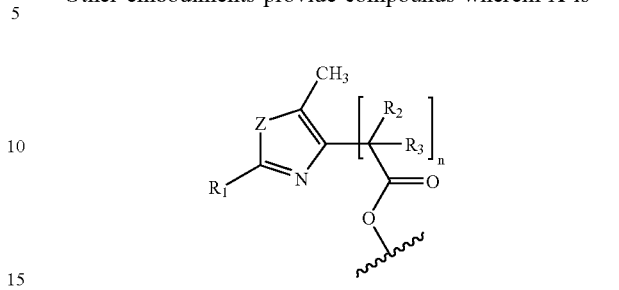

in which n is 0 or 1, $R_2$ and $R_3$ are independently hydrogen or methyl; Z is N, O, or S; and $R_1$ is aryl or heteroaryl, alkyl or heteroalkyl. Preferred non-limiting examples include compounds where R1 is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, 2-hydroxybenzoyl, or 2,4-dihydroxybenzoyl.

In other embodiments, X is a 1-substituted (R)-pyrrolidine-2-methoxycarbonyl, (S)-pyrrolidine-2-methoxycarbonyl, (R)-pyrrolidine-2-carboxy, or (S)-pyrrolidine-2-carboxy, having the following formulas

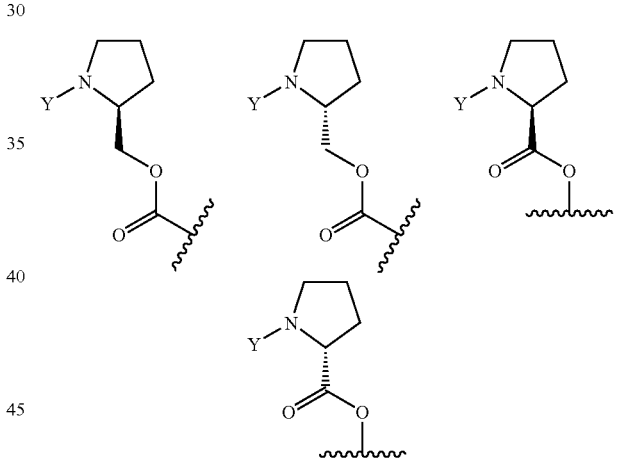

in which Y is aryl or heteroaryl, alkyl or heteroalkyl. Preferred non-limiting examples include compounds where Y is (R)-6-hydroxy-2,5,7,8-tetramethylchroman-2-carboxy, (S)-6-hydroxy-2,5,7,8-tetramethylchroman-2-carboxy, (R)-6-hydroxy-2,5,7,8-tetrameth-ylchroman-2-ylmeth-oxycarbonyl, (S)-6-hydroxy-2,5,7,8-tetra-methylchroman-2-yl-meth-oxycarbonyl, (R)-5-hydroxy-2,2,4,6,7-pentamethyl-2,3-dihydrobenzofuran- 3-carboxy, (S)-5-hydroxy-2,2,4,6,7-pentamethyl-2,3-dihydro-benzofuran-3-carboxy, (R)-5-hydroxy-2,2,4,6,7-pentamethyl-2,3-dihydrobenzofuran-3-methoxycarbonyl, (S)-5-hydroxy-2,2,4,6,7-pentamethyl-2,3-dihydrobenzofuran-3-methoxycarbonyl, 5-chloro-2-pyridyl, 5-methyl-2-pyridyl, 3-chloro-2-pyridyl, 4-methyl-2-pyridyl, 2-pyridyl, 2-benzoxazolyl, 2-benzothiazolyl, 5-amino-2-pyridyl, 5-nitro-2-pyridyl, 2-pyrazinyl, 4-phenyl-2-oxazolinyl, 5-methyl-2-thiazolinyl, 4,5-dimethyl-2-oxazolinyl, 4,5-dimethyl-2-thiazolinyl, 5-phenyl-2-thiazolinyl, 2-thiazolinyl, 4-methyl-5-phenyl-2-thiazolinyl, 5-methyl-4-phenyl-2-thiazolinyl, 2-piperidinyl, 4-phenyl-2-piperidinyl, 6-methyl-2-pyridinyl, 6-methoxy-2-pyridinyl, 2-hydroxybenzoyl, or 2,4-dihydroxybenzoyl.

Alternatively X is an N-substituted 2-methylaminoethoxycarbonyl or a N-substituted 2-methylaminoacetoxy, having the following formulas:

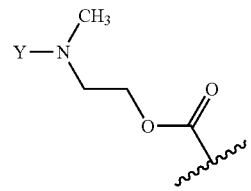 or 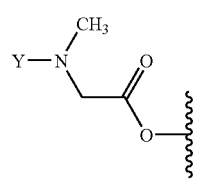

in which Y is aryl or heteroaryl, alkyl or heteroalkyl. Preferred non-limiting examples include compounds where Y is (R)-6-hydroxy-2,5,7,8-tetramethylchroman-2-carboxy, (S)-6-hydroxy-2,5,7,8-tetramethylchroman-2-carboxy, (R)-6-hydroxy-2,5,7,8-tetramethylchroman-2-ylmeth-oxycarbonyl, (S)-6-hydroxy-2,5,7,8-tetra-methylchroman-2-yl-methoxycarbonyl, (R)-5-hydroxy-2,2,4,6,7-pentamethyl-2,3-dihydrobenzofuran-3-carboxy, (S)-5-hydroxy-2,2,4,6,7-pentamethyl-2,3-dihydro-benzofuran-3-carboxy, (R)-5-hydroxy-2,2,4,6,7-pentamethyl-2,3-dihydrobenzofuran-3-methoxycarbonyl, (S)-5-hydroxy-2,2,4,6,7-pentamethyl-2,3-dihydrobenzofuran-3-methoxycarbonyl, 5-chloro-2-pyridyl, 5-methyl-2-pyridyl, 3-chloro-2-pyridyl, 4-methyl-2-pyridyl, 2-pyridyl, 2-benzoxazolyl, 2-benzothiazolyl, 5-amino-2-pyridyl, 5-nitro-2-pyridyl, 2-pyrazinyl, 4-phenyl-2-oxazolinyl, 5-methyl-2-thiazolinyl, 4,5-dimethyl-2-oxazolinyl, 4,5-dimethyl-2-thiazolinyl, 5-phenyl-2-thiazolinyl, 2-thiazolinyl, 4-methyl-5-phenyl-2-thiazolinyl, 5-methyl-4-phenyl-2-thiazolinyl, 2-piperidinyl, 4-phenyl-2-piperidinyl, 6-methyl-2-pyridinyl, 6-methoxy-2-pyridinyl, 2-hydroxybenzoyl, or 2,4-dihydroxybenzoyl.

X can also be a 1-substituted (R)-pyrrolidine-2-methoxycarbonyl, (S)-pyrrolidine-2-methoxycarbonyl, (R)-pyrrolidine-2-carboxy, or (S)-pyrrolidine-2-carboxy, having the following formulas:

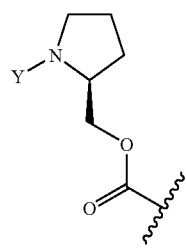 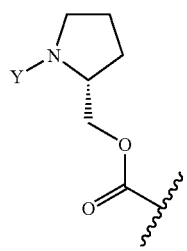 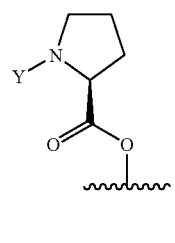

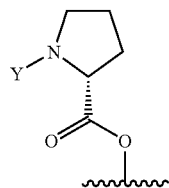

wherein Y is

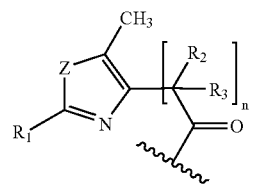

n is 0 or 1; $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, or 2-pyrazinyl; or Y is

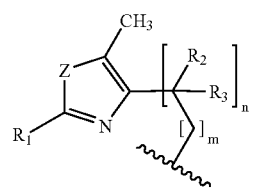

n is 0 or 1; m is 0 or 1; $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl- 2-thiophenyl, 5-methyl-2-thiophenyl, 5-methyl-3-isoxazolyl, 2-pyridyl, 4-pyridyl, or 2-pyrazinyl; or Y is

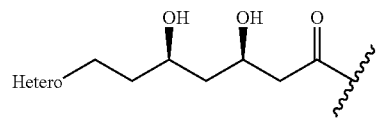

wherein Hetero is an aromatic, cyclic, or alicyclic moiety that usually contains heteroatoms. In certain specific embodiments, these moieties are part of the structure of the statin-family of lipid lowering agents. Preferred examples include, but are not limited to, 2-(4-fluorophenyl)-5-(1-methylethyl)-3-phenyl-4-[(phenylamino)carbonyl]-1-(1H-pyrrol)yl, a component of atorvastatin, and 1,2,3,7,8,8a-hexahydro-1-(2-methylbutanoyl)oxy-3,7-dimethyl-8-naphthalenyl, a component of lovastatin; or Y is

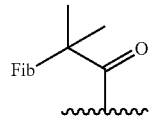

wherein Fib is an aromatic, cyclic, or alicyclic moiety that contains heteroatoms. In some embodiments, these moieties are part of the fibrate-family of lipid lowering agents.

Preferred examples include, but are not limited to 4-(4-chlorobenzoyl)phenoxy, a component of fenofibric acid, 4-chlorophenoxy, a component of clofibric acid, and 3-(2, 5-xylyloxy)-1-propyl, a component of gemfibrozil; or Y is

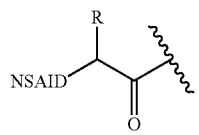

wherein R is hydrogen or methyl, and in which NSAID means an aromatic, alkyl, or cycloalkyl moiety that may contain heteroatoms and that are generally part of the family of non-steroidal anti-inflammatory agents. Preferred examples include, but are not limited to 4-(2-methyl-1-propyl)phenyl, 2-(2,6-dichloro-1-phenyl)aminophenyl, 6'-methoxy-2'-naphthyl, and 6'-methoxy-2'-naphthylmethyl or Y can be

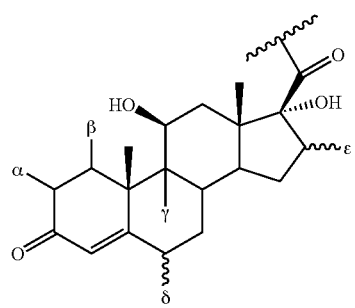

where α and β are hydrogen or α and β form a bond, and where γ, δ, and ε, are independently hydrogen, hydroxy, fluoro, chloro, or methyl; or Y can be

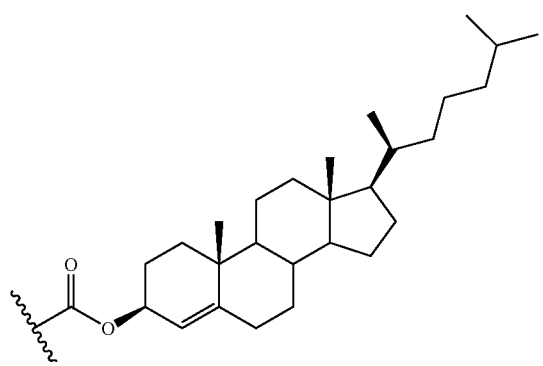

or

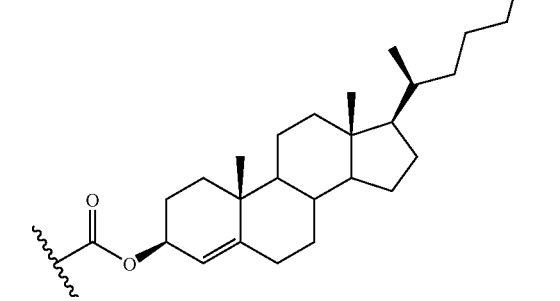

Alternatively X can be an N-substituted 2-methylaminoethoxycarbonyl or an N-substituted 2-methylaminoacetoxy, having the following formulas:

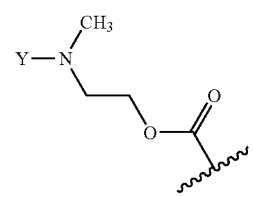 or 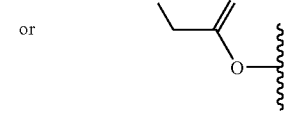

wherein Y is

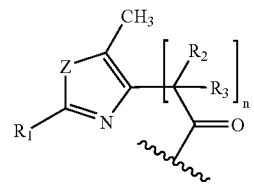

$n$ is 0 or 1; $R_2$ and $R_3$ are independently hydrogen or methyl; Z is N, O, or S; and $R_1$ is aryl, heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, or 2-pyrazinyl, 2-hydroxybenzoyl, or 2,4-dihydroxybenzoyl; or Y is

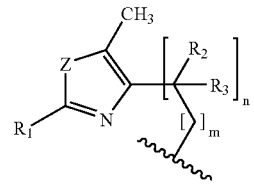

$n$ is 0 or 1; $m$ is 0 or 1; $R_2$ and $R_3$ are independently hydrogen or methyl; Z is N, O, or S; and $R_1$ is aryl or heteroaryl, alkyl or heteroalkyl. Preferred non-limiting examples include compounds where $R_1$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, 2-hydroxybenzoyl, or 2,4-dihydroxybenzoyl; or Y is

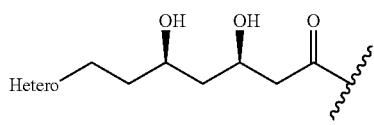

wherein Hetero is an aromatic, cyclic, or alicyclic moiety that contains heteroatoms. In certain specific embodiments, these moieties are part of the structure of the statin-family of lipid lowering agents. Preferred examples include, but are not limited to, 2-(4-fluorophenyl)-5-(1-methylethyl)-3-phenyl-4-[(phenylamino)carbonyl]-1-(1H-pyrrol)yl, a component of atorvastatin, and 1,2,3,7,8,8a-hexahydro-1-(2-methylbutanoyl)oxy-3,7-dimethyl-8-naphthalenyl, a component of lovastatin; or Y is

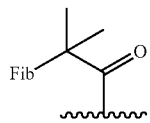

wherein Fib is an aromatic, cyclic, or alicyclic moiety that contains heteroatoms. In some embodiments, these moieties are part of the fibrate-family of lipid lowering agents. Preferred examples include, but are not limited to 4-(4-chlorobenzoyl)phenoxy, a component of fenofibric acid, 4-chlorophenoxy, a component of clofibric acid, and 3-(2,5-xylyloxy)-1-propyl, a component of gemfibrozil; or Y is

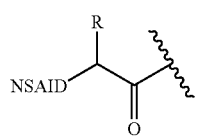

wherein R is hydrogen or methyl, and in which NSAID means an aromatic, alkyl, or cycloalkyl moiety that may contain heteroatoms and that are generally part of the family of non-steroidal anti-inflammatory agents. Preferred examples include, but are not limited to 4-(2-methyl-1-propyl)phenyl, 2-(2,6-dichloro-1-phenyl)aminophenyl, 6'-methoxy-2'-naphthyl, and 6'-methoxy-2'-naphthylmethyl; or Y can be

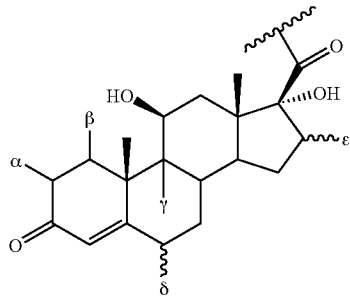

where $\alpha$ and $\beta$ are hydrogen or $\alpha$ and $\beta$ form a bond, and where $\gamma$, $\delta$, and $\epsilon$, are independently hydrogen, hydroxy, fluoro, chloro, or methyl; or Y can be

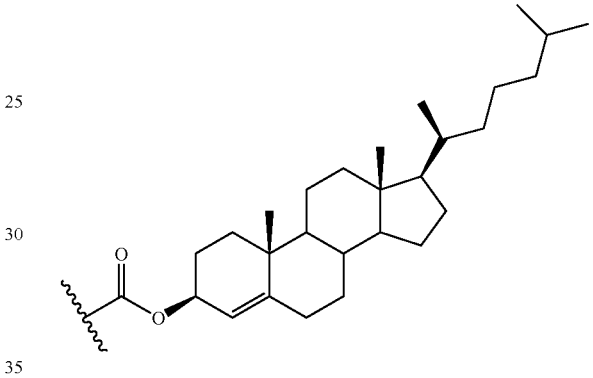

Other embodiments provide compounds wherein X is

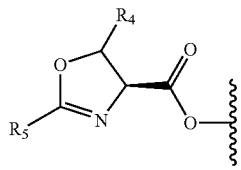

$R_4$ is hydrogen or methyl, and where $R_5$ is aryl or heteroaryl, alkyl or heteroalkyl. Preferred non-limiting examples include compounds where $R_5$ is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, (R)-6-hydroxy-2,5,7,8-tetramethyl-2-chromanyl, (S)-6-hydroxy-2,5,7,8-tetramethyl-2-chromanyl, (R)-5-hydroxy-2,2,4,6,7-pentamethyl-2,3-dihydro-3-benzofuranyl, or (S)-5-hydroxy-2,2,4,6,7-pentamethyl-2,3-dihydro-3-benzo-furanyl.

X can also be

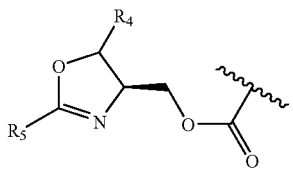

wherein $R_4$ is hydrogen or methyl, and where R5 is aryl or heteroaryl, alkyl or heteroalkyl. Preferred non-limiting examples include compounds where R5 is phenyl, 4-fluorophenyl, 4-methoxyphenyl, 3-methyl-2-thiophenyl, 5-methyl-2-thiophenyl, 5-methyl-3-isoxazolyl, 2-pyridyl, 4-pyridyl, 2-pyrazinyl, (R)-6-hydroxy-2,5,7,8-tetramethyl-2-chromanyl, (S)-6-hydroxy-2,5,7,8-tetramethyl-2-chromanyl, (R)-5-hydroxy-2,2,4,6,7-pentamethyl-2,3-dihydro-3-benzofuranyl, or (S)-5-hydroxy-2,2,4,6,7-pentamethyl-2,3-dihydro-3-benzofuranyl.

In one embodiment, A is NH; B is sulfur (S); P and Q are a double bond or hydrogen (H); E is hydrogen (H) and is attached to each of $D_1$ through $D_6$; $D_1$ through $D_6$ are carbon (C); and X can be any of the structures provided supra.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

As used in this application, the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

Analogs or derivatives of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

The subject invention further provides methods of treating disorders, such as diabetes, atherosclerosis, hypercholesterolemia, and hyperlipidemia, comprising the administration of a therapeutically effective amount of esterified thiazolidinedione analogs to an individual in need of treatment. Thiazolidinedione based compounds include troglitazone (for example, REZULIN), pioglitazone, and rosiglitazone. Accordingly, the subject invention provides esterified thiazolidinedione analogs and pharmaceutical compositions of these esterified compounds. The compounds and compositions according to the invention can also be administered in conjunction with other therapeutic compounds, therapeutic regimens, compositions, and agents suitable for the treatment of disorders, such as diabetes, atherosclerosis, hypercholesterolemia, and hyperlipidemia. Thus, the invention includes combination therapies wherein the compounds and compositions of the invention are used in conjunction with other therapeutic agents for the treatment of disorders, such as diabetes, atherosclerosis, hypercholesterolemia, and hyperlipidemia.

The compounds of this invention have therapeutic properties similar to those of the unmodified parent compounds. Accordingly, dosage rates and routes of administration of the disclosed compounds are similar to those already used in the art and known to the skilled artisan (see, for example, Physicians' Desk Reference, 54th Ed., Medical Economics Company, Montvale, N.J., 2000).

The compounds of the subject invention can be formulated according to known methods for preparing pharmaceutically useful compositions. Formulations are described in detail in a number of sources that are well known and readily available to those skilled in the art. For example, Remington's Pharmaceutical Science by E. W. Martin describes formulations that can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds of the invention and one or more non-toxic, pharmaceutically acceptable carriers or diluents. Examples of such carriers for use in the invention include ethanol, dimethyl sulfoxide, glycerol, silica, alumina, starch, and equivalent carriers and diluents. Additional therapeutic agents suitable for the treatment of disorders such as diabetes, atherosclerosis, hypercholesterolemia, and hyper-lipidemia can also be incorporated into pharmaceutical agents according to the invention.

Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

Figure 2:
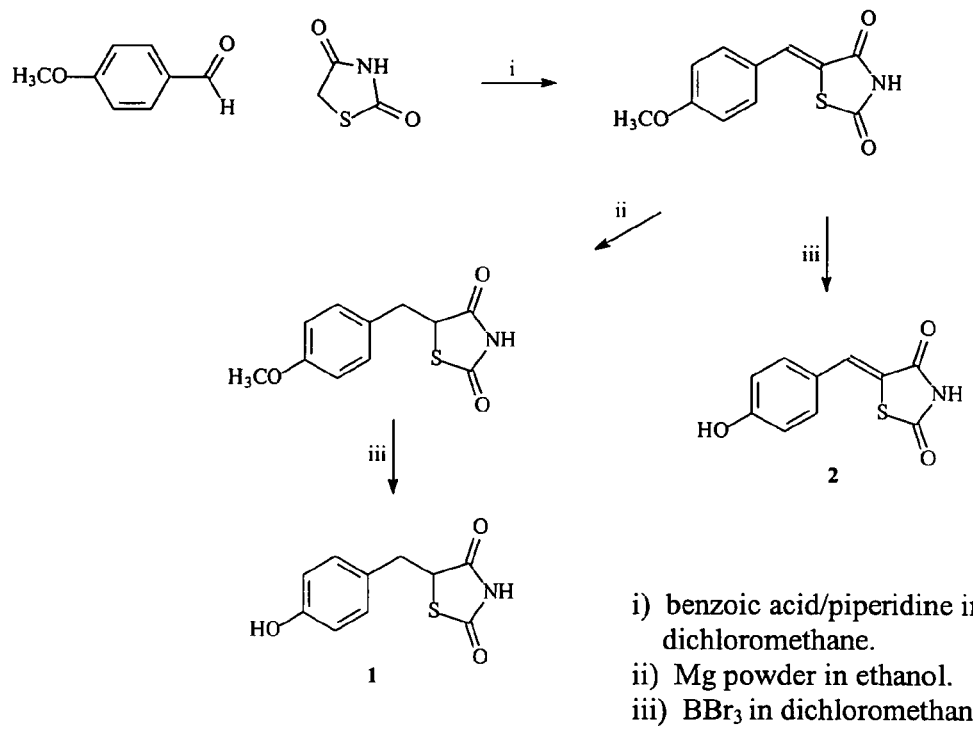
FIGS. 2–3 provide an exemplary synthetic scheme for compounds 1 through 4 (of Table I). These compounds can be conveniently prepared by the Knoevenagel reaction between an aldehyde and thiazolidine-2,4-dione using, for example, sodium acetate in acetic anhydride, or piperidine and benzoic acid in methylene chloride as a reaction medium.
Figure 3:
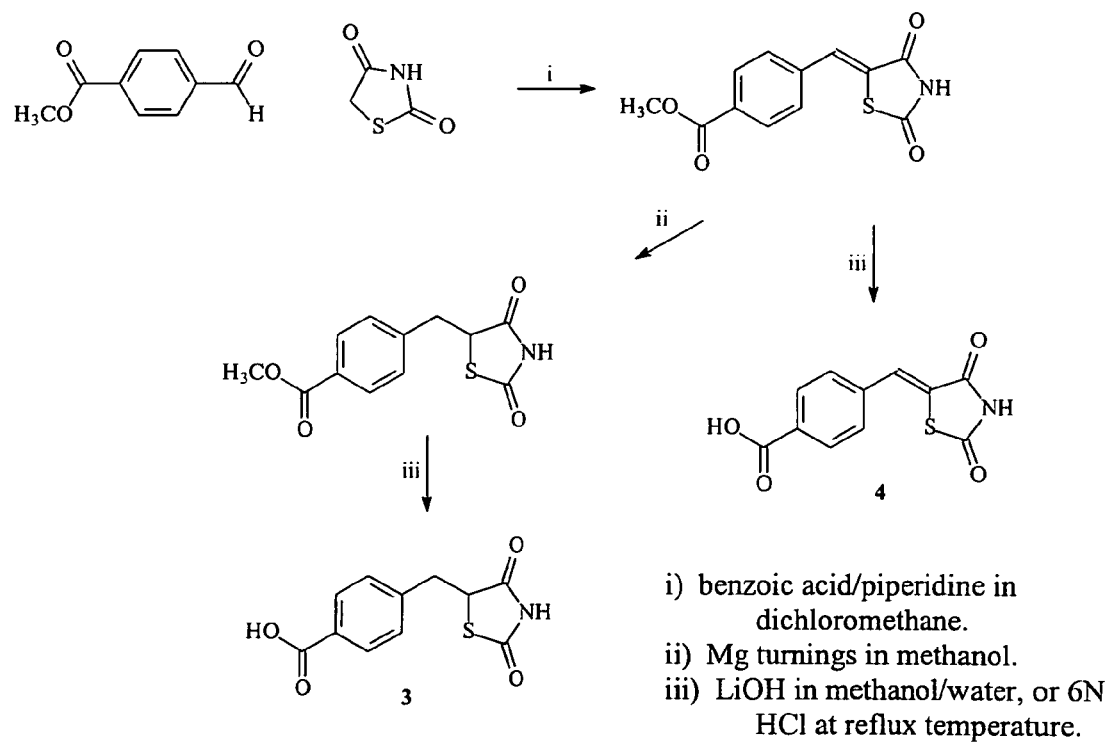
Figure 4:
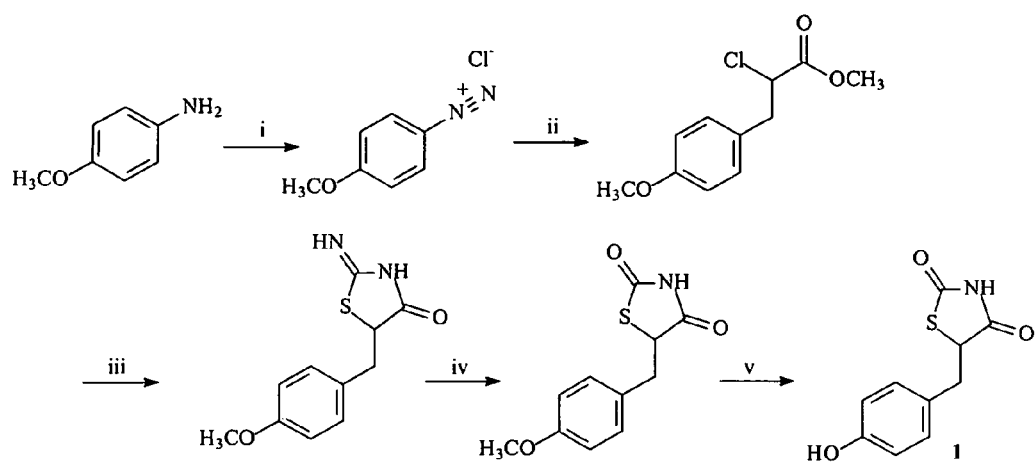
FIG. 4 illustrates an alternative reaction scheme for the production of compound 1 (of Table I). In this reaction scheme, para-anisidine undergoes a diazotation reaction with sodium nitrite and hydrochloric acid. The diazonium chloride salt undergoing, in turn, a radicalar reaction with methyl acrylate and then a cyclization reaction with thiourea, the product of which is hydrolyzed to the thiazolidinedione molecule.

Compounds 1 through 4 (of Table I) can be conveniently prepared by the Knoevenagel reaction between an aldehyde and thiazolidine-2,4-dione, using for example sodium acetate in acetic anhydride, or piperidine and benzoic acid in methylene chloride as a reaction medium. This is illustrated in FIG. 2 and FIG. 3. Alternatively, compound 1 can be prepared by the method described in FIG. 4. In this reaction scheme, para-anisidine undergoes a diazotation reaction with sodium nitrite and hydrochloric acid. The diazonium chloride salt undergoing, in turn, a radicalar reaction with methyl acrylate and then a cyclization reaction with thiourea, the product of which is hydrolyzed to the thiazolidinedione molecule.

Figure 5:
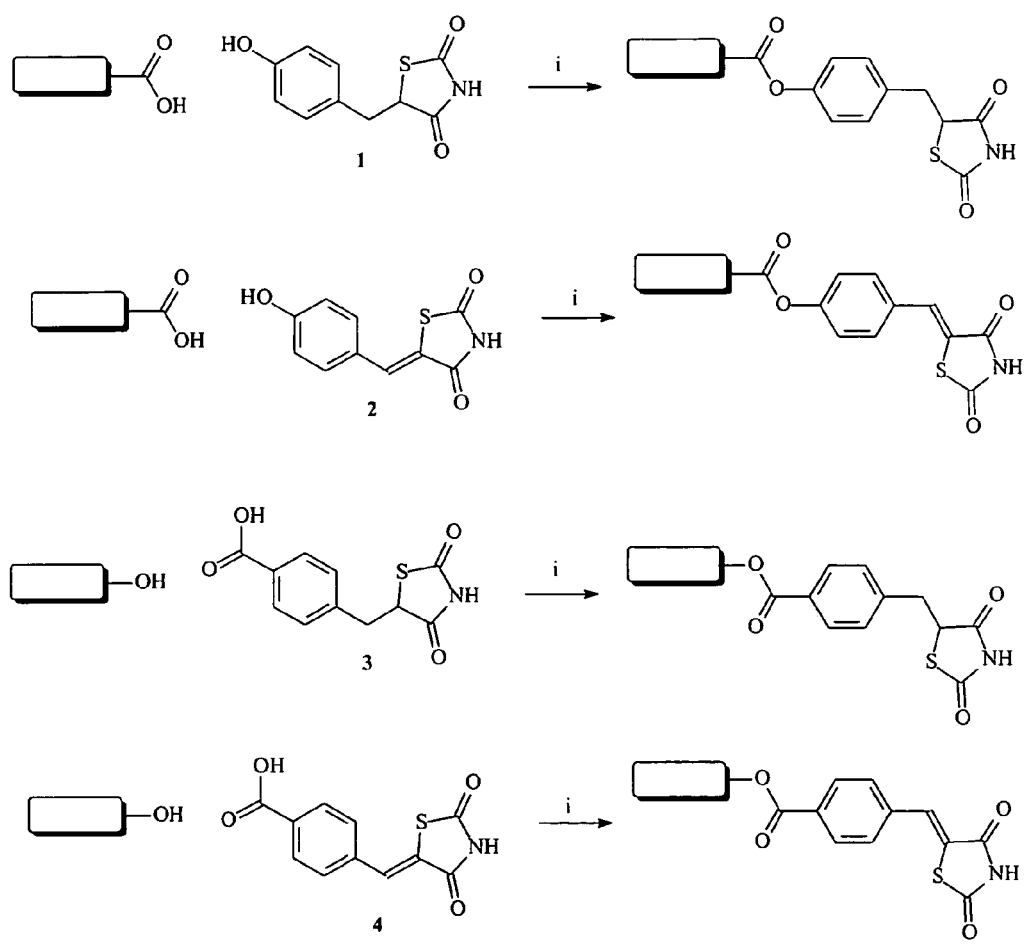
FIG. 5 shows an exemplary synthetic scheme for the compounds described in Table I (compounds 5 to 32). These compounds can be made via an esterification reaction between 1 or 2 and an appropriately substituted carboxylic acid, or between 3 or 4 and an appropriately substituted alcohol.

The compounds described in Table I (compounds 5 to 32) can all be made via an esterification reaction between 1 or 2 and an appropriately substituted carboxylic acid, or between 3 or 4 and an appropriately substituted alcohol. The esterification reaction can be facilitated by the presence of a catalyst in the reaction medium, such as a small amount of concentrated sulfuric acid for example. Preferably, especially if the alpha-position to the carbonyl is an asymmetric center, an activated functional derivative of the carboxylic acid is made. Numerous functional derivatives of carboxylic acids used in esterification reactions have been described in the scientific literature. The most commonly used activated functional derivatives are acyl chlorides, anhydrides and mixed anhydrides, and activated esters. In one aspect of this invention dicyclohexyl carbodiimide (DCC) was used as an activating agent (FIG. 5).

Compounds 33 to 104 are functionalized 5-methyloxazole and functionalized 5-methylthiazole derivatives. They all have various functional groups attached to the 2-position ($R_1$ in Tables II to V), and at the 4-position, which is the enzymatically labile link with the thiazolidine portion of the molecule. The enzymatically labile link is either an ester (COO—) or a reverse ester (OOC—) and can be substituted with 0, 1, or 2 methyl groups at the alpha-position from the oxazole or thiazole ring ($R_2$ and $R_3$ in Tables II to V).

Figure 6:
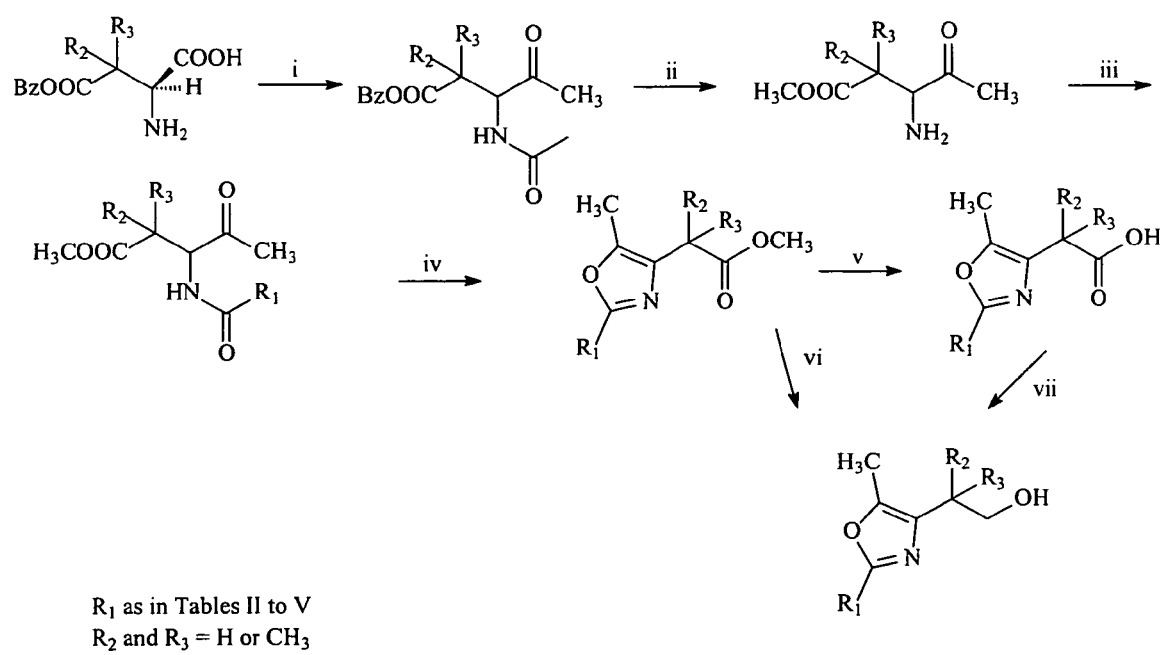
FIG. 6 depicts the synthesis of the 4-oxazoleacetic acid and the 4-oxazoleethanol moiety starting from aspartic acid derivatives in which $R_2$ and $R_3$ are methyl or hydrogen.

The synthesis of compounds 33 to 104 is described in general terms in FIGS. 7–10. FIG. 6 describes the synthesis of the 4-oxazoleacetic acid and the 4-oxazoleethanol moiety starting from aspartic acid derivatives in which $R_2$ and $R_3$ are methyl or hydrogen. In a typical example, γ-benzyl aspartate is acetylated and then decarboxylated to benzyl 3-acetamido-4-oxovalerate using acetic anhydride as an acetylating agent followed by potassium hydroxide in order to obtain the decarboxylated product. This in turn is transformed into methyl 3-amino-4-oxovalerate using standard hydrolytic and esterification procedures, for example refluxing in dilute hydrochloric acid followed by reaction with thionyl chloride and methanol. The $R_1$ group is then introduced by acylating the 3-amino group using the appropriate acyl or aroyl chloride. There is almost no limitation to the nature of the $R_1$ group being introduced at this stage, as shown in Tables II to V where various $R_1$ groups are described. Cyclization to an oxazole ring is then effected using sulfuric acid as a catalyst in ethyl acetate as a solvent. At this stage, ester hydrolysis using lithium hydroxide in methanol gives the desired 4-oxazoleacetic acid derivatives, whereas reduction of the ester with lithium aluminum hydride or reduction of the acid using diborane gives the 4-oxazoleethanol analogs.

Figure 7:
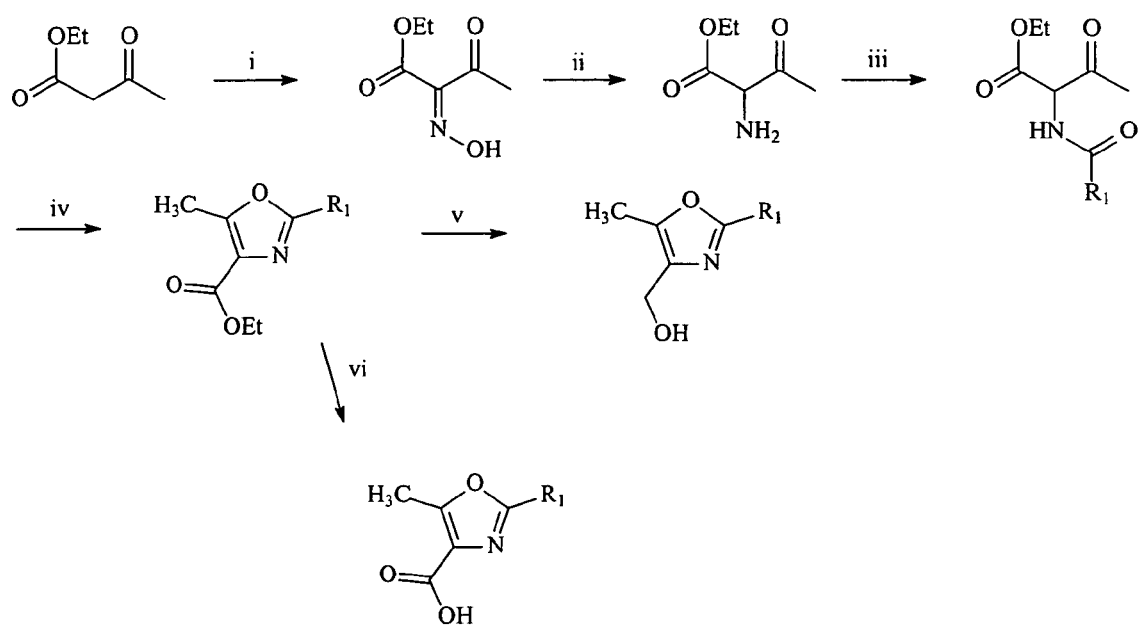
FIG. 7 describes the synthesis of the 4-oxazolecarboxylic acid and 4-oxazolemethanol groups. The synthesis starts from ethyl acetoacetate in which a 2-amino-group is introduced via oxime formation followed by reduction with zinc powder. The synthesis then proceeds as before, where the $R_1$ group is introduced by acylating the amino group, followed by cyclization with sulfuric acid in ethyl acetate, and finally ester cleavage or reduction to the alcohol.

FIG. 7 describes the synthesis of the 4-oxazolecarboxylic acid and 4-oxazolemethanol groups. The synthesis starts from ethyl acetoacetate in which a 2-amino-group is introduced via oxime formation followed by reduction with zinc powder. The synthesis then proceeds as before, where the $R_1$ group is introduced by acylating the amino group, followed by cyclization with sulfuric acid in ethyl acetate, and finally ester cleavage or reduction to the alcohol.

Figure 8:
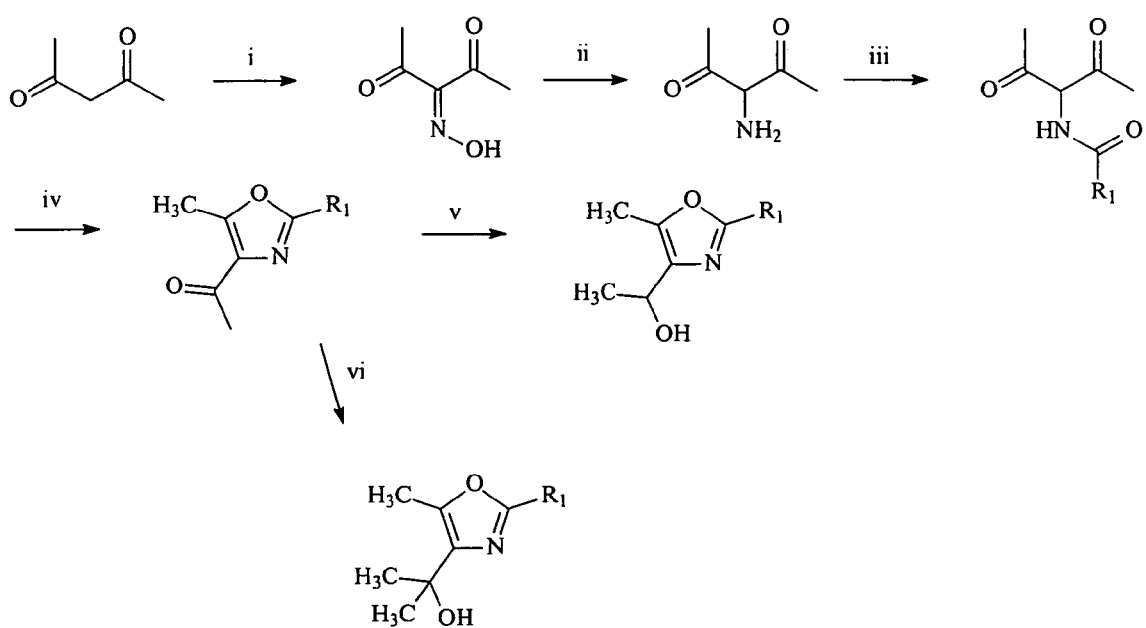
FIG. 8 shows how steric hindrance can be introduced under the form of methyl groups on the 4-methanol moiety. Starting from pentane-2,4-dione and following the same synthetic sequence as in FIG. 7 leads to the 4-acetyloxazole compounds which can be reduced by sodium borohydride to the 4-(1-ethyl)oxazole, or which can be transformed to 4-(2-hydroxy-2-propyl)oxazole with a methyl Grignard reagent such as methyl magnesium iodide.
Figure 9:
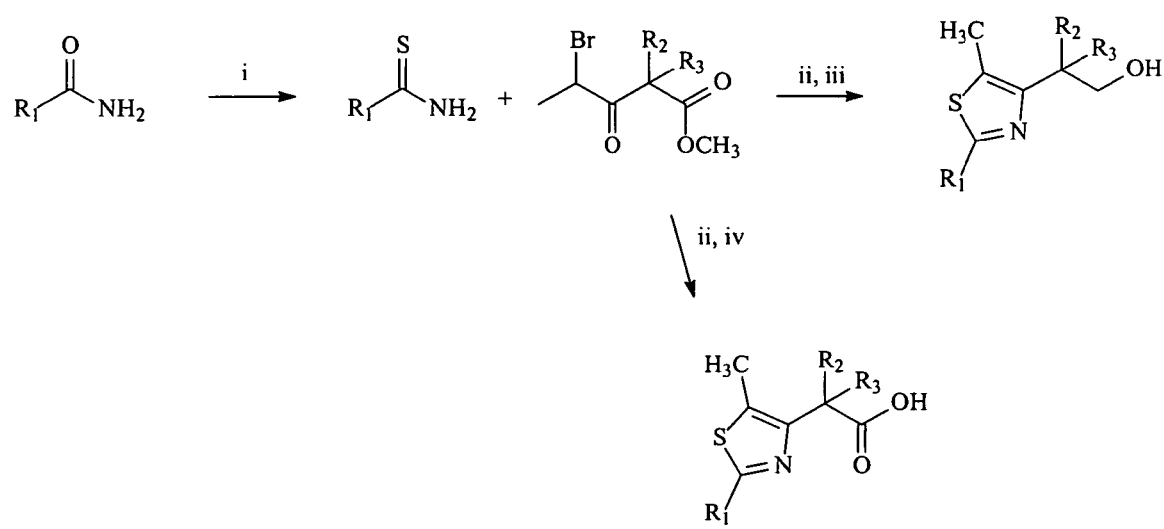
FIG. 9 illustrates an alternative synthetic scheme wherein condensation of a thioamide with methyl 4-bromo-3-oxo-pentanoate gives methyl 4-thiazoleacetate. Ester cleavage with lithium hydroxide or reduction with lithium aluminum hydride gives the corresponding acid or the alcohol, respectively.
Figure 10:
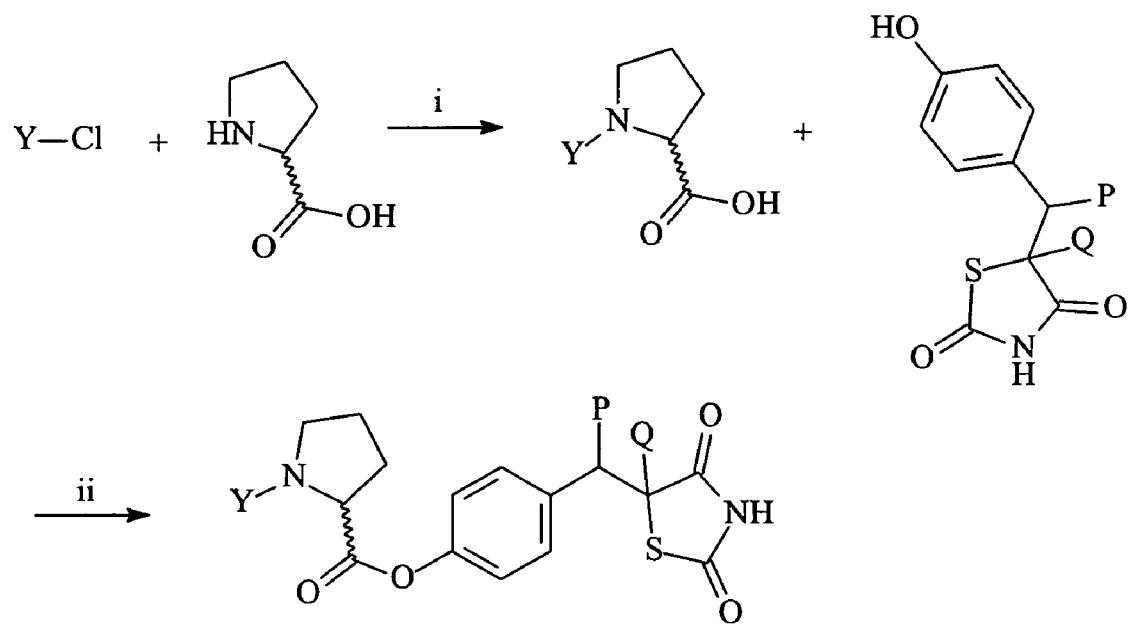
FIGS. 10–17 depict the synthesis of compounds 105 to 224 in Tables VI to XVII. These compounds contain an amino acid or an amino alcohol as part of their structure.
Figure 11:
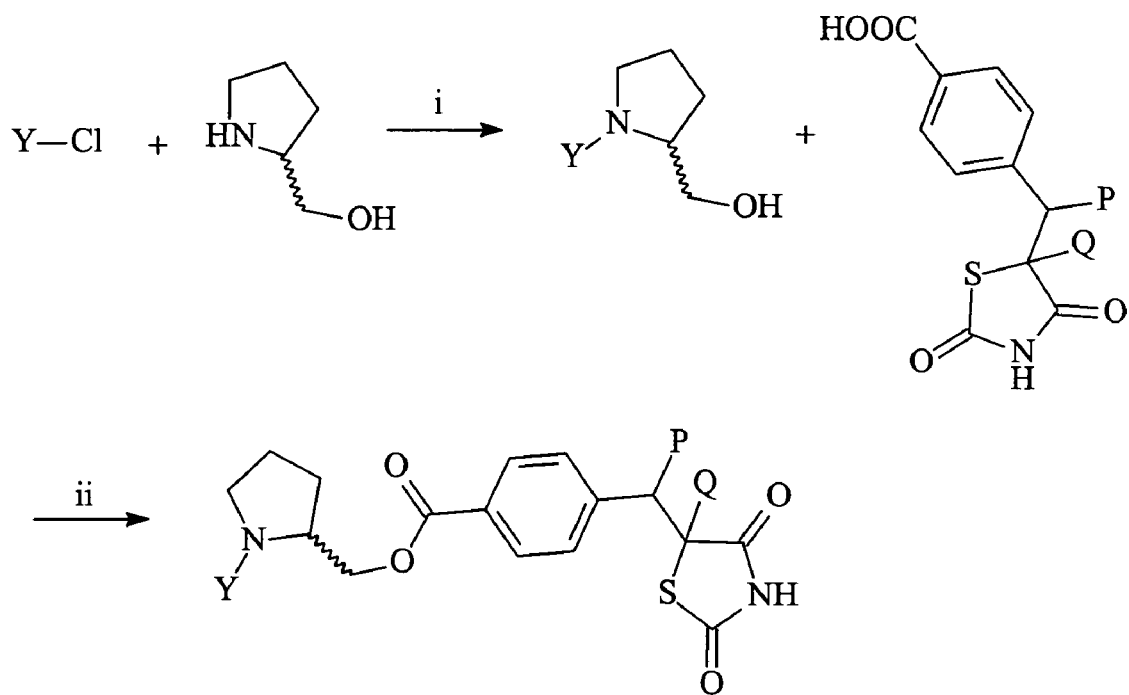
Figure 12:
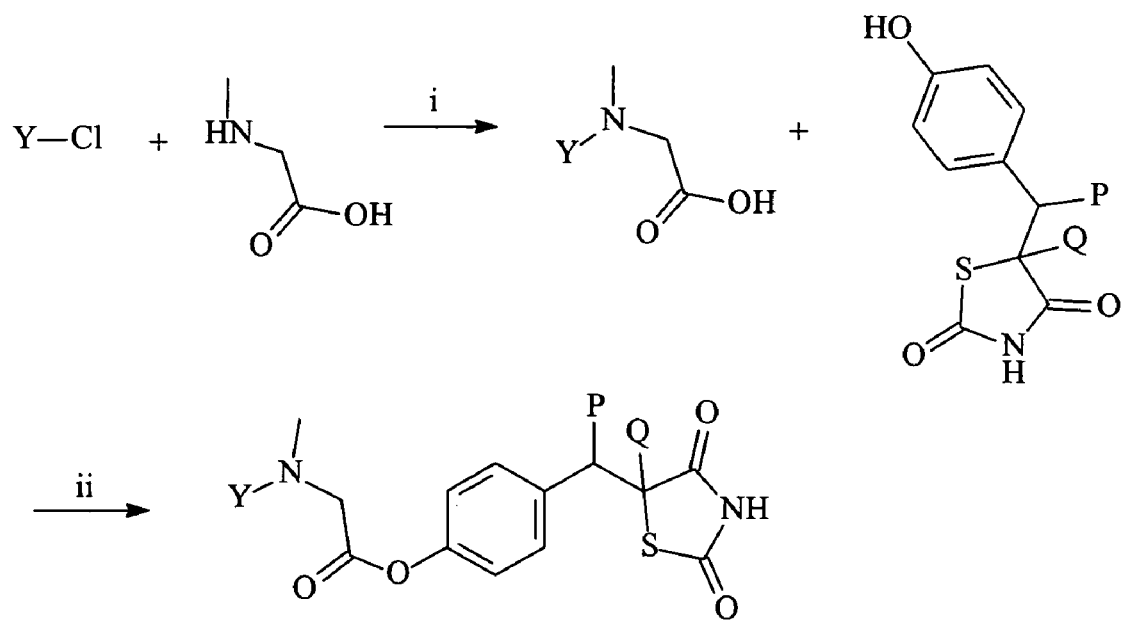
Figure 13:
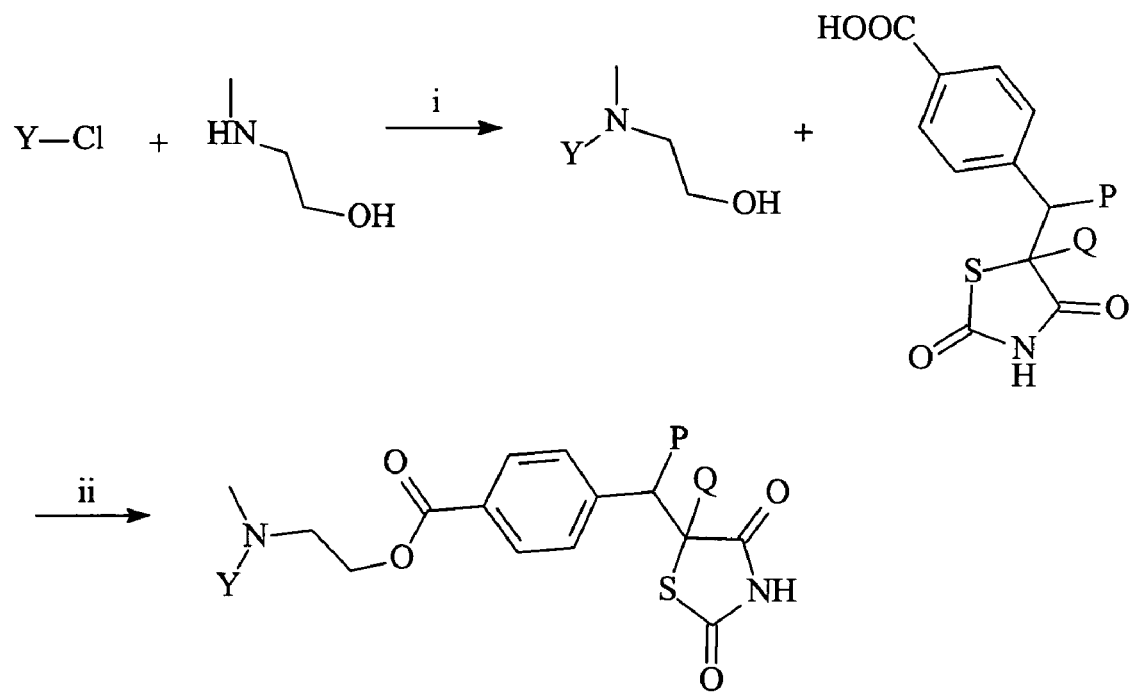
Figure 14:
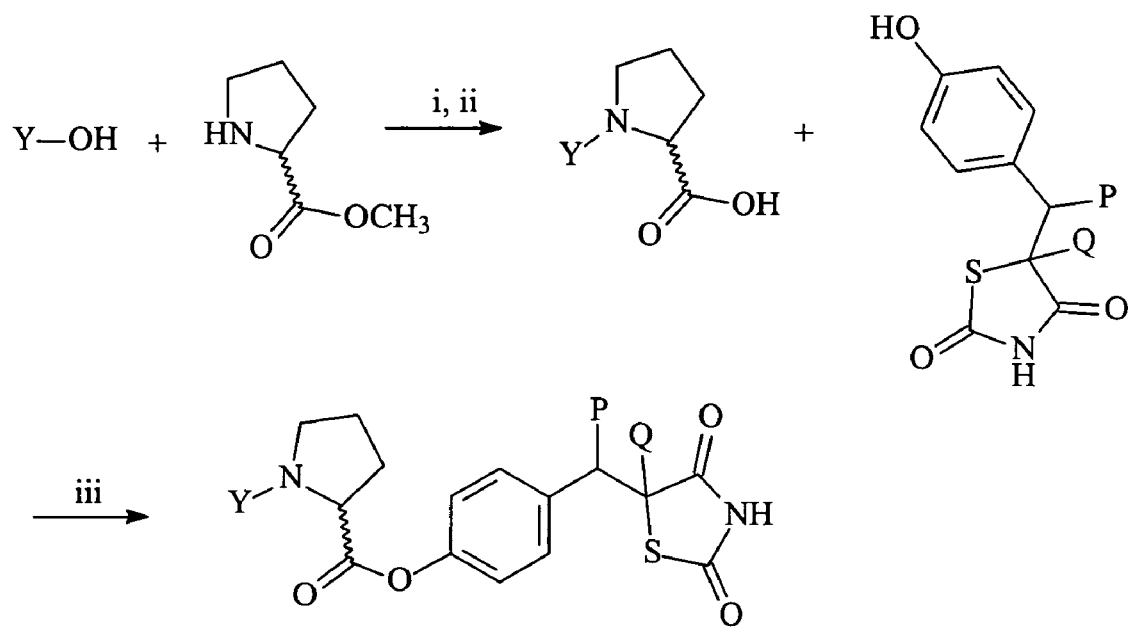

FIG. 8 shows how steric hindrance can be introduced under the form of methyl groups on the 4-methanol moiety. Starting from pentane-2,4-dione, following the same synthetic sequence as in FIG. 7 leads to the 4-acetyloxazole compounds which can be reduced by sodium borohydride to the 4-(1-ethyl)oxazole. Alternatively, the compounds can be transformed by methylmagnesium iodide into the tertiary alcohol analogs. In another embodiment, condensation of a thioamide with methyl 4-bromo-3-oxopentanoate gives methyl 4-thiazoleacetate, as described in FIG. 9. Ester cleavage with lithium hydroxide or reduction with lithium aluminum hydride gives the corresponding acid or the alcohol, respectively.

Compounds 105 to 224 in Tables VI to XVII all have an amino acid or an amino alcohol as part of their structure. Their synthesis is described in FIGS. 10 to 18. Any amino acid can be used in the synthesis of compounds according to this aspect of the invention. In certain embodiments, the amino acid group can be either proline or N-methyl glycine and the amino alcohol group is their alcohol equivalent, i.e., prolinol or N-methyl glycinol, respectively. As shown in FIGS. 10 to 13, the reaction of an alkyl chloride or a 2-heteroaryl chloride with proline, prolinol, N-methyl glycine, or N-methyl glycinol, in THF and triethylamine gives the corresponding N-alkyl or N-heteroaryl adduct, respectively. When these adducts are carboxylic acids, such as in FIGS. 10 and 12, they react with 5-(4-hydroxybenzyl) thiazolidine-2,4-dione in the presence of DCC and DMAP to give compounds 105–108, 111, 112, 125–128, 131, 132, 185–188, 191, 192. Carboxylic acid adducts react with 5-(4-hydroxybenzylidene)thiazolidine-2,4-dione in the presence of DCC and DMAP to give compounds 115–118, 121, 122, 135–138, 141, 142, 195–198, 201, 202. When these adducts are alcohols, such as in FIGS. 11 and 13, they react with 5-(4-carboxybenzyl)thiazolidine-2,4-dione in the presence of DCC and DMAP to give compounds 145–148, 151, 152, 165–168, 171, 172, 205–208, 211, 212. Alcohol adducts react with 5-(4-carboxybenzylidene)thiazolidine-2, 4-dione in the presence of DCC and DMAP to give compounds 155–158, 161, 162, 175–178, 181, 182, 215–218, 221, 222.

Alternatively, the amino acid or amino alcohol group can be linked to another group via an amide function, such as described in FIGS. 14 to 17. The synthesis of such compounds is straightforward. When the compounds contain an amino acid, as in FIGS. 14 and 16, the synthetic sequence is an amide bond formation, ester deprotection, and ester formation.

As an illustrative example, (R)-Trolox® is combined with L-proline methyl ester, in the presence of DCC and DMAP in methylene chloride to form an amide intermediate. The methyl ester of the proline group is then cleaved with lithium hydroxide in methanol, and the resulting carboxylic acid is combined with 5-(4-hydroxybenzyl)thiazolidine-2,4-dione in DCC/DMAP/methylene chloride to give compound 109. The (S)-isomer, compound 110, is made in a similar way. The same kind of synthetic scheme leads to compounds 113, 114, 119, 120, 123, 124, 129, 130, 133, 134, 139, 140, 143, 144, 189, 190, 193, 194, 199, 200, 203, and 204.

Figure 15:
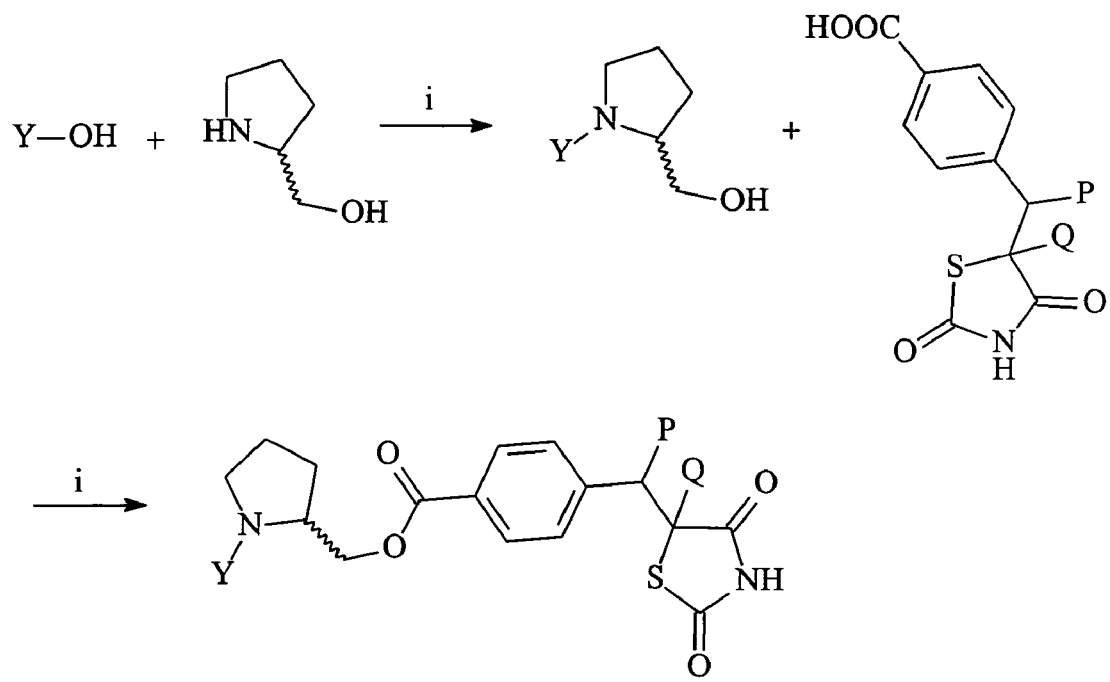
Figure 16:
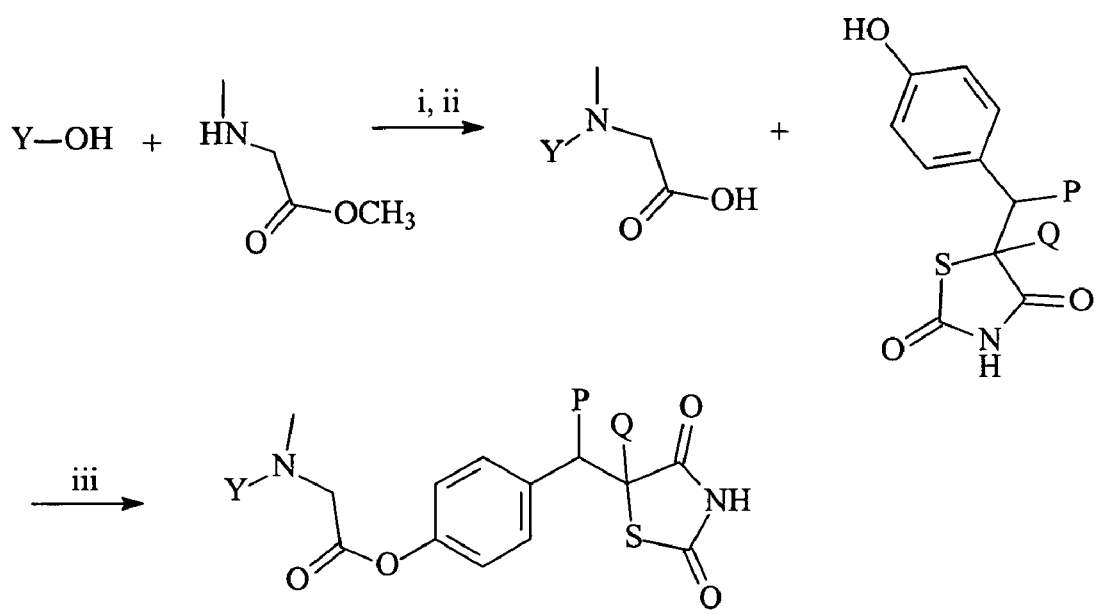
Figure 17:
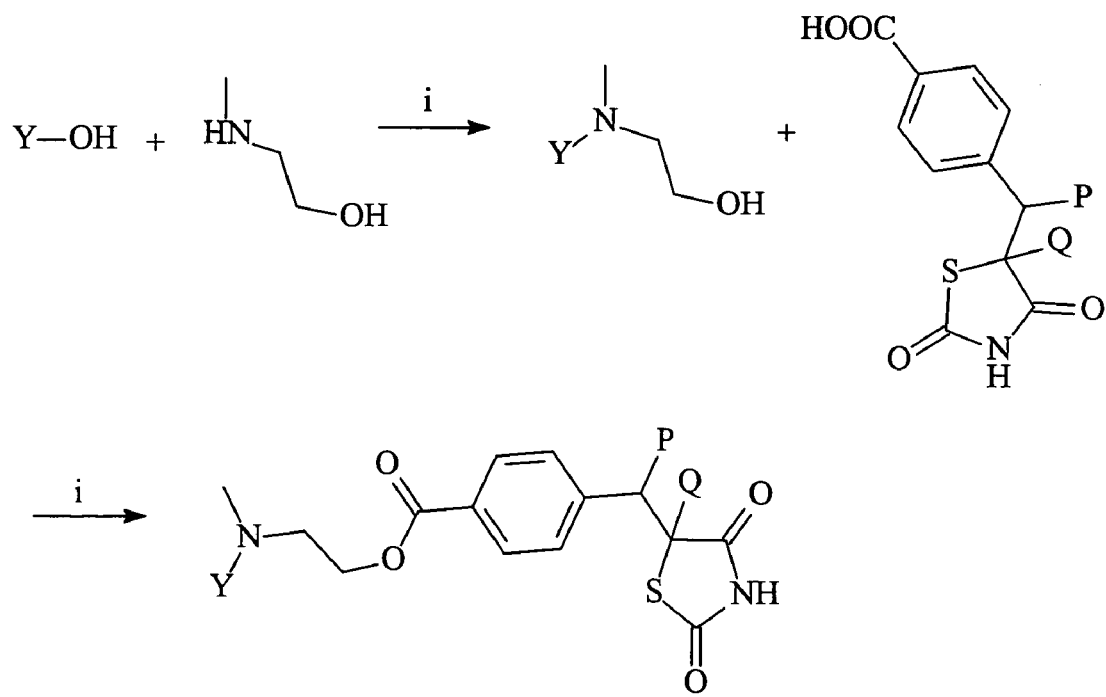
Figure 18:
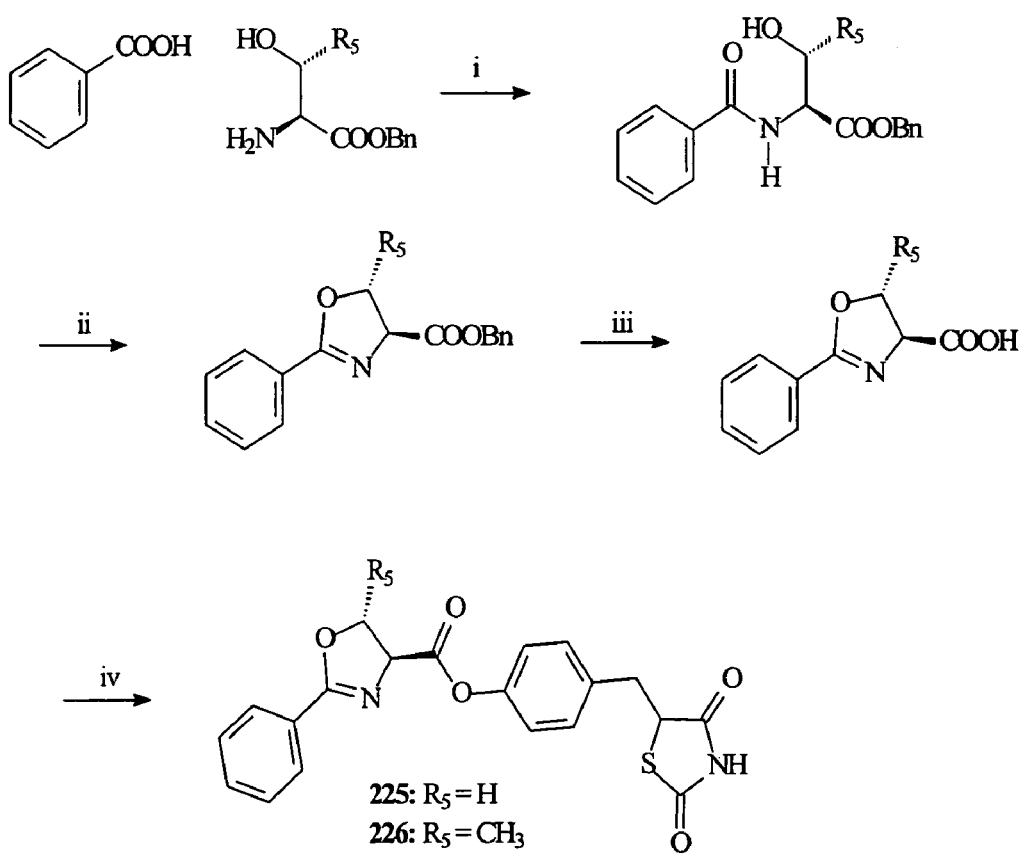
FIG. 18 provides an exemplary synthetic pathway for compounds 225 to 242 (Table XVIII). These compounds are oxazoline-4-carboxylic acid types of compounds. Their synthesis (FIG. 18) starts from serine ($R_5$=H) or from threonine ($R_5$=$CH_3$)benzyl ester. The ester is coupled with an alkyl or an arylcarboxylic acid using for example EDC as a coupling agent. The serine or threonine group then cyclizes into an oxazoline upon treatment with thionyl chloride. Coupling with 5-(4-hydroxybenzyl)thiazolidine-2,4-dione using DCC/DMAP/methylene chloride gives compounds 225 to 242.

When the compounds contain an amino alcohol, as in FIGS. 15 and 17, the synthetic sequence is an amide bond formation, followed by an ester bond formation. As an illustrative example, (R)-Trolox® is combined with L-prolinol in the presence of DCC and DMAP in methylene chloride to form an amide intermediate. The resulting amide is combined with 5-(4-carboxybenzyl)thiazolidine-2,4-dione in DCC/DMAP/methylene chloride to give compound 149. The (S)-isomer, compound 150, is made in a similar way. The same kind of synthetic scheme leads to compounds 153, 154, 159, 160, 163, 164, 169, 170, 173, 174, 179, 180, 183, 184, 209, 210, 213, 214, 219, 220, 223, and 224.

Compounds 225 to 242 (Table XVIII) are oxazoline-4-carboxylic acid types of compounds. Their synthesis (FIG. 18) starts from serine ($R_5$=H) or from threonine ($R_5$=$CH_3$) benzyl ester. The ester is coupled with an alkyl or an arylcarboxylic acid using for example EDC as a coupling agent. The serine or threonine group then cyclizes into an oxazoline upon treatment with thionyl chloride. Coupling with 5-(4-hydroxybenzyl)thiazolidine-2,4-dione using DCC/DMAP/methylene chloride gives compounds 225 to 242.

Compounds 243 to 248 (Table XIX) are thiazolidinedione molecules where X is a group containing a substituted 2-methyl-2-propionyl residue. Examples include the 2-methyl-2-(4-chlorophenoxy)propionyl moiety (clofibryl moiety), the 2-methyl-2-[4-(4-chlorobenzoyl)phenoxy]propionyl moiety (fenofibryl moiety), and 2,2-dimethyl-5-(2,5-xylyloxy)valeryl moiety (gemfibrozilyl moiety).

Compounds 249 to 252 (Table XX) are thiazolidinedione molecules where X is a group containing a substituted (R,R)-3,5-dihydroxyheptanoyl residue. Examples include the (βR, δR)-2-(4-fluorophenyl)-5-(1-methylethyl)-3-phenyl-4-[(phenyl-amino)carbonyl]1H-pyrrole-1-(β,δ,dihydroxy)heptanoyl group (atorvastatin), and the 1,2,3,7,8,8a-hexahydro-1-(2-methylbutanoyl)oxy-3,7-dimethylnaphthalenyl-8-[(3R,5R)-7-heptan]oyl group (lovastatin). The synthesis of these compounds proceeds as in the examples of Table I, (i.e., by a simple esterification procedure between the lipid-lowering agent and compound 1 or compound 2).

Compounds 253 to 260 (Table XXI) are thiazolidinedione molecules where X is a group containing an arylacetic acid residue, such as in molecules that have non-steroidal anti-inflammatory properties. In these examples, the X group is an ibuprofen, ibufenac, naproxen, diclofenac, or nabumetone residue. The synthesis of these compounds is a simple ester formation reaction between the X group and compound 1 (P and Q are hydrogen) or compound 2 (P and Q form a bond).

Compounds 261 to 268 (Table XXII) are thiazolidinedione molecules where X is a group containing a cortienic acid residue, such as in molecules that have glucocorticoid anti-inflammatory properties. In these examples, the X group is a cortienic acid, 1,2-dihydrocortienic acid, 6α, 9α-difluoro-1,2-dihydrocortienic acid, and a 9α-fluoro-16α-methyl-1,2-dihydrocortienic acid residue. The synthesis of these compounds is a simple ester formation reaction between the X group and compound 1 (P and Q are hydrogen) or compound 2 (P and Q form a bond). Cortienic acid, one of the many metabolites of hydrocortisone in man, can be synthetized from hydrocortisone by oxidation with sodium periodate. The substituted cortienic acid analogs can be made in an identical manner from the corresponding substituted glucocorticoids. This oxidation procedure is described in detail in [Druzgala P.: Novel Soft Anti-inflammatory Glucocorticoids for Topical Application. Ph.D. Dissertation (1985), University of Florida, Gainesville, Fla., hereby incorporated by reference in its entirety].

Figure 19:
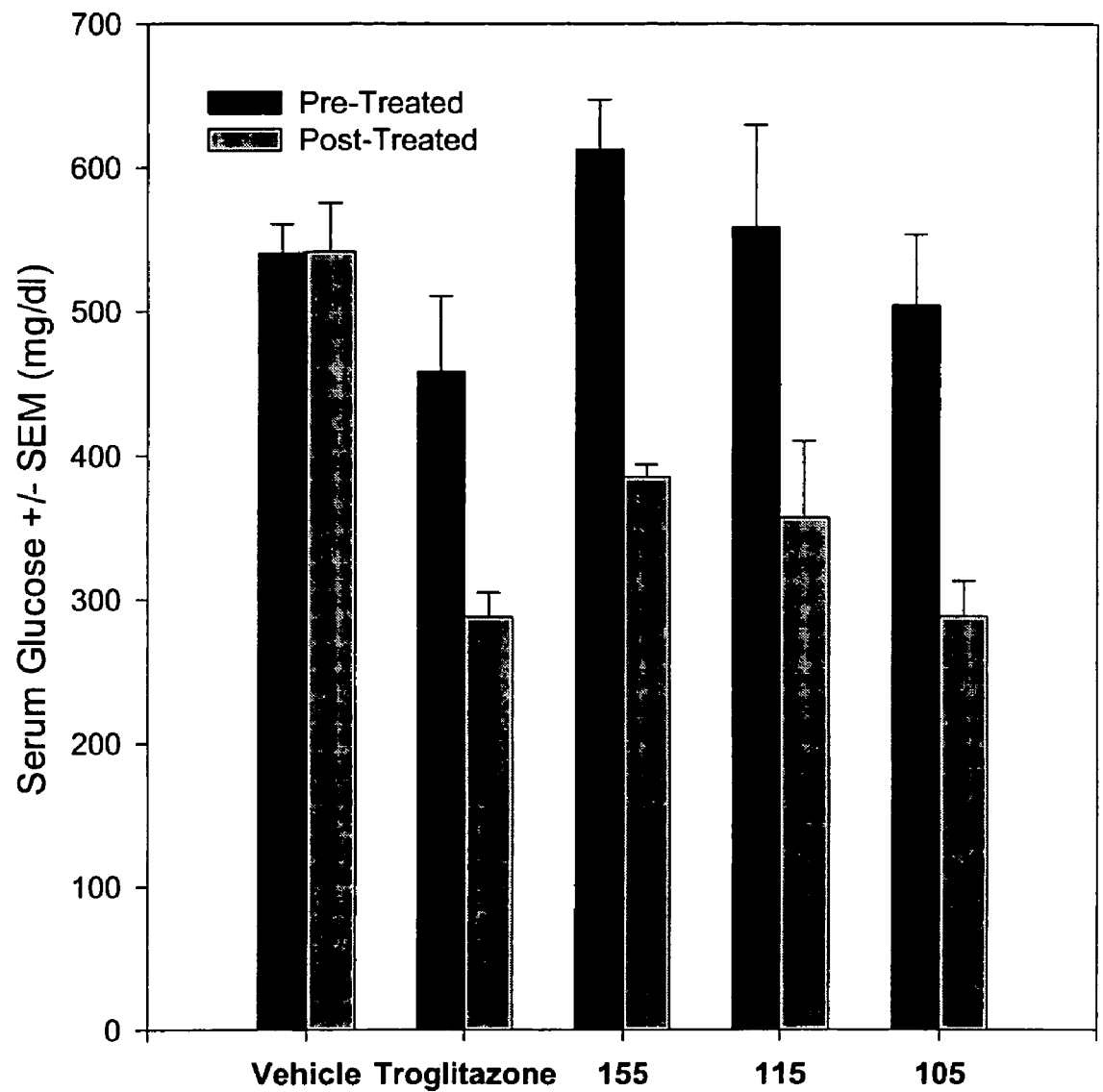
FIGS. 19–20 illustrate the activity of representative compounds on serum glucose and insulin levels in non-insulin dependent diabetic mellitus (NIDDM) KK-A$^y$ male mice. Post-treatment data for each group were transferred to a percentage of pretreatment values and unpaired Student's t test was used for comparison between vehicle and test substance treated groups. Results show a significant reduction of both serum glucose and serum insulin relative to the vehicle control group. Reduction in serum glucose and serum insulin levels were comparable to the reduction observed in the troglitazone-treated animals. The results are also presented in Table XXI.
Figure 20:
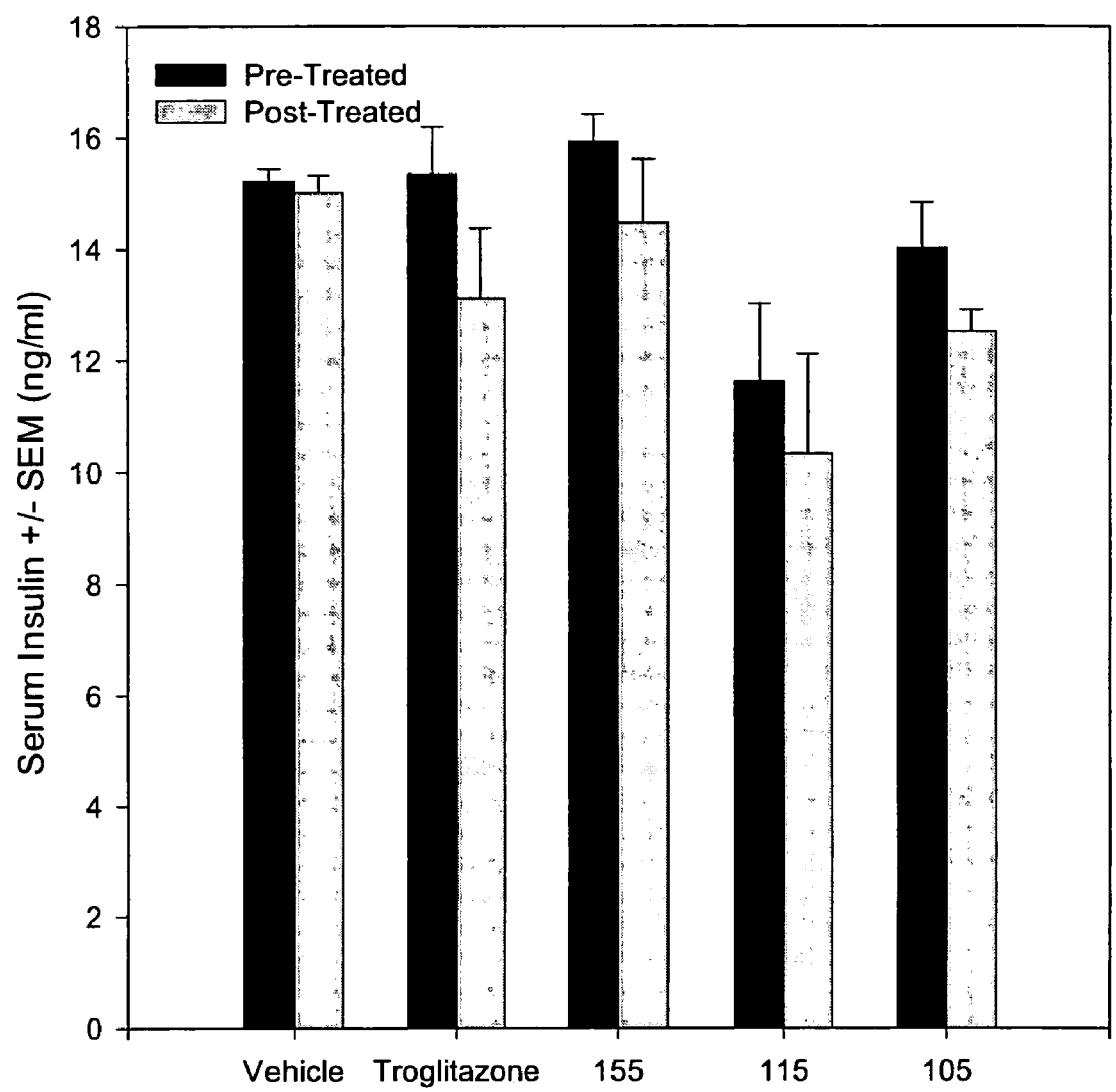

Representative compounds were chosen and evaluated for activity on serum glucose and insulin levels in non-insulin dependent diabetic mellitus (NIDDM) KK-$A_y$ male mice. Post-treatment data for each group were transferred to a percentage of pretreatment values and unpaired Student's t test was used for comparison between vehicle and test substance treated groups. Results show a significant reduction of both serum glucose and serum insulin relative to the vehicle control group. Reduction in serum glucose and serum insulin levels were comparable to the reduction observed in the troglitazone-treated animals. The results are presented in Table XXI and in FIGS. 19 and 20.

EXAMPLES

Example 1

To (S)-2-pyrrolidinemethanol (3.96 g) in THF (30 ml) is added 2-chlorobenzoxazole (5.90 g) also in THF (80 ml) and then, dropwise, triethylamine (3.96 g). Stir at 50° C. for 4 hours. Cool to room temperature and filter out the solid. Evaporate the solvent and dissolve the crude product in 5 ml of methylene chloride. Pass through a silica plug (50 g) in a fritted filter funnel, and elute with methanol/methylene chloride (10:90), applying suction until the product has been collected. The yield of (S)-1-(2-benzoxazolyl)-2-hydroxymethylpyrrolidine is 8.2 g.

Example 2

To (S)-2-pyrrolidinemethanol (3.96 g) in THF (30 ml) is added 2-chlorobenzothiazole (6.50 g) also in THF (80 ml) and then, dropwise, triethylamine (3.96 g). Stir at 50° C. for 4 hours. Cool to room temperature and filter out the solid. Evaporate the solvent and dissolve the crude product in 5 ml of methylene chloride. Pass through a silica plug (50 g) in a fritted filter funnel, and elute with methanol/methylene chloride (10:90), applying suction until the product has been collected. The yield of (S)-1-(2-benzothiazolyl)-2-hydroxymethylpyrrolidine is 8.8 g.

Example 3

To (R)-2-pyrrolidinemethanol (10.1 g) in THF (50 ml) is added 4,5-dimethylthiazole (14.8 g) also in THF (100 ml) and then, dropwise, triethylamine (10.1 g). Stir at 50° C. for 4 hours. Cool to room temperature and filter out the solid. Evaporate the solvent and dissolve the crude product in 10 ml of methylene chloride. Pass through a silica plug (100 g) in a fritted filter funnel, and elute with methanol/methylene chloride (10:90), applying suction until the product has been collected. The yield of (R)-1-(4,5-dimethyl-2-thiazolyl)-2-hydroxymethylpyrrolidine is 19.5 g.

Example 4

2-chloropyridine (12 g) and 2-(methylamino)ethanol (100 ml) are stirred under nitrogen at 120° C. for 18 hours. Cool to room temperature and then pour into iced water (250 ml). Extract with ethyl acetate (2×200 ml). Dry over sodium sulfate. Filter. Evaporate to dryness. The crude product is distilled in vacuo to give 10.3 g of N-methyl-N-(2-pyridinyl)-2-aminoethanol, boiling at 110° C./1.0 mmHg.

Example 5

A solution of 2-chlorobenzoxazole (15.3 g) in THF (100 ml) is added dropwise to an ice-cold solution of 2-(methylamino)ethanol (8.0 g) and triethylamine (10.1 g) also in THF (100 ml). The mixture is stirred at room temperature for 4 hours and the solid is filtered off. The solvent is evaporated and the residue is dissolved in methylene chloride and passed through a silica plug (100 g), eluting with methanol/methylene chloride (10:90) until the product has been collected. The yield of N-methyl-N-(2-benzoxazolyl)-2-aminoethanol is 15.7 g.

Example 6

Thionyl chloride (2.5 ml) was added dropwise to an ice-cold solution of (R)-6-hydroxy-2,5,7,8-tetramethylchroman-2-ylcarbinol (5.1 g) in anhydrous methylene chloride (50 ml). The solution was stirred at 0° C. for 1 hour and then at room temperature for another period of 2 hours. Wash with saturated sodium bicarbonate solution (2×25 ml), then with brine (25 ml), and then with water (25 ml). Dry over sodium sulfate, filter, and evaporate to dryness. The crude product, (R)-6-hydroxy-2,5,7,8-tetramethylchroman-2-ylmethyl chloride (5.2 g) is used as is in the next step.

Example 7

Thionyl chloride (2.5 ml) was added dropwise to an ice-cold solution of (S)-6-hydroxy-2,5,7,8-tetramethylchroman-2-ylcarbinol (5.1 g) in anhydrous methylene chloride (50 ml). The solution was stirred at 0° C. for 1 hour and then at room temperature for another period of 2 hours. Wash with saturated sodium bicarbonate solution (2×25 ml), then with brine (25 ml), and then with water (25 ml). Dry over sodium sulfate, filter, and evaporate to dryness. The crude product, (S)-6-hydroxy-2,5,7,8-tetramethylchroman-2-ylmethyl chloride (5.0 g) is used as is in the next step.

Example 8

A mixture of (R)-6-hydroxy-2,5,7,8-tetramethylchroman-2-ylmethyl chloride (8.43 g), triethylamine (2.6 g), and 2-(methylamino)ethanol (40 ml) is stirred at 120° C. under nitrogen for 16 hours. Cool to room temperature and pour into iced water (100 ml). Extract with ethyl acetate (3×100 ml) and wash the combined organic extracts with brine (100 ml). Dry over sodium sulfate. Filter. Evaporate to dryness. The product, (R)-2-[N-(6-hydroxy-2,5,7,8-tetramethylchroman-2-ylmethyl)-N-methylamino]ethanol weighs 9.0 g.

Example 9

A mixture of (S)-6-hydroxy-2,5,7,8-tetramethylchroman-2-ylmethyl chloride (8.43 g), triethylamine (2.6 g), and 2-(methylamino)ethanol (40 ml) is stirred at 120° C. under nitrogen for 16 hours. Cool to room temperature and pour into iced water (100 ml). Extract with ethyl acetate (3×100 ml) and wash the combined organic extracts with brine (100 ml). Dry over sodium sulfate. Filter. Evaporate to dryness. The product, (S)-2-[N-(6-hydroxy-2,5,7,8-tetramethylchroman-2-ylmethyl)-N-methylamino]ethanol weighs 8.9 g.

Example 10

A mixture of 2-chlorobenzoxazole (3.7 g), (L)-proline methyl ester, hydrochloride salt (4.0 g), and triethylamine (4.9 g) in anhydrous THF (50 ml) is stirred at room temperature for 18 hours. The solid is filtered off and washed with THF (10 ml). The solution is evaporated to dryness and the crude product is dissolved in methylene chloride (5 ml) and passed through a plug of silica (50 g), eluting with ethyl acetate/methylene chloride (10:90). The product, (L)-N-(2-benzoxazolyl)-proline methyl ester (5.0 g) is a crystalline solid.

Example 11

A mixture of 2-chlorobenzoxazole (3.7 g), (D)-proline methyl ester, hydrochloride salt (4.0 g), and triethylamine (4.9 g) in anhydrous THF (50 ml) is stirred at room temperature for 18 hours. The solid is filtered off and washed with THF (10 ml). The solution is evaporated to dryness and the crude product is dissolved in methylene chloride (5 ml) and passed through a plug of silica (50 g), eluting with ethyl acetate/methylene chloride (10:90). The product, (D)-N-(2-benzoxazolyl)-proline methyl ester (5.5 g) is a crystalline solid.

Example 12

(L)-N-(2-benzoxazolyl)-proline methyl ester (5.0 g) is suspended in a mixture consisting of methanol (50 ml), water (5 ml), and lithium hydroxide (0.5 g). Stir for 18 hours at room temperature. Acidify to pH 4.5 with citric acid. Extract with ethyl acetate (4×50 ml). Dry over sodium sulfate, filter, and evaporate to dryness. The product, (L)-N-(2-benzoxazolyl)-proline (4.3 g) is an off-white solid.

Example 13

A mixture of (L)-proline (4.6 g), 2-chlorobenzoxazole (6.6 g), and triethylamine (4.45 g) in anhydrous THF (100 ml) is stirred at reflux temperature for 18 hours. Cool down to room temperature, filter off the solid and wash it with a THF (10 ml). Evaporate the solvent. Add ethyl acetate (50 ml) and then 1N sodium hydroxide (50 ml). Stir for 5 minutes. Keep the aqueous phase. Wash again with ethyl acetate (50 ml). Acidify with citric acid to pH 4.5. Isolate the precipitate by filtration. The aqueous filtrate is extracted with ethyl acetate (4×30 ml). Dry over sodium sulfate. Filter. Evaporate to dryness. The solids are dried in vacuo at 35° C. for 18 hours. The first crop of product weighs 4.77 g. The second crop weighs 3.26 g. The total amount of product, (L)-N-(2-benzoxazolyl)-proline, is 8.03 g.

Example 14

A mixture of (D)-proline (4.6 g), 2-chlorobenzoxazole (6.6 g), and triethylamine (4.45 g) in anhydrous THF (100 ml) is stirred at reflux temperature for 18 hours. Cool down to room temperature, filter off the solid and wash it with a THF (10 ml). Evaporate the solvent. Add ethyl acetate (50 ml) and then 1N sodium hydroxide (50 ml). Stir for 5 minutes. Keep the aqueous phase. Wash again with ethyl acetate (50 ml). Acidify with citric acid to pH 4.5. Isolate the precipitate by filtration. The aqueous filtrate is extracted with ethyl acetate (4×30 ml). Dry over sodium sulfate. Filter. Evaporate to dryness. The solids are dried in vacuo at 35° C. for 18 hours. The first crop of product weighs 4.93 g. The second crop weighs 2.90 g. The total amount of product, (L)-N-(2-benzoxazolyl)-proline, is 7.83 g.

Example 15

A mixture of 4-hydroxybenzaldehyde (122.12 g), 2,4-thiazolidinedione (117.13 g), piperidine (5.11 g), and benzoic acid (6.11 g) in toluene (1,000 ml), is stirred at 80° C. for 16 hours. Cool to room temperature and filter off the yellow solid. Wash the solid with methylene chloride (3×100 ml) and then with methanol/methylene chloride (30:70) (2×100 ml). Dry in vacuo at 35° C. until constant weight. The yield of product, 5-(4-hydroxybenzylidene)-2,4-thiazolidinedione, is 217.8 g.

Example 16

To p-anisidine (25 g) in acetone (400 ml) at between 0 and 5° C., add dropwise a solution of sodium nitrite (15.41 g) in water (50 ml) and 12N hydrochloric acid (50 ml) from 2 different funnels over a 15-minute period. Stir for another 5 minutes at 0° C. Add methyl acrylate (104.9 g) and then warm up the solution to 35° C. Transfer into a 2-L Erlenmeyer flask and stir vigorously. While stirring, add copper(I) oxide (0.7 g) in several portions. Keep stirring for as long as nitrogen gas evolves from the solution, then stir for another 4 hours. Evaporate the organic solvent and dilute the aqueous residue with water (200 ml). Extract with methylene chloride (200 ml). Dry over sodium sulfate, filter, and evaporate to dryness. The product, methyl 2-chloro-3-(4-methoxyphenyl)propanoate, is a dark oil weighing 42.96 g.

Example 17

Methyl 2-chloro-3-(4-methoxyphenyl)propanoate (31.44 g), thiourea (16.89 g), and anhydrous sodium acetate (11.24 g) in 2-methoxyethanol (100 ml) is stirred at 100° C. for 4 hours. Cool to room temperature and place the flask at 4° C. for 16 hours. The pale yellow solid is filtered off and is washed with hexanes (50 ml). Stir for 30 minutes in ethyl acetate/water (100 ml:10 ml). Filter. Crystallize from hot ethanol (600 ml). After leaving at 4° C. for 16 hours, the crystals are filtered off and stirred at reflux for 8 hours in a mixture of 2-methoxyethanol (100 ml) and 2N hydrochloric acid (20 ml). Evaporate the solvent. Add ethyl acetate (200 ml) and water (200 ml). Keep the organic phase and wash again with water (200 ml). Dry over sodium sulfate, filter, evaporate to dryness. The product, 5-(4-methoxybenzyl) thiazolidine-2,4-dione (16.7 g) is an oil that solidifies upon standing.

Example 18

To a solution of 5-(4-methoxybenzyl)thiazolidine-2,4-dione (14.3 g) in anhydrous methylene chloride (100 ml) cooled to −40° C., add a 1.0M solution of boron tribromide in methylene chloride (63 ml). The solution is left to warm up to 23° C. and is then stirred for another 16 hours. Pour into iced water (700 ml) and stir for 15 minutes. Isolate the precipitate by filtration. Wash the product with water (50 ml) and then with methylene chloride (50 ml). The yield of 5-(4-hydroxybenzyl)thiazolidine-2,4-dione is 12.8 g.

Example 19

A mixture of methyl 4-formylbenzoate (164.16 g), 2,4-thiazolidinedione (117.13 g), piperidine (5.11 g), and benzoic acid (6.11 g) in toluene (1,000 ml), is stirred at 80° C. for 16 hours. Cool to room temperature and filter off the yellow solid. Wash the solid with methylene chloride (3×100 ml) and then with methanol/methylene chloride (30:70) (2×100 ml). Dry in vacuo at 35° C. until constant weight. The yield of product, 5-(4-carbomethoxybenzylidene)-2,4-thiazolidinedione, is 258.0 g.

Example 20

A suspension of 5-(4-carbomethoxybenzylidene)-2,4-thiazolidinedione (26.3 g) and magnesium turnings (24 g) in anhydrous methanol (300 ml) is stirred at 45° C. for 8 hours. Acidify to pH 5.0 with 6N HCl and then extract with methylene chloride (2×250 ml). Dry over sodium sulfate, filter, and evaporate to dryness. The crude product is chromatographed on silica gel (1,300 g), eluting with methanol/methylene chloride (02:98). The yield of 5-(4-carbomethoxybenzyl)-2,4-thiazolidinedione is 15.2 g.

Example 21

A suspension of 5-(4-carbomethoxybenzylidene)-2,4-thiazolidinedione (50 g) in 6N HCl (200 ml) is stirred at reflux for 4 hours. The mixture is cooled to 4° C. and the product is filtered off. The product is then washed with water (2×100 ml) and is dried in vacuo at 40° C. The yield of 5-(4-carboxybenzylidene)-2,4-thiazolidinedione is 45 g.

Example 22

A suspension of 5-(4-carbomethoxybenzyl)-2,4-thiazolidinedione (50 g) in 6N HCl (200 ml) is stirred at reflux for 4 hours. The mixture is cooled to 4° C. and the product is filtered off. The product is then washed with water (2×100 ml) and is dried in vacuo at 40° C. The yield of 5-(4-carboxybenzyl)-2,4-thiazolidinedione is 44 g.

Example 23

(R)-6-Hydroxy-2,5,7,8-tetramethylchroman-2-carboxylic acid (9.2 g) and 5-(4-hydroxybenzyl)thiazolidine-2,4-dione (8.3 g) are dissolved in methylene chloride (100 ml) and THF (50 ml). To this add dicyclohexylcarbodiimide (7.6 g) and DMAP (0.5 g), and then stir for 4 hours at room temperature. The solid is removed by filtration and is washed with a small amount of THF (20 ml). The solvent is removed and the solid residue is stirred with methylene chloride (100 ml) and left at 4° C. for 16 hours. The product is isolated by filtration and dried in vacuo at 23° C. The yield of 5-{4-[(R)-6-hydroxy-2,5,7,8-tetramethylchroman-2-carboxy]benzyl}thiazolidine-2,4-dione is 12.4 g.

Example 24

(S)-6-Hydroxy-2,5,7,8-tetramethylchroman-2-carboxylic acid (9.2 g) and 5-(4-hydroxybenzyl)thiazolidine-2,4-dione (8.3 g) are dissolved in methylene chloride (100 ml) and THF (50 ml). To this add dicyclohexylcarbodiimide (7.6 g) and DMAP (0.5 g), and then stir for 4 hours at room temperature. The solid is removed by filtration and is washed with a small amount of THF (20 ml). The solvent is removed and the solid residue is stirred with methylene chloride (100 ml) and left at 4° C. for 16 hours. The product is isolated by filtration and dried in vacuo at 23° C. The yield of 5-{4-[(S)-6-hydroxy-2,5,7,8-tetramethylchroman-2-carboxy]benzyl)}thiazolidine-2,4-dione is 13.3 g.

Example 25

(R)-6-Hydroxy-2,5,7,8-tetramethylchroman-2-carbinol (1.9 g) and 5-(4-carboxybenzyl)thiazolidine-2,4-dione (1.8 g) are dissolved in methylene chloride (20 ml) and THF (10 ml). To this add dicyclohexylcarbodiimide (1.6 g) and DMAP (0.1 g), and then stir for 4 hours at room temperature. The solid is removed by filtration and is washed with a small amount of THF (5 ml). The solvent is removed and the solid residue is stirred with methylene chloride (20 ml) and left at 4° C. for 16 hours. The product is isolated by filtration and dried in vacuo at 23° C. The yield of 5-{4-[(R)-6-hydroxy-2,5,7,8-tetramethylchroman-2-methoxy] benzyl}thiazolidine-2,4-dione is 2.54 g.

Example 26

(S)-6-Hydroxy-2,5,7,8-tetramethylchroman-2-carbinol (1.9 g) and 5-(4-carboxybenzyl)thiazolidine-2,4-dione (1.8 g) are dissolved in methylene chloride (20 ml) and THF (10 ml). To this add dicyclohexylcarbodiimide (1.6 g) and DMAP (0.1 g), and then stir for 4 hours at room temperature. The solid is removed by filtration and is washed with a small amount of THF (5 ml). The solvent is removed and the solid residue is stirred with methylene chloride (20 ml) and left at 4° C. for 16 hours. The product is isolated by filtration and dried in vacuo at 23° C. The yield of 5-{4-[(S)-6-hydroxy-2,5,7,8-tetramethylchroman-2-methoxy] benzyl}thiazolidine-2,4-dione is 2.17 g.

Example 27

(R)-6-Hydroxy-2,5,7,8-tetramethylchroman-2-carboxylic acid (4.6 g) and 5-(4-hydroxybenzylidene)thiazolidine-2,4- dione (4.2 g) are dissolved in methylene chloride (50 ml) and THF (25 ml). To this add dicyclohexylcarbodiimide (3.8 g) and DMAP (0.25 g), and then stir for 4 hours at room temperature. The solid is removed by filtration and is washed with a small amount of THF (10 ml). The solvent is removed and the solid residue is stirred with methylene chloride (50 ml) and left at 4° C. for 16 hours. The product is isolated by filtration and dried in vacuo at 23° C. The yield of 5-{4-[(R)-6-hydroxy-2,5,7,8-tetramethylchroman-2-carboxy]benzylidene}thiazolidine-2,4-dione is 5.9 g.

Example 28

(S)-6-Hydroxy-2,5,7,8-tetramethylchroman-2-carboxylic acid (4.6 g) and 5-(4-hydroxybenzylidene)thiazolidine-2,4-dione (4.2 g) are dissolved in methylene chloride (50 ml) and THF (25 ml). To this add dicyclohexylcarbodiimide (3.8 g) and DMAP (0.25 g), and then stir for 4 hours at room temperature. The solid is removed by filtration and is washed with a small amount of THF (10 ml). The solvent is removed and the solid residue is stirred with methylene chloride (50 ml) and left at 4° C. for 16 hours. The product is isolated by filtration and dried in vacuo at 23° C. The yield of 5-{4-[(S)-6-hydroxy-2,5,7,8-tetramethylchroman-2-carboxy]benzylidene}thiazolidine-2,4-dione is 6.2 g.

Example 29

(R)-6-Hydroxy-2,5,7,8-tetramethylchroman-2-carbinol (3.8 g) and 5-(4-carboxybenzylidene)thiazolidine-2,4-dione (3.6 g) are dissolved in methylene chloride (40 ml) and THF (20 ml). To this add dicyclohexylcarbodiimide (3.2 g) and DMAP (0.2 g), and then stir for 4 hours at room temperature. The solid is removed by filtration and is washed with a small amount of THF (10 ml). The solvent is removed and the solid residue is stirred with methylene chloride (40 ml) and left at 4° C. for 16 hours. The product is isolated by filtration and dried in vacuo at 23° C. The yield of 5-{4-[(R)-6-hydroxy-2,5,7,8-tetramethylchroman-2-methoxy]benzylidene}thiazolidine-2,4-dione is 5.4 g.

Example 30

(S)-6-Hydroxy-2,5,7,8-tetramethylchroman-2-carbinol (3.8 g) and 5-(4-carboxybenzylidene)thiazolidine-2,4-dione (3.6 g) are dissolved in methylene chloride (40 ml) and THF (20 ml). To this add dicyclohexylcarbodiimide (3.2 g) and DMAP (0.2 g), and then stir for 4 hours at room temperature. The solid is removed by filtration and is washed with a small amount of THF (10 ml). The solvent is removed and the solid residue is stirred with methylene chloride (40 ml) and left at 4° C. for 16 hours. The product is isolated by filtration and dried in vacuo at 23° C. The yield of 5-{4-[(S)-6-hydroxy-2,5,7,8-tetramethylchroman-2-methoxy]benzylidene}thiazolidine-2,4-dione is 5.2 g.

Example 31

(L)-N-(2-benzoxazolyl)-proline (3.26 g) and 5-(4-hydroxybenzyl)thiazolidine-2,4-dione (3.11 g) are suspended in methylene chloride (100 ml). Add DCC (2.89 g) and DMAP (0.12 g) and stir at room temperature for 4 hours. Filter and purify on 114 g of silica, eluting with methanol/methylene chloride (02:98). The yield of 5-{4-[(S)-1-(2-benzoxazolyl)pyrrolidne-2-carboxy]benzyl}thiazolidine-2,4-dione is 4.55 g.

Example 32

(L)-1-(2-benzoxazolyl)pyrrolidine-2-carbinol (3.26 g) and 5-(4-carboxybenzyl)thiazolidine-2,4-dione (3.25 g) are suspended in methylene chloride (100 ml). Add DCC (2.88 g) and DMAP (0.12 g) and stir at room temperature for 4 hours. Filter and purify on 132 g of silica, eluting with methanoumethylene chloride (02:98). The yield of 5-{4-[(S)-1-(2-benzoxazolyl)pyrrolidinyl-2-methoxycarbonyl]benzyl}-thiazolidine-2,4-dione is 4.68 g.

Example 33

(D)-1-(2-benzoxazolyl)pyrrolidine-2-carbinol (3.26 g) and 5-(4-carboxybenzylidene)thiazolidine-2,4-dione (3.35 g) are suspended in methylene chloride (100 ml). Add DCC (2.91 g) and DMAP (0.12 g) and stir at room temperature for 4 hours. Filter and purify on 108 g of silica, eluting with methanol/methylene chloride (02:98). The yield of 5-{4-[(R)-1-(2-benzoxazolyl)pyrrolidinyl-2-methoxycarbonyl]benzylidene}-thiazolidine-2,4-dione is 4.32 g.

Example 34

(D)-1-(2-benzoxazolyl)pyrrolidine-2-carbinol (3.26 g) and 5-(4-carboxybenzyl)thiazolidine-2,4-dione (3.25 g) are suspended in methylene chloride (100 ml). Add DCC (2.93 g) and DMAP (0.12 g) and stir at room temperature for 4 hours. Filter and purify on 162 g of silica, eluting with methanoumethylene chloride (02:98). The yield of 5-{4-[(S)-1-(2-benzoxazolyl)pyrrolidinyl-2-methoxycarbonyl]benzyl}-thiazolidine-2,4-dione is 4.77 g.

Example 35

Triethylamine (8.3 ml) is added dropwise to a stirred cold solution of ethyl 2-aminoacetoacetate hydrochloride (5.4 g) and 4-methoxybenzoyl chloride (5.2 g) in dichloromethane (100 ml). After stirring for 3 hours, the solution is washed with water (100 ml), dried over sodium sulfate, filtered, and evaporated to dryness. The crude product, ethyl 2-(4-methoxy)phenylaminoacetoacetate weighs 6.7 g.

Example 36

Ethyl 2-(4-methoxy)phenylaminoacetoacetate (5.9 g) and phosphorus oxychloride (50 ml) are stirred at 10° C. for 30 minutes. The phosphorus oxychloride is removed by evaporation, and the residue is diluted with aqueous sodium bicarbonate and extracted with methylene chloride. After drying over sodium sulfate, the solution is evaporated and the product is crystallized from hexane, giving ethyl 5-methyl-2-(4-methoxy)phenyl-4-oxazolecarboxylate (4.5 g).

Example 37

A solution of benzoyl chloride (17 g) in ethyl acetate (40 ml) is added dropwise, with stirring, in an ice-cold mixture of L-serine methyl ester, hydrochloride (15.5 g), water (100 ml), sodium bicarbonate (21.8 g), and ethyl acetate (100 ml). After stirring for 2 hours, the organic phase is separated, dried over sodium sulfate, and evaporated to give crystalline N-benzoyl-L-serine methyl ester (22.0 g).

Example 38

A stirred mixture of N-benzoyl-L-serine methyl ester (21.0 g), thionyl chloride (21.0 g), and methylene chloride (150 ml) is stirred at reflux for 1 hour. The solvent is evaporated and the residue is diluted with cold water. Neutralize with sodium bicarbonate, and extract with ethyl acetate. Purification on silica gel (250 g), eluting with methanol:methylene chloride (01:99), yields methyl (S)-2-phenyl-2-oxazoline-4-carboxylate (15.2 g).

Example 39

A solution of benzoyl chloride (17 g) in ethyl acetate (40 ml) is added dropwise, with stirring, in an ice-cold mixture of L-threonine methyl ester, hydrochloride (16.5 g), water (100 ml), sodium bicarbonate (21.8 g), and ethyl acetate (100 ml). After stirring for 2 hours, the organic phase is separated, dried over sodium sulfate, and evaporated to give crystalline N-benzoyl-L-threonine methyl ester (21.5 g).

Example 40

A stirred mixture of N-benzoyl-L-threonine methyl ester (21.0 g), thionyl chloride (21.0 g), and methylene chloride (150 ml) is stirred at reflux for 1 hour. The solvent is evaporated and the residue is diluted with cold water. Neutralize with sodium bicarbonate, and extract with ethyl acetate. Purification on silica gel (250 g), eluting with methanol:methylene chloride (01:99), yields methyl (R,S)-2-phenyl-2-oxazoline-5-methyl-4-carboxylate (14.8 g).

Example 41

Activity in NIDDM KK-$A^y$ male mice. Non-inslin dependent diabetic mellitus male mice, weighing 50+/−5 g (9–10 weeks of age) were used. These animals exhibited hyperinsulinemia, hyperglycemia, and islet atrophy. The test compounds 105, 115, and 155, and the positive control compound troglitazone were suspended in a 1% carboxymethylcellulose preparation and were given orally at a dose of 10 mg/kg, twice a day, for 5 consecutive days. Blood sampling was performed before the first dose and then 90 minutes after the last dose. Serum glucose and insulin levels were measured. Percent reduction of serum glucose and insulin levels relative to the pre-treatment values are shown in Table XXIII and FIGS. 19 and 20.

It should be understood that the reaction schemes and embodiments described herein are for illustrative purposes only and that various modifications or changes in light thereof will be suggested to persons skilled in the art and are to be included within the spirit and purview of this application and the scope of the appended claims.

TABLE I

Formula I

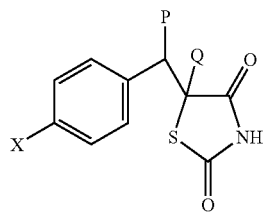

Com-

| pound number | X | P and Q* |
|---|---|---|
| 1 | HO— | H |
| 2 |  | db |
| 3 | HO-C(=O)- | H |
| 4 |  | db |
| 5 | cyclohexyl-C(CH₃)(C(=O)OCH₃)- | H |
| 6 |  | db |
| 7 | H₃C-pyridyl-CH₂-C(=O)-OCH₃ | H |
| 8 |  | db |
| 9 | chroman (H₃C, H₃C, HO, CH₃ substituents, CO₂CH₃) | H |
| 10 |  | db |
| 11 | chroman (H₃C, H₃C, HO, CH₃, CH₃ substituents, CO₂CH₃) | H |
| 12 |  | db |
| 13 | benzofuran (H₃C, H₃C, HO, CH₃ substituents, CH₃, CH₃, CO₂CH₃) | H |
| 14 |  | db |

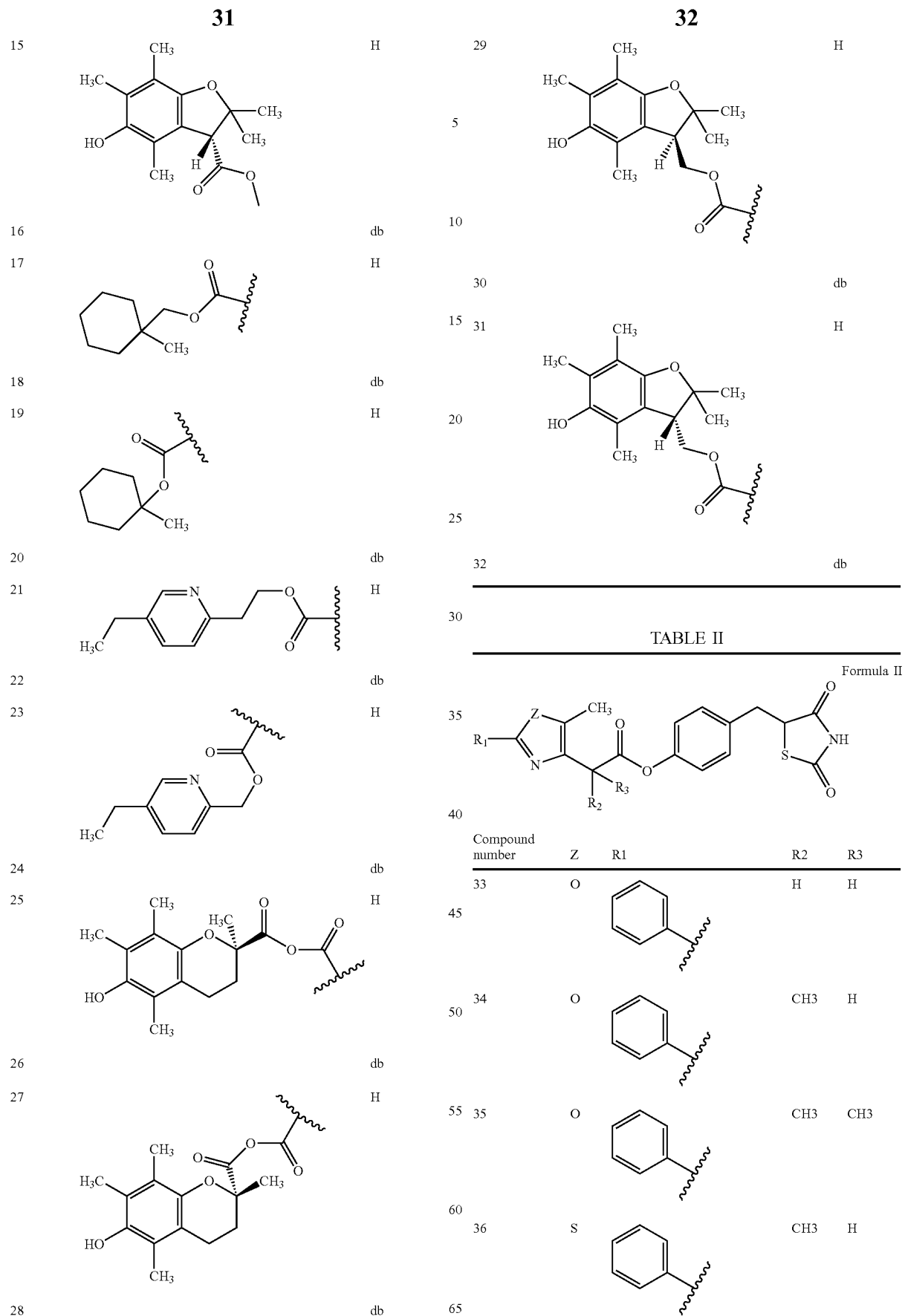

TABLE II-continued

Formula II

| Compound number | Z | R1 | R2 | R3 |
|---|---|---|---|---|
| 37 | O | 4-F-phenyl | CH3 | H |
| 38 | S | 4-F-phenyl | CH3 | H |
| 39 | O | 4-H3CO-phenyl | CH3 | H |
| 40 | S | 4-H3CO-phenyl | CH3 | H |
| 41 | O | 3-CH3-thiophen-2-yl | CH3 | H |
| 42 | S | 3-CH3-thiophen-2-yl | CH3 | H |
| 43 | O | 5-CH3-thiophen-2-yl | H | H |
| 44 | O | 5-CH3-thiophen-2-yl | CH3 | H |
| 45 | S | 5-CH3-thiophen-2-yl | H | H |
| 46 | O | 5-CH3-1,3,4-oxadiazol... (5-methyl-1,3,4-thiadiazol/oxadiazol) | CH3 | H |
| 47 | S | 5-CH3-1,3,4-oxadiazol... | H | H |
| 48 | O | pyridin-2-yl | CH3 | H |
| 49 | O | pyridin-4-yl | CH3 | H |
| 50 | O | pyrazin-2-yl | CH3 | H |

TABLE III

Formula II

| Compound number | Z | R1 | R2 | R3 |
|---|---|---|---|---|
| 51 | O | phenyl | H | H |
| 52 | O | phenyl | CH3 | H |

TABLE III-continued

[Structure: R1-Z-thiazole(CH3)-CH(R2)(R3)-C(=O)-O-C6H4-CH=C(thiazolidine-2,4-dione)]

| Compound number | Z | R1 | R2 | R3 |
|---|---|---|---|---|
| 53 | O | phenyl | CH3 | CH3 |
| 54 | S | phenyl | CH3 | H |
| 55 | O | 4-F-phenyl | CH3 | H |
| 56 | S | 4-F-phenyl | CH3 | H |
| 57 | O | 4-H3CO-phenyl | CH3 | H |
| 58 | S | 4-H3CO-phenyl | CH3 | H |
| 59 | O | 3-methylthiophen-2-yl | CH3 | H |
| 60 | S | 3-methylthiophen-2-yl | CH3 | H |
| 61 | O | 5-methylthiophen-2-yl | H | H |
| 62 | O | 5-methylthiophen-2-yl | CH3 | H |
| 63 | S | 5-methylthiophen-2-yl | H | H |
| 64 | O | 5-methyl-1,3,4-oxathiazol-2-yl | CH3 | H |
| 65 | S | 5-methyl-1,3,4-oxathiazol-2-yl | H | H |
| 66 | O | pyridin-2-yl | CH3 | H |
| 67 | O | pyridin-4-yl | CH3 | H |
| 68 | O | pyrazin-2-yl | CH3 | H |

TABLE IV

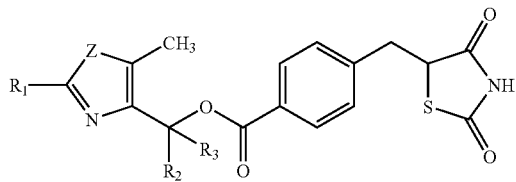

| Compound number | Z | R1 | R2 | R3 |
|---|---|---|---|---|
| 69 | O | phenyl | H | H |
| 70 | O | phenyl | CH3 | H |
| 71 | O | phenyl | CH3 | CH3 |
| 72 | S | phenyl | CH3 | H |
| 73 | O | 4-F-phenyl | CH3 | H |
| 74 | S | 4-F-phenyl | CH3 | H |
| 75 | O | 4-H3CO-phenyl | CH3 | H |
| 76 | S | 4-H3CO-phenyl | CH3 | H |
| 77 | O | 3-methylthiophen-2-yl | CH3 | H |

TABLE IV-continued

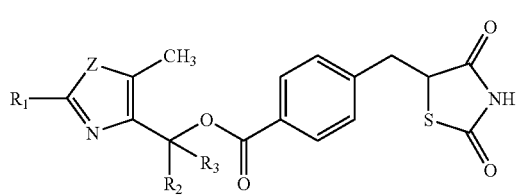

| Compound number | Z | R1 | R2 | R3 |
|---|---|---|---|---|
| 78 | S | 3-methylthiophen-2-yl | CH3 | H |
| 79 | O | 5-methylthiophen-2-yl | H | H |
| 80 | O | 5-methylthiophen-2-yl | CH3 | H |
| 81 | S | 5-methylthiophen-2-yl | H | H |
| 82 | O | 5-methyl-1,3,4-oxadiazol-2-yl (S) | CH3 | H |
| 83 | S | 5-methyl-1,3,4-oxadiazol-2-yl (S) | H | H |
| 84 | O | pyridin-2-yl | CH3 | H |
| 85 | O | pyridin-4-yl | CH3 | H |
| 86 | O | pyrazin-2-yl | CH3 | H |

TABLE V

| Compound number | Z | R1 | R2 | R3 |
|---|---|---|---|---|
| 87 | O | phenyl | H | H |
| 88 | O | phenyl | CH3 | H |
| 89 | O | phenyl | CH3 | CH3 |
| 90 | S | phenyl | CH3 | H |
| 91 | O | 4-F-phenyl | CH3 | H |
| 92 | S | 4-F-phenyl | CH3 | H |
| 93 | O | 4-H3CO-phenyl | CH3 | H |
| 94 | S | 4-H3CO-phenyl | CH3 | H |
| 95 | O | 3-methylthiophen-2-yl | CH3 | H |

TABLE V-continued

| Compound number | Z | R1 | R2 | R3 |
|---|---|---|---|---|
| 96 | S | 3-methylthiophen-2-yl | CH3 | H |
| 97 | O | 5-methylthiophen-2-yl | H | H |
| 98 | O | 5-methylthiophen-2-yl | CH3 | H |
| 99 | S | 5-methylthiophen-2-yl | H | H |
| 100 | O | 5-methyl-1,3,4-oxathiadiazol-2-yl | H3 | H |
| 101 | S | 5-methyl-1,3,4-oxathiadiazol-2-yl | H | H |
| 102 | O | pyridin-2-yl | CH3 | H |
| 103 | O | pyridin-4-yl | CH3 | H |
| 104 | O | pyrazin-2-yl | CH3 | H |

TABLE VI
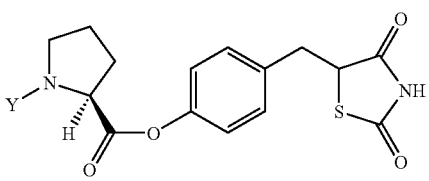
| Compound number | Y |
|---|---|
| 105 | 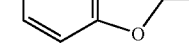 |
| 106 | 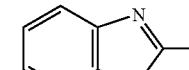 |
| 107 | 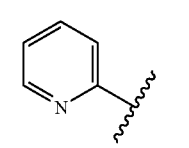 |
| 108 | 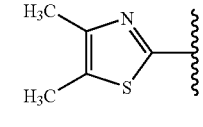 |
| 109 | 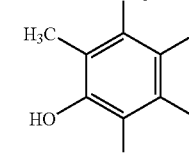 |
| 110 | 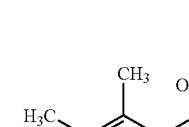 |
| 111 | 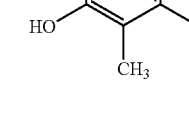 |
TABLE VI-continued
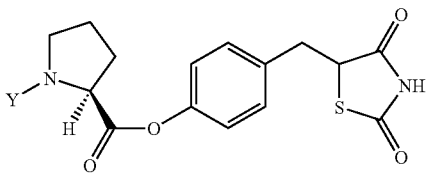
| Compound number | Y |
|---|---|
| 112 | 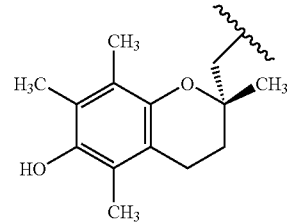 |
| 113 | 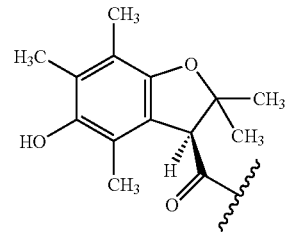 |
| 114 | 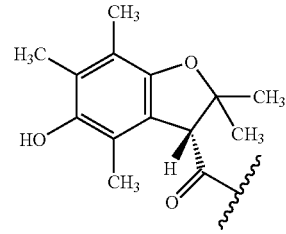 |
TABLE VII
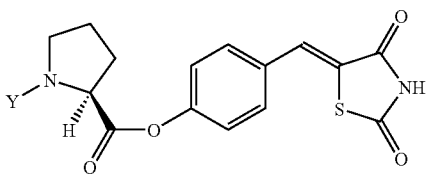
| Compound number | Y |
|---|---|
| 115 |  |
| 116 |  |

TABLE VII-continued
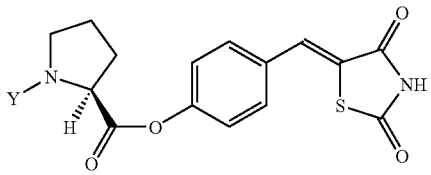
| Compound number | Y |
|---|---|
| 117 | 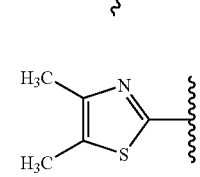 |
| 118 | 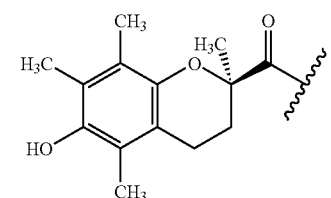 |
| 119 | 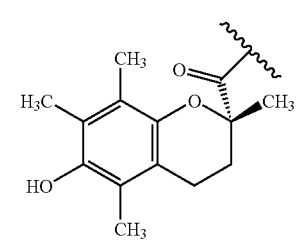 |
| 120 | 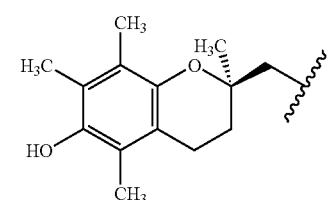 |
| 121 | 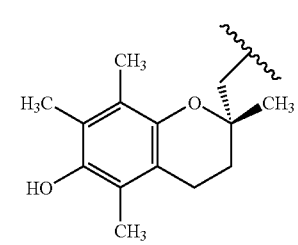 |
| 122 | 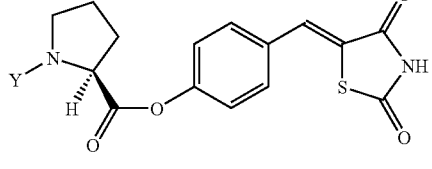 |
TABLE VII-continued
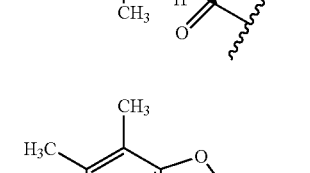
| Compound number | Y |
|---|---|
| 123 | 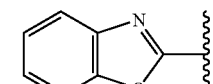 |
| 124 | 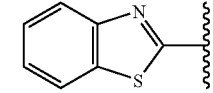 |
TABLE VIII
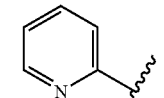
| Compound number | Y |
|---|---|
| 125 | 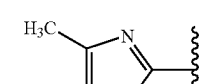 |
| 126 | 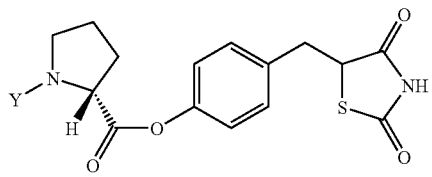 |
| 127 | 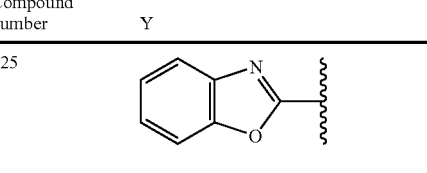 |
| 128 | 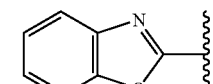 |

TABLE VIII-continued

[Structure: Pyrrolidine-N-Y with carboxylate ester to para-substituted benzyl-thiazolidine-2,4-dione]

| Compound number | Y |
|---|---|
| 129 | 2,5,7,8-tetramethyl-6-hydroxychroman-2-yl carbonyl (2R) |
| 130 | 2,5,7,8-tetramethyl-6-hydroxychroman-2-yl carbonyl (2S) |
| 131 | 2,5,7,8-tetramethyl-6-hydroxychroman-2-yl ethyl |
| 132 | 2,5,7,8-tetramethyl-6-hydroxychroman-2-yl methyl |
| 133 | 2,2,4,6,7-pentamethyl-5-hydroxy-2,3-dihydrobenzofuran-3-yl carbonyl |

TABLE VIII-continued

[Structure: Pyrrolidine-N-Y with carboxylate ester to para-substituted benzyl-thiazolidine-2,4-dione]

| Compound number | Y |
|---|---|
| 134 | 2,2,4,6,7-pentamethyl-5-hydroxy-2,3-dihydrobenzofuran-3-yl carbonyl |

TABLE IX

[Structure: Pyrrolidine-N-Y with carboxylate ester to para-substituted benzylidene-thiazolidine-2,4-dione]

| Compound number | Y |
|---|---|
| 135 | benzoxazol-2-yl |
| 136 | benzothiazol-2-yl |
| 137 | pyridin-2-yl |
| 138 | 4,5-dimethylthiazol-2-yl |
| 139 | 2,5,7,8-tetramethyl-6-hydroxychroman-2-yl carbonyl |

TABLE IX-continued
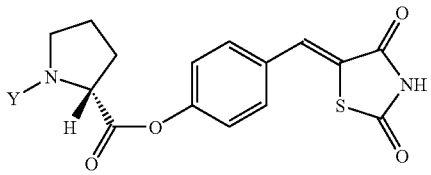
| Compound number | Y |
|---|---|
| 140 | 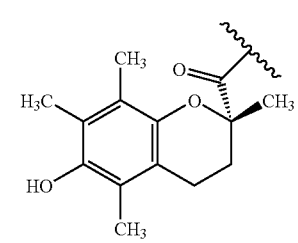 |
| 141 | 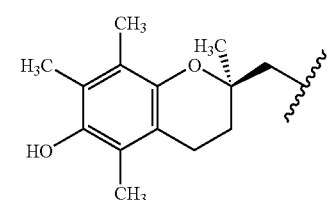 |
| 142 | 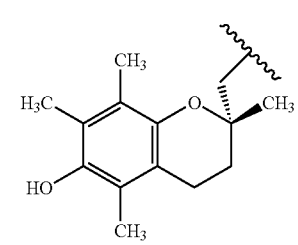 |
| 143 | 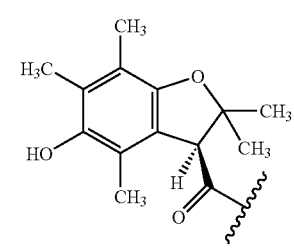 |
| 144 | 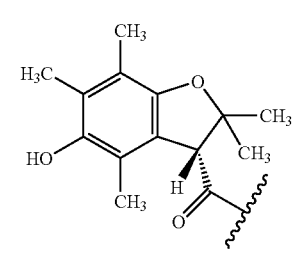 |
TABLE X
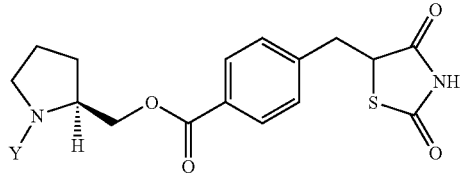
| Compound number | Y |
|---|---|
| 145 | 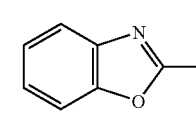 |
| 146 | 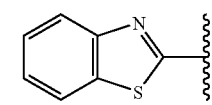 |
| 147 | 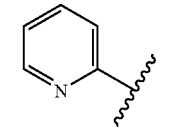 |
| 148 | 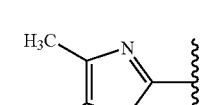 |
| 149 | 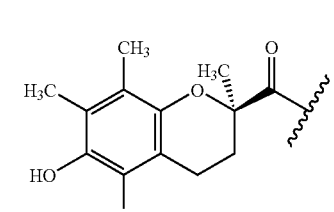 |
| 150 | 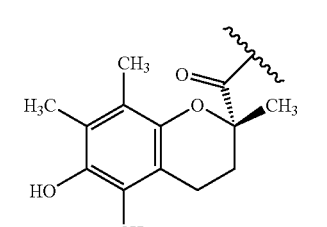 |
| 151 | 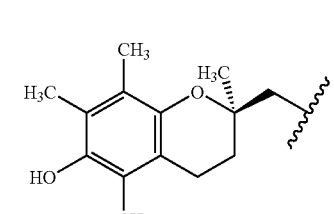 |

TABLE X-continued
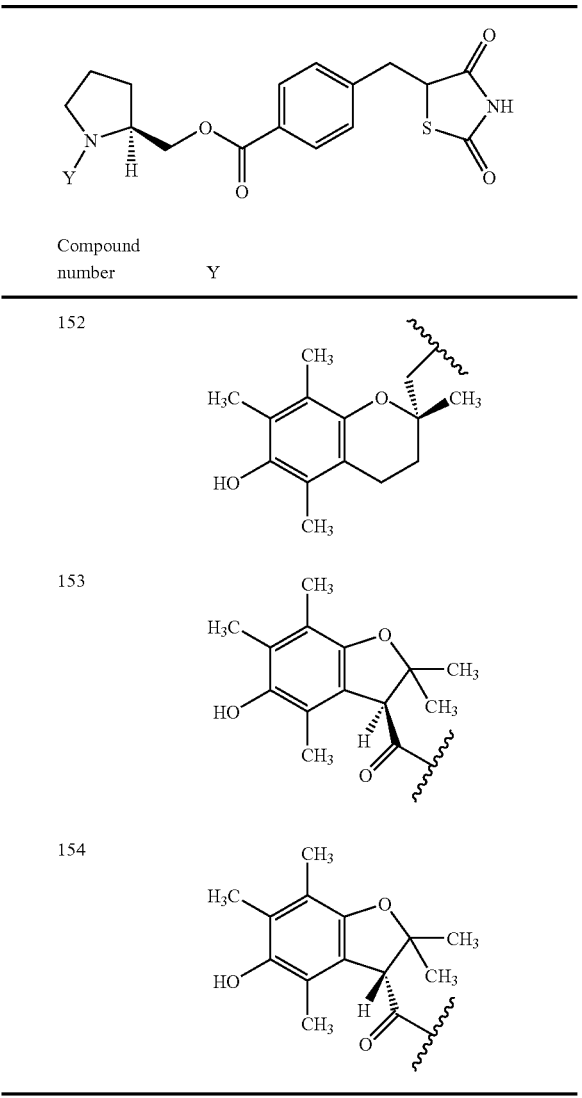
| Compound number | Y |
|---|---|
| 152 | |
| 153 | |
| 154 | |
TABLE XI
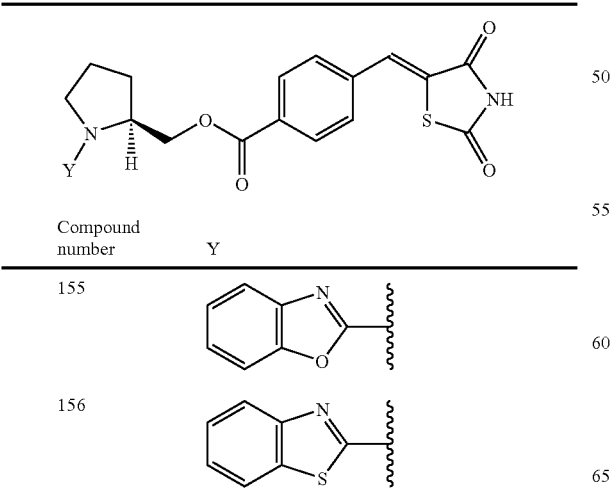
| Compound number | Y |
|---|---|
| 155 | |
| 156 | |
TABLE XI-continued
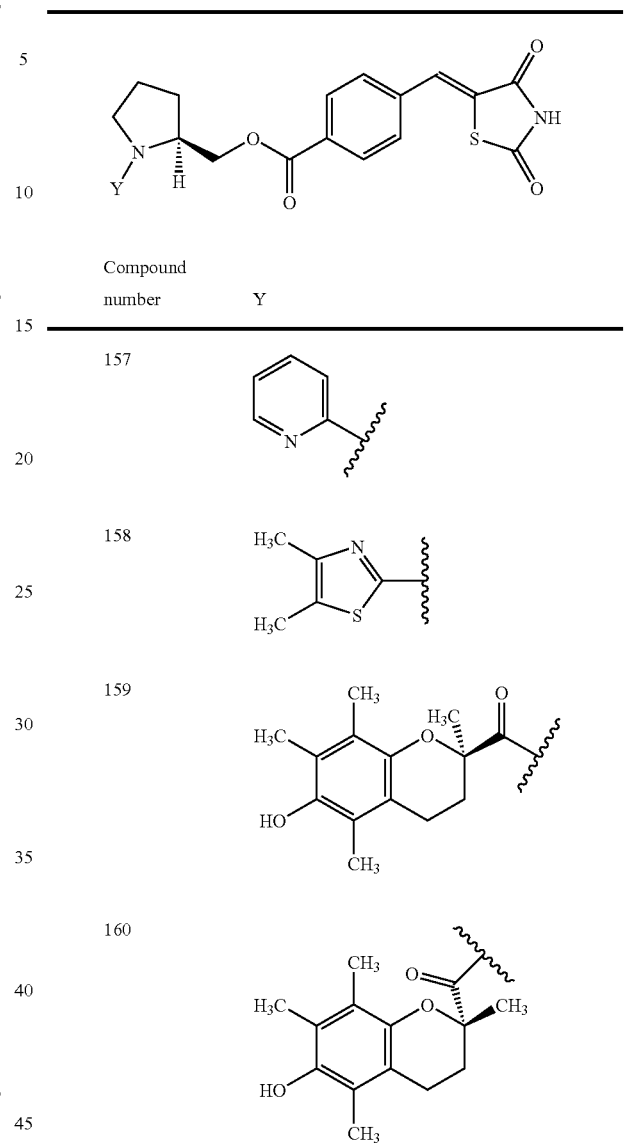
| Compound number | Y |
|---|---|
| 157 | |
| 158 | |
| 159 | |
| 160 | |
| 161 | |
| 162 | |

TABLE XI-continued
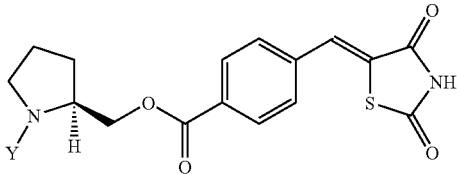
| Compound number | Y |
|---|---|
| 163 | 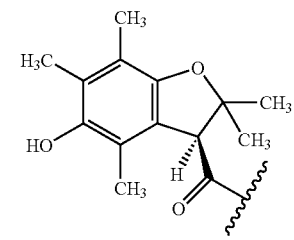 |
| 164 | 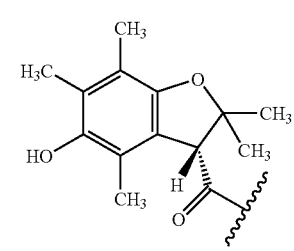 |
TABLE XII
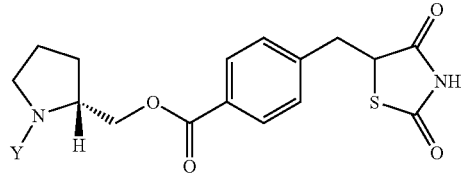
| Compound number | Y |
|---|---|
| 165 | 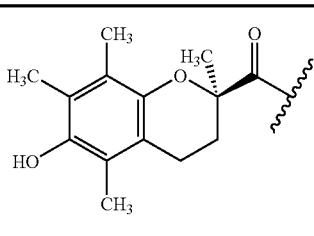 |
| 166 | 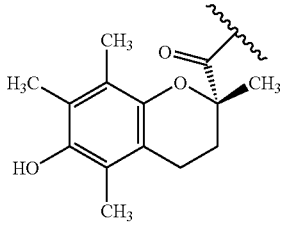 |
| 167 | 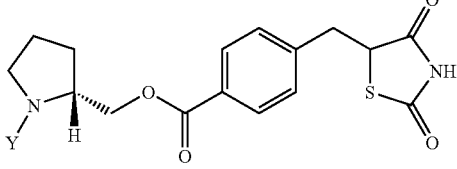 |
| 168 | 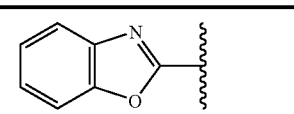 |
TABLE XII-continued
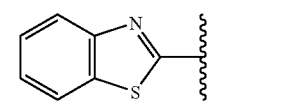
| Compound number | Y |
|---|---|
| 169 |  |
| 170 | 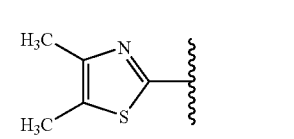 |
| 171 | 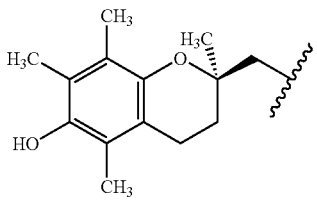 |
| 172 | 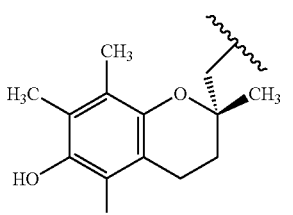 |
| 173 | 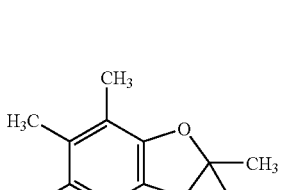 |

TABLE XII-continued
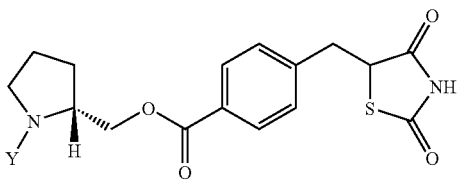
| Compound number | Y |
|---|---|
| 174 | 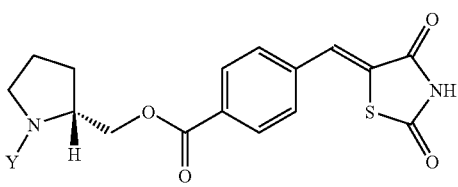 |
TABLE XIII
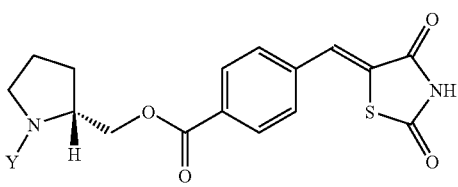
| Compound number | Y |
|---|---|
| 175 | 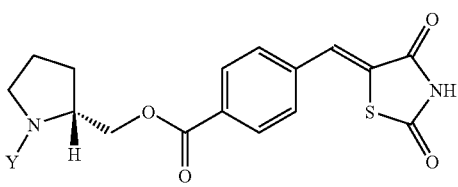 |
| 176 | 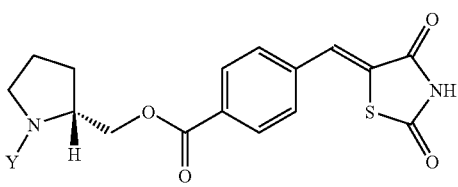 |
| 177 | 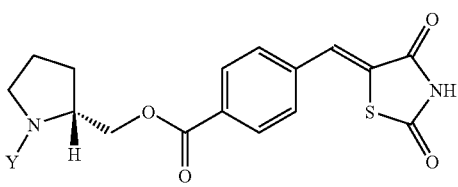 |
| 178 | 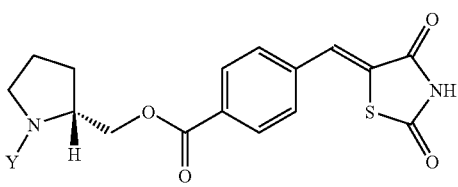 |
| 179 | 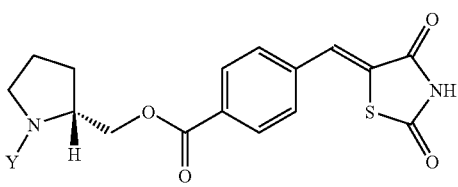 |
TABLE XIII-continued
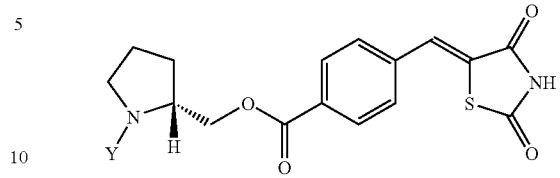
| Compound number | Y |
|---|---|
| 180 | 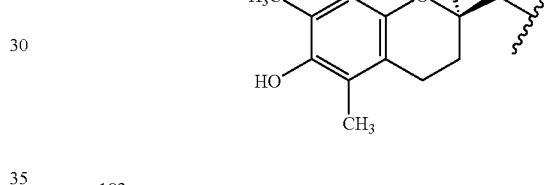 |
| 181 | 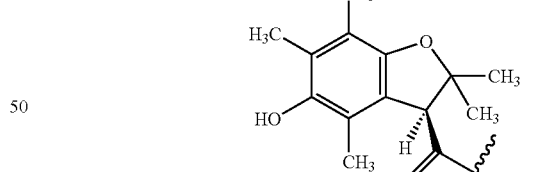 |
| 182 |  |
| 183 | 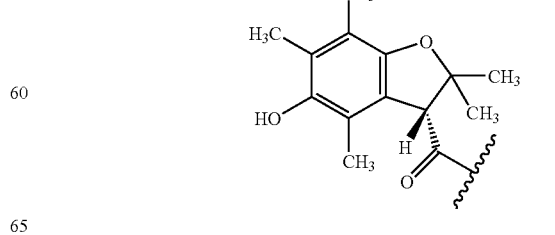 |
| 184 | 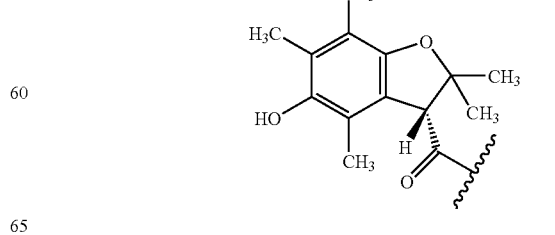 |

TABLE XIV
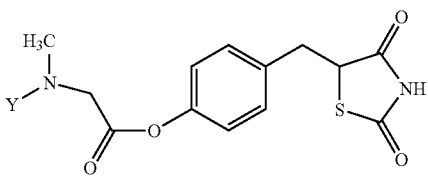
| Compound number | Y |
|---|---|
| 185 | 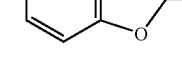 |
| 186 | 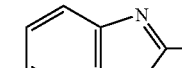 |
| 187 | 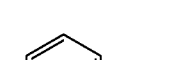 |
| 188 | 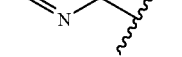 |
| 179 | 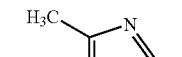 |
| 190 |  |
| 191 | 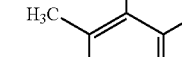 |
TABLE XIV-continued
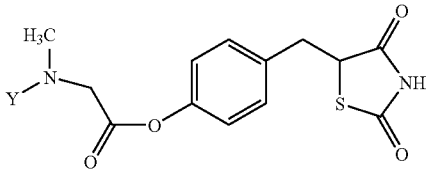
| Compound number | Y |
|---|---|
| 192 | |
| 193 | |
| 194 | |
TABLE XV
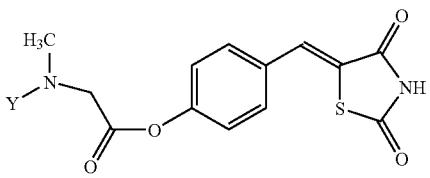
| Compound number | Y |
|---|---|
| 195 |  |
| 196 |  |

TABLE XV-continued

| Compound number | Y |
|---|---|
| 197 | 2-pyridyl |
| 198 | 4,5-dimethylthiazol-2-yl |
| 199 | (2,5,7,8-tetramethyl-6-hydroxychroman-2-yl)carbonyl |
| 200 | (2,5,7,8-tetramethyl-6-hydroxychroman-2-yl)carbonyl (stereoisomer) |
| 201 | (2,5,7,8-tetramethyl-6-hydroxychroman-2-yl)methyl |
| 202 | (2,5,7,8-tetramethyl-6-hydroxychroman-2-yl)methyl (stereoisomer) |
| 203 | (2,2,4,6,7-pentamethyl-5-hydroxy-2,3-dihydrobenzofuran-3-yl)carbonyl |
| 204 | (2,2,4,6,7-pentamethyl-5-hydroxy-2,3-dihydrobenzofuran-3-yl)carbonyl (stereoisomer) |

TABLE XVI

| Compound number | Y |
|---|---|
| 205 | benzoxazol-2-yl |
| 206 | benzothiazol-2-yl |
| 207 | 2-pyridyl |
| 208 | 4,5-dimethylthiazol-2-yl |

TABLE XVI-continued
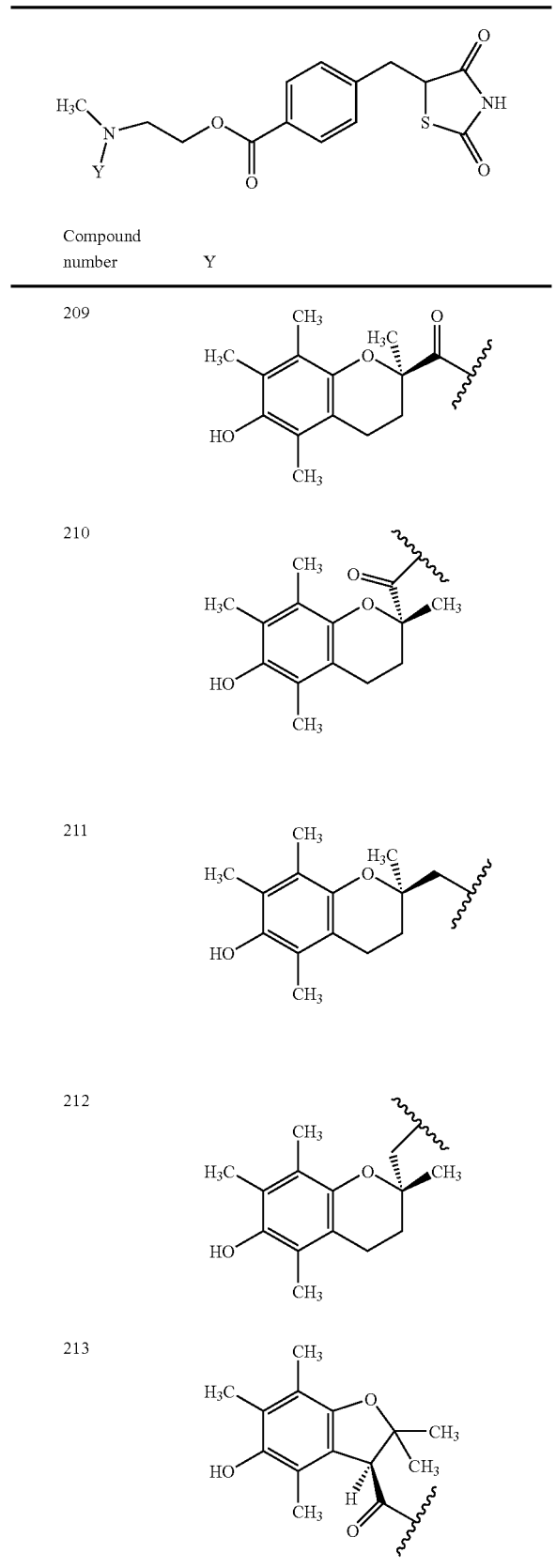
| Compound number | Y |
|---|---|
| 209 | |
| 210 | |
| 211 | |
| 212 | |
| 213 | |
TABLE XVI-continued
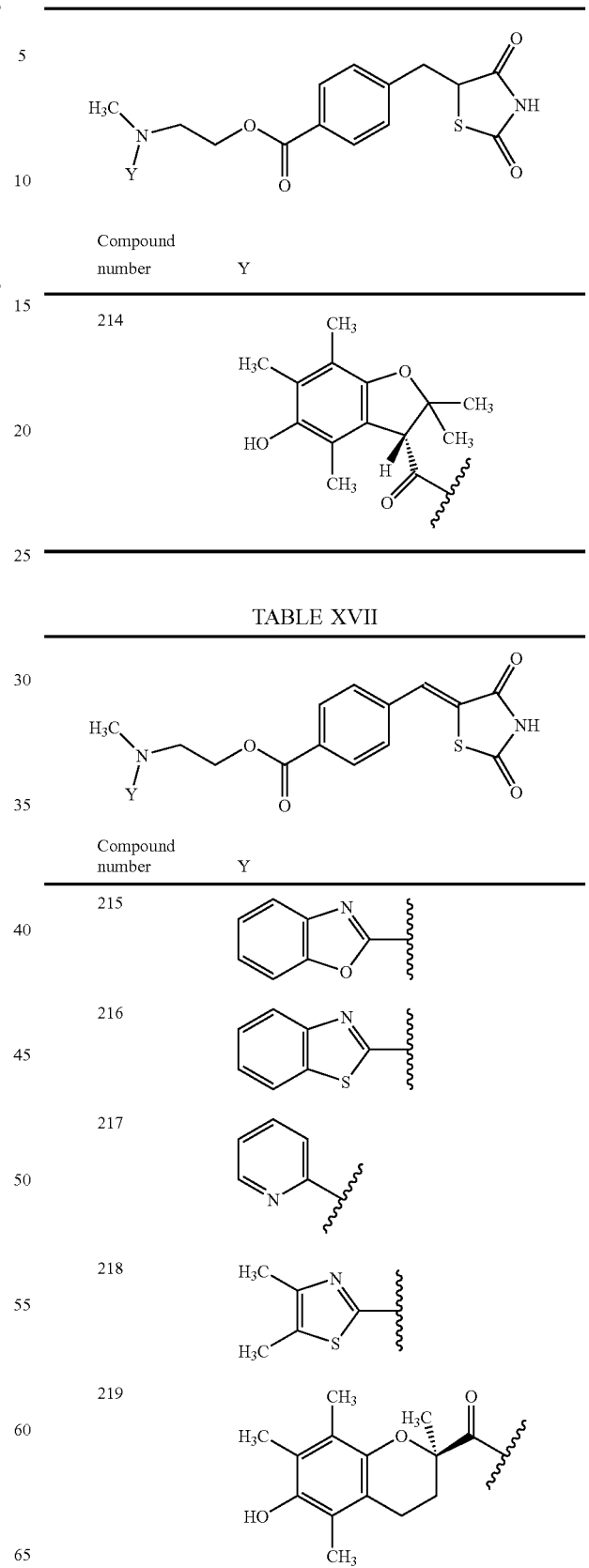
| Compound number | Y |
|---|---|
| 214 | |
TABLE XVII
| Compound number | Y |
|---|---|
| 215 | |
| 216 | |
| 217 | |
| 218 | |
| 219 | |

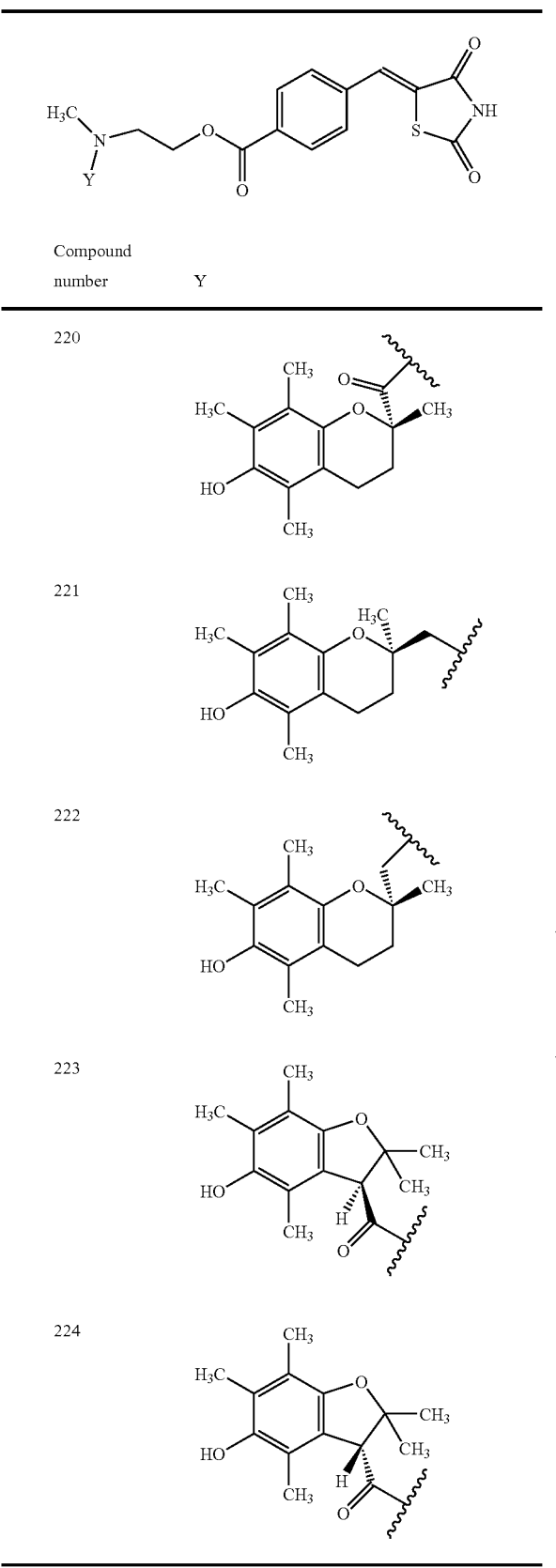
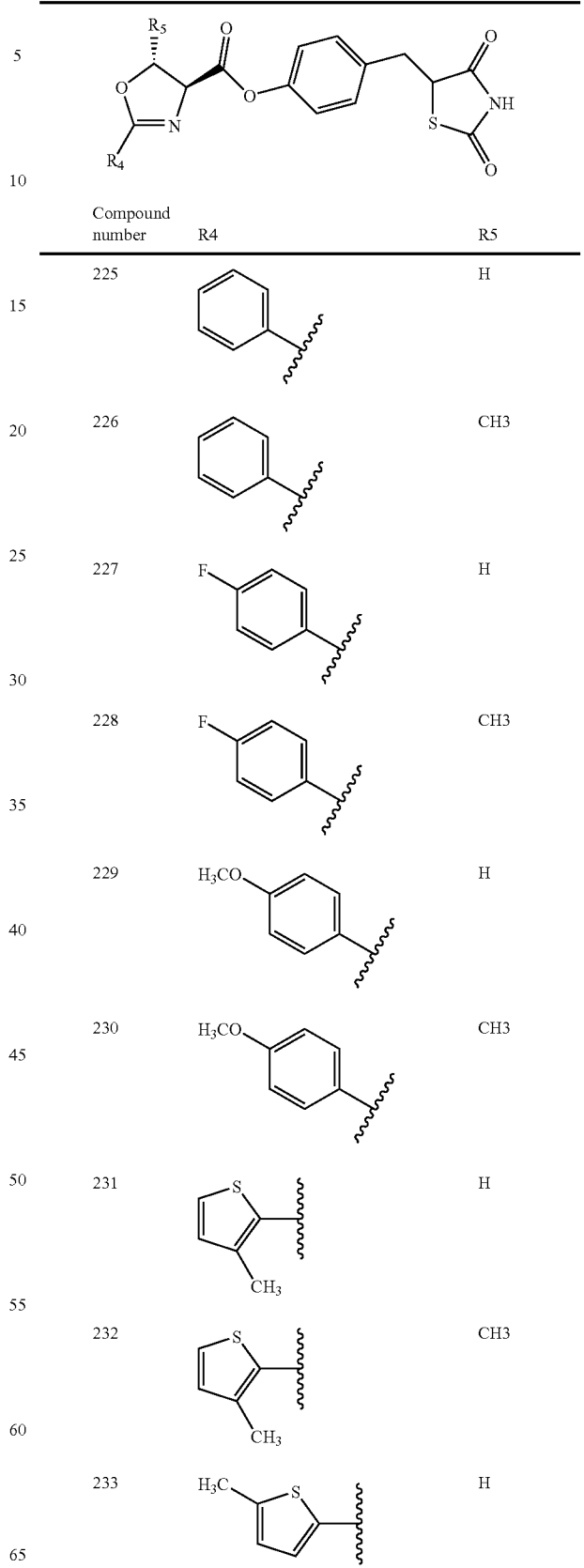

TABLE XVIII-continued
| Compound number | R4 | R5 |
|---|---|---|
| 234 | H3C-thienyl | CH3 |
| 235 | H3C-isoxazolyl | H |
| 236 | H3C-isoxazolyl | CH3 |
| 237 | 2-pyridyl | H |
| 238 | 2-pyridyl | CH3 |
| 239 | 4-pyridyl | H |
| 240 | 4-pyridyl | CH3 |
| 241 | pyrazinyl | H |
| 242 | pyrazinyl | CH3 |
TABLE XIX
| Compound number | Fib | P and Q* |
|---|---|---|
| 243 | 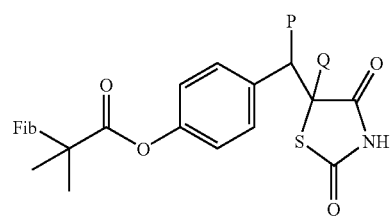 | H |
| 244 | | db |
| 245 | 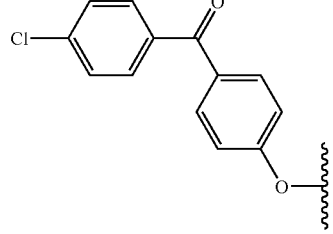 | H |
| 246 | | db |
| 247 | 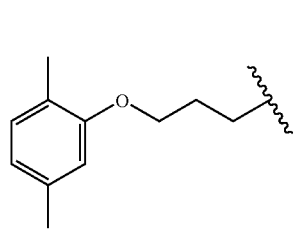 | H |
| 248 | | db |

TABLE XX
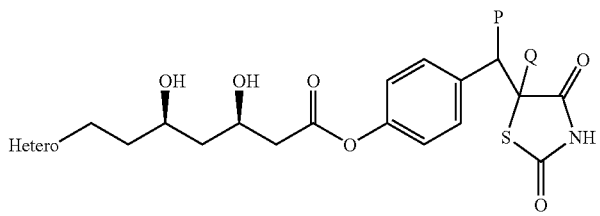
| Compound number | Hetero | P and Q* |
|---|---|---|
| 249 | (structure: atorvastatin-like pyrrole with anilide, isopropyl, phenyl, 4-fluorophenyl, and dihydroxy heptanoyl chain) | H |
| 250 | | db |
| 251 | (structure: lovastatin/simvastatin-like decalin with 2-methylbutanoate ester and dihydroxy heptanoyl chain) | H |
| 252 | | db |

TABLE XXI
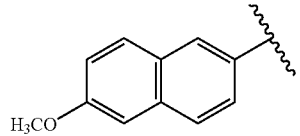
| Compound number | NSAID | P and Q* |
|---|---|---|
| 253 | 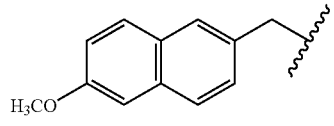 | H |
| 254 | | db |
| 255 | 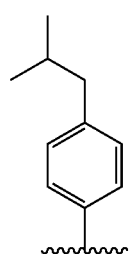 | H |
| 256 | | db |
| 257 | 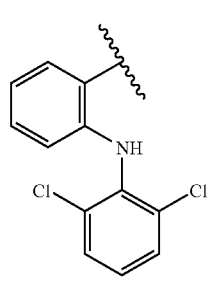 | H |
| 258 | | db |
| 259 | 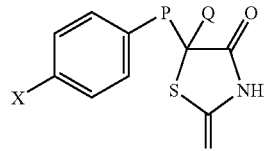 | H |
| 260 | | db |
TABLE XXII
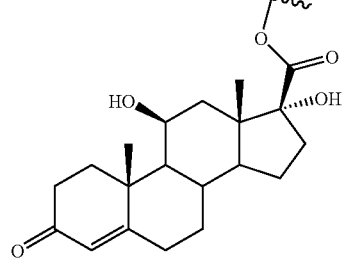
| Compound number | X | P and Q* |
|---|---|---|
| 261 | 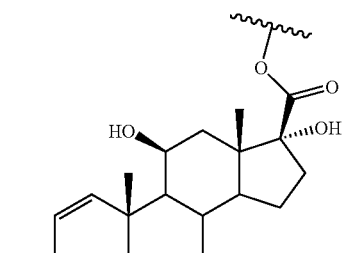 | H |
| 262 | | db |
| 263 | 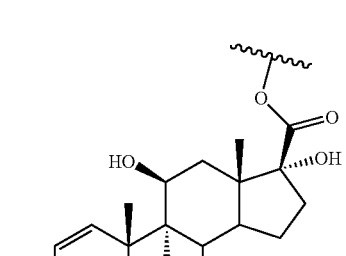 | H |
| 264 | | db |
| 265 | 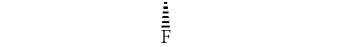 | H |
| 266 | | db |
| 267 |  | H |
| 268 | | db |

TABLE XXIII

Activity in NIDDM Mice.

| Compound | Serum Glucose (%) | Serum Insulin (%) |
|---|---|---|
| Vehicle | 0 | 1 |
| 105 | 40 | 10 |
| 115 | 36 | 13 |
| 155 | 37 | 9 |
| Troglitazone | 35 | 15 |

What is claimed is:

1. A composition comprising a carrier and a compound of Formula I

Formula I

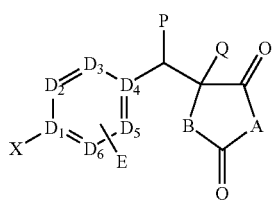

wherein:
  A is NH and B is sulfur;
  $D_1$–$D_6$ are C;
  E can be attached to one or more of the atoms located at $D_2$, $D_3$, $D_5$ or $D_6$;
  P and Q are a double bond; and
  E can be the same or different and is a moiety selected from the group consisting of H, $C_{1-10}$ alkyl, and substituted alkyl groups;
  X is a substituted carboxylic group comprising —N—$(C)_{1-3}$—C(O)O— that is attached to $D_1$;
  or salts of the compound of Formula I; or
  A is NH and B is sulfur;
  $D_1$–$D_6$ are C;
  E can be attached to one or more of the atoms located at $D_2$, $D_3$, $D_5$ or $D_6$;
  P and Q are hydrogen; and
  E is hydrogen;
  X is a substituted carboxylic group comprising —N—$(C)_{1-3}$—C(O)O— that is attached to $D_1$;
  or salts of the compound of Formula I.

2. The composition according to claim 1, wherein said substituted carboxylic group comprising —N—$(C)_{1-3}$—C(O)—O— is a portion of a moiety selected from the group consisting of a heteroarylcarbonyloxy, heteroalkylcarbonyloxy, and each of which is optionally substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, alkynylaryl, alkynylheteroaryl, aryl, $C_{1-20}$ alkylaryl, $C_{2-20}$ alkenylaryl, heteroaryl, $C_{1-20}$ alkylheteroaryl, $C_{2-20}$ alkenylheteroaryl, cycloalkyl, heterocycloalkyl, $C_{1-20}$ alkylheterocycloalkyl, and $C_{1-20}$ alkylcycloalkyl, any of which may be optionally substituted with a moiety selected from the group consisting of $C_{1-6}$ alkyl, halogen, OH, $NH_2$, CN, $NO_2$, COOH, or $SO_{2-4}$.

3. The composition according to claim 1, wherein said compound has the formula

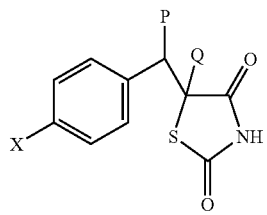

and wherein X, P, and Q are defined as:

| Compound number | X | P and Q |
|---|---|---|
| 7 | ![structure] | H; |
| 8 | | db | or salts thereof.

4. The composition according to claim 3, wherein said compound is compound 7 or a salt thereof.

5. The composition according to claim 3, wherein said compound is compound 8 or a salt thereof.

6. The composition according to claim 1, wherein said compound has the formula

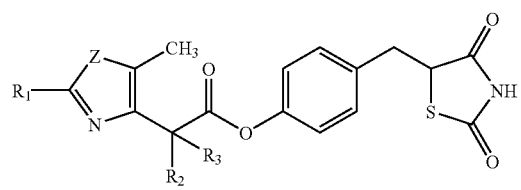

and wherein $R_1$, $R_2$, $R_3$, and Z are defined as:

| Compound number | Z | $R_1$ | $R_2$ | $R_3$ |
|---|---|---|---|---|
| 33 | O | phenyl | H | H; |
| 34 | O | phenyl | $CH_3$ | H; |

-continued

| Compound number | Z | R₁ | R₂ | R₃ |
|---|---|---|---|---|
| 35 | O | phenyl | CH₃ | CH₃; |
| 36 | S | phenyl | CH₃ | H; |
| 37 | O | 4-F-phenyl | CH₃ | H; |
| 38 | S | 4-F-phenyl | CH₃ | H; |
| 39 | O | 4-H₃CO-phenyl | CH₃ | H; |
| 40 | S | 4-H₃CO-phenyl | CH₃ | H; |
| 41 | O | 3-methylthiophen-2-yl | CH₃ | H; |
| 42 | S | 3-methylthiophen-2-yl | CH₃ | H; |
| 43 | O | 5-methylthiophen-2-yl | H | H; |
| 44 | O | 5-methylthiophen-2-yl | CH₃ | H; |
| 45 | S | 5-methylthiophen-2-yl | H | H; |
| 46 | O | 5-methylisoxazol-3-yl | CH₃ | H; |
| 47 | S | 5-methylisoxazol-3-yl | H | H; |
| 48 | O | pyridin-2-yl | CH₃ | H; |
| 49 | O | pyridin-4-yl | CH₃ | H; or |
| 50 | O | pyrazin-2-yl | CH₃ | H; or salts thereof. |

7. The composition according to claim 6, wherein said compound is compound 33, or a salt thereof.

8. The composition according to claim 6, wherein said compound is compound 34, or a salt thereof.

9. The composition according to claim 6, wherein said compound is compound 35, or a salt thereof.

10. The composition according to claim 6, wherein said compound is compound 36, or a salt thereof.

11. The composition according to claim 6, wherein said compound is compound 37, or a salt thereof.

12. The composition according to claim 6, wherein said compound is compound 38, or a salt thereof.

13. The composition according to claim 6, wherein said compound is compound 39, or a salt thereof.

14. The composition according to claim 6, wherein said compound is compound 40, or a salt thereof.

15. The composition according to claim 6, wherein said compound is compound 41, or a salt thereof.

16. The composition according to claim 6, wherein said compound is compound 42, or a salt thereof.

17. The composition according to claim 6, wherein said compound is compound 43, or a salt thereof.

18. The composition according to claim 6, wherein said compound is compound 44, or a salt thereof.

19. The composition according to claim 6, wherein said compound is compound 45, or a salt thereof.

20. The composition according to claim 6, wherein said compound is compound 46, or a salt thereof.

21. The composition according to claim 6, wherein said compound is compound 47, or a salt thereof.

22. The composition according to claim 6, wherein said compound is compound 48, or a salt thereof.

23. The composition according to claim 6, wherein said compound is compound 49, or a salt thereof.

24. The composition according to claim 6, wherein said compound is compound 50, or a salt thereof.

25. The composition according to claim 1, wherein said compound has the formula

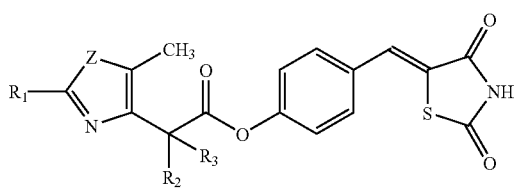

and wherein $R_1$, $R_2$, $R_3$, and Z are defined as:

| Compound number | Z | $R_1$ | $R_2$ | $R_3$ |
|---|---|---|---|---|
| 51 | O | phenyl | H | H; |
| 52 | O | phenyl | CH$_3$ | H; |
| 53 | O | phenyl | CH$_3$ | CH$_3$; |
| 54 | S | phenyl | CH$_3$ | H; |
| 55 | O | 4-F-phenyl | CH$_3$ | H; |
| 56 | S | 4-F-phenyl | CH$_3$ | H; |
| 57 | O | 4-H$_3$CO-phenyl | CH$_3$ | H; |
| 58 | S | 4-H$_3$CO-phenyl | CH$_3$ | H; |
| 59 | O | 3-CH$_3$-thien-2-yl | CH$_3$ | H; |
| 60 | S | 3-CH$_3$-thien-2-yl | CH$_3$ | H; |
| 61 | O | 5-CH$_3$-thien-2-yl | H | H; |
| 62 | O | 5-CH$_3$-thien-2-yl | CH$_3$ | H; |
| 63 | S | 5-CH$_3$-thien-2-yl | H | H; |
| 64 | O | 5-CH$_3$-isoxazol-3-yl | CH$_3$ | H; |
| 65 | S | 5-CH$_3$-isoxazol-3-yl | H | H; |
| 66 | O | pyridin-2-yl | CH$_3$ | H; |
| 67 | O | pyridin-4-yl | CH$_3$ | H; or |
| 68 | O | pyrazin-2-yl | CH$_3$ | H; or salts thereof. |

26. The composition according to claim 25, wherein said compound is compound 51, or a salt thereof.

27. The composition according to claim 25, wherein said compound is compound 52, or a salt thereof.

28. The composition according to claim 25, wherein said compound is compound 53, or a salt thereof.

29. The composition according to claim 25, wherein said compound is compound 54, or a salt thereof.

30. The composition according to claim 25, wherein said compound is compound 55, or a salt thereof.

31. The composition according to claim 25, wherein said compound is compound 56, or a salt thereof.

32. The composition according to claim 25, wherein said compound is compound 57, or a salt thereof.

33. The composition according to claim 25, wherein said compound is compound 58, or a salt thereof.

34. The composition according to claim 25, wherein said compound is compound 59, or a salt thereof.

35. The composition according to claim 25, wherein said compound is compound 60, or a salt thereof.

36. The composition according to claim 25, wherein said compound is compound 61, or a salt thereof.

37. The composition according to claim 25, wherein said compound is compound 62, or a salt thereof.

38. The composition according to claim 25, wherein said compound is compound 63, or a salt thereof.

39. The composition according to claim 25, wherein said compound is compound 64, or a salt thereof.

40. The composition according to claim 25, wherein said compound is compound 65, or a salt thereof.

41. The composition according to claim 25, wherein said compound is compound 66, or a salt thereof.

42. The composition according to claim 25, wherein said compound is compound 67, or a salt thereof.

43. The composition according to claim 25, wherein said compound is compound 68, or a salt thereof.

44. The composition according to claim 1, wherein said compound has the formula

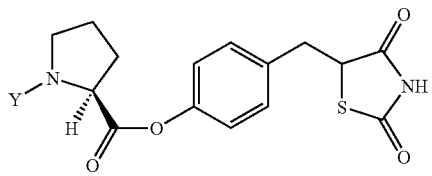

and wherein Y is defined as:

| Compound Number | Y |
|---|---|
| 105 | benzoxazol-2-yl |
| 106 | benzothiazol-2-yl |
| 107 | pyridin-2-yl |
| 108 | 4,5-dimethylthiazol-2-yl |
| 109 | (2)-6-hydroxy-2,5,7,8-tetramethylchroman-2-yl carbonyl |
| 110 | (2)-6-hydroxy-2,5,7,8-tetramethylchroman-2-yl carbonyl (methyl) |
| 111 | 6-hydroxy-2,5,7,8-tetramethylchroman-2-yl methyl |
| 112 | (2)-6-hydroxy-2,5,7,8-tetramethylchroman-2-yl methyl |
| 113 | 5-hydroxy-2,2,4,6,7-pentamethyl-2,3-dihydrobenzofuran-3-yl carbonyl; or |
| 114 | 5-hydroxy-2,2,4,6,7-pentamethyl-2,3-dihydrobenzofuran-3-yl carbonyl or salts thereof. |

45. The composition according to claim 44, wherein said compound is compound 105, or a salt thereof.

46. The composition according to claim 44, wherein said compound is compound 106, or a salt thereof.

47. The composition according to claim 44, wherein said compound is compound 107, or a salt thereof.

48. The composition according to claim 44, wherein said compound is compound 108, or a salt thereof.

49. The composition according to claim 44, wherein said compound is compound 109, or a salt thereof.

50. The composition according to claim 44, wherein said compound is compound 110, or a salt thereof.

51. The composition according to claim 44, wherein said compound is compound 111, or a salt thereof.

52. The composition according to claim 44, wherein said compound is compound 112, or a salt thereof.

53. The composition according to claim 44, wherein said compound is compound 113, or a salt thereof.

54. The composition according to claim 44, wherein said compound is compound 114, or a salt thereof.

55. The composition according to claim 1, wherein said compound has the formula

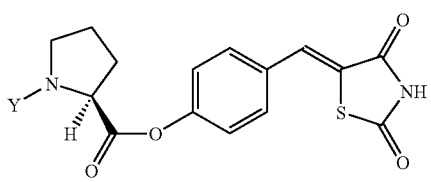

and wherein Y is defined as:

| Compound number | Y |
|---|---|
| 115 | 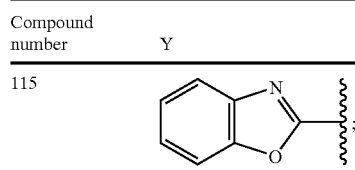 |
| 116 | 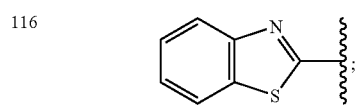 |
| 117 | 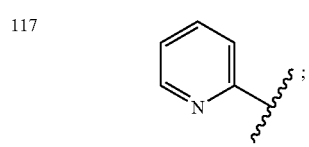 |
| 118 | 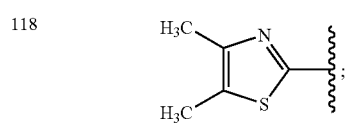 |
| 119 | 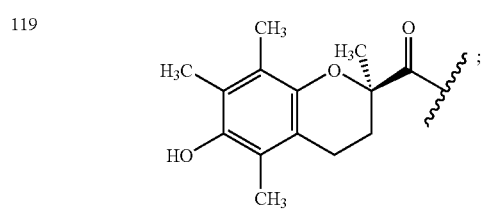 |
| 120 | ![120] |
| 121 | ![121] |
| 122 | ![122] |
| 123 | ![123] |
| 124 | ![124] or salts thereof. |

56. The composition according to claim 55, wherein said compound is compound 115, or a salt thereof.

57. The composition according to claim 55, wherein said compound is compound 116, or a salt thereof.

58. The composition according to claim 55, wherein said compound is compound 117, or a salt thereof.

59. The composition according to claim 55, wherein said compound is compound 118, or a salt thereof.

60. The composition according to claim 55, wherein said compound is compound 119, or a salt thereof.

61. The composition according to claim 55, wherein said compound is compound 120, or a salt thereof.

62. The composition according to claim 55, wherein said compound is compound 121, or a salt thereof.

63. The composition according to claim 55, wherein said compound is compound 122, or a salt thereof.

64. The composition according to claim 55, wherein said compound is compound 123, or a salt thereof.

65. The composition according to claim 55, wherein said compound is compound 124, or a salt thereof.

66. The composition according to claim 1, wherein said compound has the formula

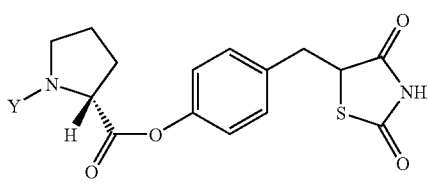

and wherein Y is defined as:

| Compound number | Y |
|---|---|
| 125 | 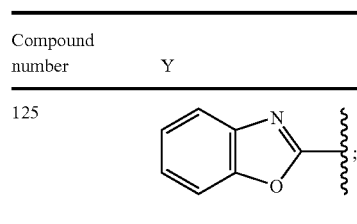 |
| 126 | |
| 127 | |
| 128 | |
| 129 | 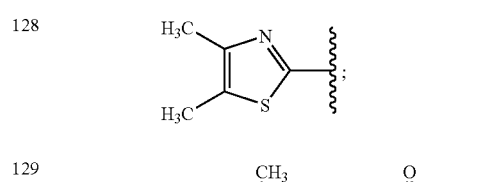 |
| 130 | 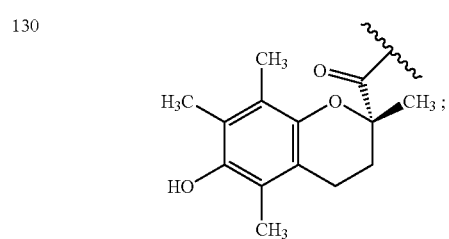 |

-continued

| Compound number | Y |
|---|---|
| 131 | |
| 132 | |
| 133 | |
| 134 | |

67. The composition according to claim 66, wherein said compound is compound 125, or a salt thereof.

68. The composition according to claim 66, wherein said compound is compound 126, or a salt thereof.

69. The composition according to claim 66, wherein said compound is compound 127, or a salt thereof.

70. The composition according to claim 66, wherein said compound is compound 128, or a salt thereof.

71. The composition according to claim 66, wherein said compound is compound 129, or a salt thereof.

72. The composition according to claim 66, wherein said compound is compound 130, or a salt thereof.

73. The composition according to claim 66, wherein said compound is compound 131, or a salt thereof.

74. The composition according to claim 66, wherein said compound is compound 132, or a salt thereof.

75. The composition according to claim 66, wherein said compound is compound 133, or a salt thereof.

76. The composition according to claim 66, wherein said compound is compound 134, or a salt thereof.

77. The composition according to claim 1, wherein said compound has the formula

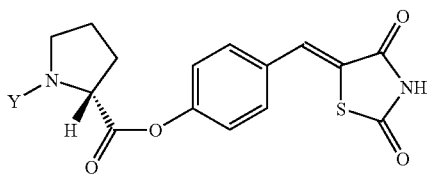

and wherein Y is defined as:

| Compound number | Y |
|---|---|
| 135 | |
| 136 | |
| 137 | |
| 138 | |
| 139 | |
| 140 | |
| 141 | |

-continued

| Compound number | Y |
|---|---|
| 142 | |
| 143 | |
| 144 | |

78. The composition according to claim 77, wherein said compound is compound 135, or a salt thereof.

79. The composition according to claim 77, wherein said compound is compound 136, or a salt thereof.

80. The composition according to claim 77, wherein said compound is compound 137, or a salt thereof.

81. The composition according to claim 77, wherein said compound is compound 138, or a salt thereof.

82. The composition according to claim 77, wherein said compound is compound 139, or a salt thereof.

83. The composition according to claim 77, wherein said compound is compound 140, or a salt thereof.

84. The composition according to claim 77, wherein said compound is compound 141, or a salt thereof.

85. The composition according to claim 77, wherein said compound is compound 142, or a salt thereof.

86. The composition according to claim 77, wherein said compound is compound 143, or a salt thereof.

87. The composition according to claim 77, wherein said compound is compound 144, or a salt thereof.

88. The composition according to claim 1, wherein said compound has the formula

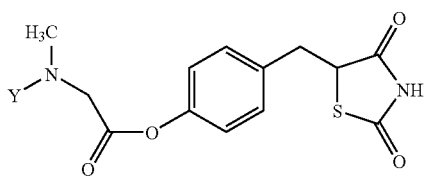

and wherein Y is defined as:

| Compound number | Y |
|---|---|
| 185 | [benzoxazol-2-yl] |
| 186 | [benzothiazol-2-yl] |
| 187 | [pyridin-2-yl] |
| 188 | [4,5-dimethylthiazol-2-yl] |
| 189 | [6-hydroxy-2,5,7,8-tetramethylchroman-2-yl carbonyl] |
| 190 | [6-hydroxy-2,5,7,8-tetramethylchroman-2-yl carbonyl] |
| 191 | [6-hydroxy-2,5,7,8-tetramethylchroman-2-yl methyl] |
| 192 | [6-hydroxy-2,5,7,8-tetramethylchroman-2-yl methyl] |
| 193 | [6-hydroxy-2,2,4,5,7-pentamethyl-2,3-dihydrobenzofuran-3-yl carbonyl]; or |
| 194 | [6-hydroxy-2,2,4,5,7-pentamethyl-2,3-dihydrobenzofuran-3-yl carbonyl] or salts thereof. |

89. The composition according to claim 88, wherein said compound is compound 185, or a salt thereof.

90. The composition according to claim 88, wherein said compound is compound 186, or a salt thereof.

91. The composition according to claim 88, wherein said compound is compound 187, or a salt thereof.

92. The composition according to claim 88, wherein said compound is compound 188, or a salt thereof.

93. The composition according to claim 88, wherein said compound is compound 189, or a salt thereof.

94. The composition according to claim 88, wherein said compound is compound 190, or a salt thereof.

95. The composition according to claim 88, wherein said compound is compound 191, or a salt thereof.

96. The composition according to claim 88, wherein said compound is compound 192, or a salt thereof.

97. The composition according to claim 88, wherein said compound is compound 193, or a salt thereof.

98. The composition according to claim 88, wherein said compound is compound 194, or a salt thereof.

99. The composition according to claim 1, wherein said compound has the formula

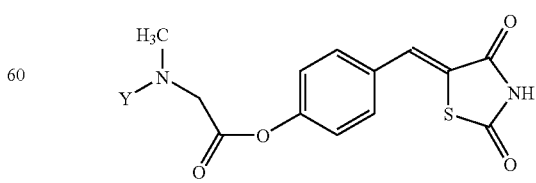

and wherein Y is defined as:

| Compound number | Y |
|---|---|
| 195 | benzoxazol-2-yl |
| 196 | benzothiazol-2-yl |
| 197 | pyridin-2-yl |
| 198 | 4,5-dimethylthiazol-2-yl |
| 199 | 6-hydroxy-2,5,7,8-tetramethylchroman-2-yl carbonyl |
| 200 | 6-hydroxy-2,5,7,8-tetramethylchroman-2-yl carbonyl (stereoisomer) |
| 201 | 6-hydroxy-2,5,7,8-tetramethylchroman-2-yl methyl |
| 202 | 6-hydroxy-2,5,7,8-tetramethylchroman-2-yl methyl (stereoisomer) |
| 203 | 5-hydroxy-2,4,6,7-tetramethyl-2,3-dihydrobenzofuran-3-yl carbonyl; or |
| 204 | 5-hydroxy-2,4,6,7-tetramethyl-2,3-dihydrobenzofuran-3-yl carbonyl or salts thereof. |

100. The composition according to claim 99, wherein said compound is compound 195, or a salt thereof.

101. The composition according to claim 99, wherein said compound is compound 196, or a salt thereof.

102. The composition according to claim 99, wherein said compound is compound 197, or a salt thereof.

103. The composition according to claim 99, wherein said compound is compound 198, or a salt thereof.

104. The composition according to claim 99, wherein said compound is compound 199, or a salt thereof.

105. The composition according to claim 99, wherein said compound is compound 200, or a salt thereof.

106. The composition according to claim 99, wherein said compound is compound 201, or a salt thereof.

107. The composition according to claim 99, wherein said compound is compound 202, or a salt thereof.

108. The composition according to claim 99, wherein said compound is compound 203, or a salt thereof.

109. The composition according to claim 99, wherein said compound is compound 204, or a salt thereof.

110. The composition according to claim 1, wherein said compound has the formula

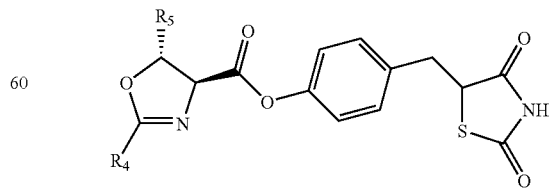

and wherein $R_4$ and $R_5$ are defined as:

| Compound number | R₄ | R₅ |
|---|---|---|
| 225 | phenyl | H; |
| 226 | phenyl | CH₃; |
| 227 | 4-F-phenyl | H; |
| 228 | 4-F-phenyl | CH₃; |
| 229 | 4-H₃CO-phenyl | H; |
| 230 | 4-H₃CO-phenyl | CH₃; |
| 231 | 3-methylthiophen-2-yl | H; |
| 232 | 3-methylthiophen-2-yl | CH₃; |
| 233 | 5-methylthiophen-2-yl | H; |
| 234 | 5-methylthiophen-2-yl | CH₃; |
| 235 | 5-methylisoxazol-3-yl | H; |
| 236 | 5-methylisoxazol-3-yl | CH₃; |
| 237 | pyridin-2-yl | H; |
| 238 | pyridin-2-yl | CH₃; |
| 239 | pyridin-4-yl | H; |
| 240 | pyridin-4-yl | CH₃; |
| 241 | pyrazin-2-yl | H; or |
| 242 | pyrazin-2-yl | CH₃ or salts thereof. |

111. The composition according to claim 110 wherein said compound is compound 225, or a salt thereof.

112. The composition according to claim 110, wherein said compound is compound 226, or a salt thereof.

113. The composition according to claim 110, wherein said compound is compound 227, or a salt thereof.

114. The composition according to claim 110, wherein said compound is compound 228, or a salt thereof.

115. The composition according to claim 110, wherein said compound is compound 229, or a salt thereof.

116. The composition according to claim 110, wherein said compound is compound 230, or a salt thereof.

117. The composition according to claim 110, wherein said compound is compound 231, or a salt thereof.

118. The composition according to claim 110, wherein said compound is compound 232, or a salt thereof.

119. The composition according to claim 110, wherein said compound is compound 233, or a salt thereof.

120. The composition according to claim 110, wherein said compound is compound 234, or a salt thereof.

121. The composition according to claim 110, wherein said compound is compound 235, or a salt thereof.

122. The composition according to claim 110, wherein said compound is compound 236, or a salt thereof.

123. The composition according to claim 110, wherein said compound is compound 237, or a salt thereof.

124. The composition according to claim 110, wherein said compound is compound 238, or a salt thereof.

125. The composition according to claim 110, wherein said compound is compound 239, or a salt thereof.

126. The compound, according to claim 110, wherein said compound is compound 240, or a salt thereof.

127. The composition according to claim 110, wherein said compound is compound 241, or a salt thereof.

128. The composition according to claim 110, wherein said compound is compound 242, or a salt thereof.

129. The composition according to claim 1, wherein:
   A is NH and B is sulfur;
   $D_1$–$D_6$ are C;
   E can be attached to one or more of the atoms located at $D_2$, $D_3$, $D_5$ or $D_6$;
   P and Q are a double bond;
   E can be the same or different and is a moiety selected from the group consisting of H, $C_{1-10}$ alkyl, and substituted alkyl groups; and
   X is a substituted carboxylic group comprising —N—$(C)_{1-3}$—C(O)O— that is attached to $D_1$;
or salts of the compound of Formula I.

130. The composition according to claim 1, wherein
   A is NH and B is sulfur;
   $D_1$–$D_6$ are C;
   E can be attached to one or more of the atoms located at $D_2$, $D_3$, $D_5$ or $D_6$;
   P and Q are hydrogen;
   E is hydrogen; and
   X is a substituted carboxylic group comprising —N—$(C)_{1-3}$—C(O)O— that is attached to $D_1$;
or salts of the compound of Formula I.

131. A method of treating diabetes, atherosclerosis, hypercholesterolemia, or hyperlipidemia comprising the administration of a therapeutically effective amount of the composition comprising a carrier and a compound of Formula I

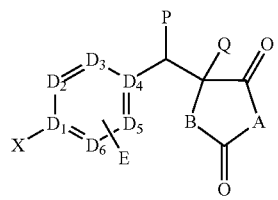

Formula I wherein:
   A is NH and B is sulfur;
   $D_1$–$D_6$ are C;
   E can be attached to one or more of the atoms located at $D_2$, $D_3$, $D_5$ or $D_6$;
   P and Q are a double bond; and
   E can be the same or different and is a moiety selected from the group consisting of H, $C_{1-10}$, alkyl, and substituted alkyl groups;
   X is a substituted carboxylic group comprising —N—$(C)_{1-3}$—C(O)O— that is attached to $D_1$;
   or salts of the compound of Formula I; or
   A is NH and B is sulfur;
   $D_1$–$D_6$ are C;
   E can be attached to one or more of the atoms located at $D_2$, $D_3$, $D_5$ or $D_6$;
   P and Q are hydrogen; and
   E is hydrogen;
   X is a substituted carboxylic group comprising —N—$(C)_{1-3}$—C(O)O— that is attached to $D_1$;
   or salts of the compound of Formula I.

132. The method according to claim 131, wherein said substituted carboxylic acid group comprising —N—$(C)_{1-3}$—C(O)—O— is a portion of a moiety selected from the group consisting of a heteroarylcarbonyloxy, heteroalkylcarbonyloxy, and each of which is optionally substituted with $C_{1-10}$ alkyl, CN, COOH, $NO_2$, $NH_2$, $SO_{2-4}$, $C_{1-20}$ heteroalkyl, $C_{2-20}$ alkenyl, alkynyl, alkynylaryl, alkynylheteroaryl, aryl, $C_{1-20}$ alkylaryl, $C_{2-20}$ alkenylaryl, heteroaryl, $C_{1-20}$ alkylheteroaryl, $C_{2-20}$ alkenylheteroaryl, cycloalkyl, heterocycloalkyl, $C_{1-20}$ alkylheterocycloalkyl, and $C_{1-20}$ alkylcycloalkyl, any of which may be optionally substituted with a moiety selected from the group consisting of $C_{1-6}$ alkyl, halogen, OH, $NH_2$, CN, $NO_2$, COOH, or $SO_{2-4}$.

133. The method according to claim 131, wherein the compound of said composition has the formula

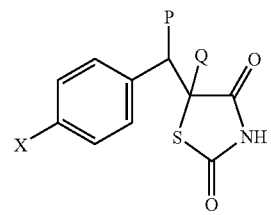

and wherein X, P, and Q are defined as:

| Compound number | X | P and Q |
|---|---|---|
| 7 | ![structure] | H; |
| 8 | | db |

134. The method according to claim 133, wherein the compound of said composition is compound 7 or a salt thereof.

135. The method according to claim 133, wherein the compound of said composition is compound 8 or a salt thereof.

136. The method according to claim 131, wherein compound of said on has the formula

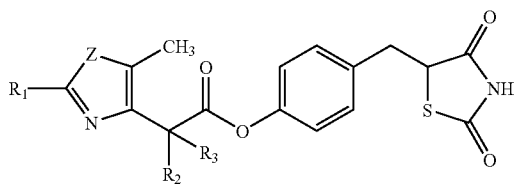

in $R_1$, $R_2$, $R_3$, and Z are defined as:

| Compound number | Z | $R_1$ | $R_2$ | $R_3$ |
|---|---|---|---|---|
| 33 | O | phenyl | H | H; |
| 34 | O | phenyl | $CH_3$ | H; |
| 35 | O | phenyl | $CH_3$ | $CH_3$; |
| 36 | S | phenyl | $CH_3$ | H; |
| 37 | O | 4-F-phenyl | $CH_3$ | H; |
| 38 | S | 4-F-phenyl | $CH_3$ | H; |
| 39 | O | 4-$H_3CO$-phenyl | $CH_3$ | H; |
| 40 | S | 4-$H_3CO$-phenyl | $CH_3$ | H; |
| 41 | O | 3-methylthiophen-2-yl | $CH_3$ | H; |
| 42 | S | 3-methylthiophen-2-yl | $CH_3$ | H; |
| 43 | O | 5-methylthiophen-2-yl | H | H; |
| 44 | O | 5-methylthiophen-2-yl | $CH_3$ | H; |
| 45 | S | 5-methylthiophen-2-yl | H | H; |
| 46 | O | 5-methylisoxazol-3-yl | $CH_3$ | H; |
| 47 | S | 5-methylisoxazol-3-yl | H | H; |
| 48 | O | pyridin-2-yl | $CH_3$ | H; |
| 49 | O | pyridin-4-yl | $CH_3$ | H; or |
| 50 | O | pyrazin-2-yl | $CH_3$ | H; or salts thereof. |

137. The method according to claim 136, wherein the compound of said composition is compound 33, or a salt thereof.

138. The method according to claim 136, wherein the compound of said composition is compound 34, or a salt thereof.

139. The method according to claim 136, wherein the compound of said composition is compound 35, or a salt thereof.

140. The method according to claim 136, wherein the compound of said composition is compound 36, or a salt thereof.

141. The method according to claim 136, wherein the compound of said composition is compound 37, or a salt thereof.

142. The method according to claim 136, wherein the compound of said composition is compound 38, or a salt thereof.

143. The method according to claim 136, wherein the compound of said composition is compound 39, or a salt thereof.

144. The method according to claim 136, wherein the compound of said composition is compound 40, or a salt thereof.

145. The method according to claim 136, wherein the compound of said composition is compound 41, or a salt thereof.

146. The method according to claim 136, wherein the compound of said composition is compound 42, or a salt thereof.

147. The method according to claim 136, wherein the compound of said composition is compound 43, or a salt thereof.

148. The method according to claim 136, wherein the compound of said composition is compound 44, or a salt thereof.

149. The method according to claim 136, wherein the compound of said composition is compound 45, or a salt thereof.

150. The method according to claim 136, wherein the compound of said composition is compound 46, or a salt thereof.

151. The method according to claim 136, wherein the compound of said composition is compound 47, or a salt thereof.

152. The method according to claim 136, wherein the compound of said composition is compound 48, or a salt thereof.

153. The method according to claim 136, wherein the compound of said composition is compound 49, or a salt thereof.

154. The method according to claim 136, wherein the compound of said composition is compound 50, or a salt thereof.

155. The method according to claim 131, wherein the compound of said composition has the formula

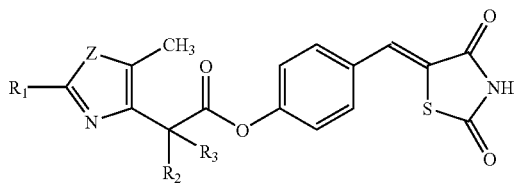

and wherein $R_1$, $R_2$, $R_3$, and Z are defined as:

| Compound number | Z | $R_1$ | $R_2$ | $R_3$ |
|---|---|---|---|---|
| 51 | O | phenyl | H | H; |
| 52 | O | phenyl | $CH_3$ | H; |
| 53 | O | phenyl | $CH_3$ | $CH_3$; |
| 54 | S | phenyl | $CH_3$ | H; |
| 55 | O | 4-F-phenyl | $CH_3$ | H; |
| 56 | S | 4-F-phenyl | $CH_3$ | H; |
| 57 | O | 4-$H_3CO$-phenyl | $CH_3$ | H; |
| 58 | S | 4-$H_3CO$-phenyl | $CH_3$ | H; |
| 59 | O | 3-methylthiophen-2-yl | $CH_3$ | H; |
| 60 | S | 3-methylthiophen-2-yl | $CH_3$ | H; |

-continued

| Compound number | Z | R₁ | R₂ | R₃ |
|---|---|---|---|---|
| 61 | O | H₃C-thiophene | H | H; |
| 62 | O | H₃C-thiophene | CH₃ | H; |
| 63 | S | H₃C-thiophene | H | H; |
| 64 | O | H₃C-isoxazole | CH₃ | H; |
| 65 | S | H₃C-isoxazole | H | H; |
| 66 | O | pyridin-2-yl | CH₃ | H; |
| 67 | O | pyridin-4-yl | CH₃ | H; or |
| 68 | O | pyrazin-2-yl | CH₃ | H; or salts thereof. |

156. The method according to claim 155, wherein the compound of said composition is compound 51, or a salt thereof.

157. The method according to claim 155, wherein the compound of said composition is compound 52, or a salt thereof.

158. The method according to claim 155, wherein the compound of said composition is compound 53, or a salt thereof.

159. The method according to claim 155, wherein the compound of said composition is compound 54, or a salt thereof.

160. The method according to claim 155, wherein the compound of said composition is compound 55, or a salt thereof.

161. The method according to claim 155, wherein the compound of said composition is compound 56, or a salt thereof.

162. The method according to claim 155, wherein the compound of said composition is compound 57, or a salt thereof.

163. The method according to claim 155, wherein the compound of said composition is compound 58, or a salt thereof.

164. The method according to claim 155, wherein the compound of said composition is compound 59, or a salt thereof.

165. The method according to claim 155, wherein the compound of said composition is compound 60, or a salt thereof.

166. The method according to claim 155, wherein the compound of said composition is compound 61, or a salt thereof.

167. The method according to claim 155, wherein the compound of said composition is compound 62, or a salt thereof.

168. The method according to claim 155, wherein the compound of said composition is compound 63, or a salt thereof.

169. The method according to claim 155, wherein the compound of said composition is compound 64, or a salt thereof.

170. The method according to claim 155, wherein the compound of said composition is compound 65, or a salt thereof.

171. The method according to claim 155, wherein the compound of said composition is compound 66, or a salt thereof.

172. The method according to claim 155, wherein the compound of said composition is compound 67, or a salt thereof.

173. The method according to claim 155, wherein the compound of said composition is compound 68, or a salt thereof.

174. The method according to claim 131, wherein the compound of said composition has the formula

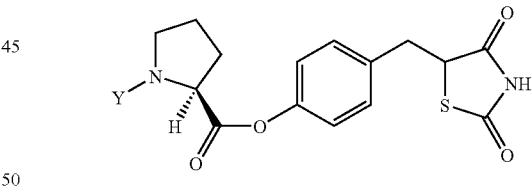

and wherein Y is defined as:

| Compound Number | Y |
|---|---|
| 105 | benzoxazol-2-yl; |
| 106 | benzothiazol-2-yl; |

| Compound Number | Y |
|---|---|
| 107 | pyridin-2-yl |
| 108 | 4,5-dimethylthiazol-2-yl |
| 109 | 2,5,7,8-tetramethyl-6-hydroxychroman-2-yl carbonyl |
| 110 | 2,5,7,8-tetramethyl-6-hydroxychroman-2-yl carbonyl (stereoisomer) |
| 111 | 2,5,7,8-tetramethyl-6-hydroxychroman-2-ylmethyl |
| 112 | 2,5,7,8-tetramethyl-6-hydroxychroman-2-ylmethyl (stereoisomer) |
| 113 | 2,3-dihydro-2,4,6,7-tetramethyl-5-hydroxybenzofuran-3-yl carbonyl; or |
| 114 | 2,3-dihydro-2,4,6,7-tetramethyl-5-hydroxybenzofuran-3-yl carbonyl or salts thereof. |

175. The method according to claim 174, wherein the compound of said composition is compound 105, or a salt thereof.

176. The method according to claim 174, wherein the compound of said composition is compound 106, or a salt thereof.

177. The method according to claim 174, wherein the compound of said composition is compound 107, or a salt thereof.

178. The method according to claim 174, wherein the compound of said composition is compound 108, or a salt thereof.

179. The method according to claim 174, wherein the compound of said composition is compound 109, or a salt thereof.

180. The method according to claim 174, wherein the compound of said composition is compound 110, or a salt thereof.

181. The method according to claim 174, wherein the compound of said composition is compound 111, or a salt thereof.

182. The method according to claim 174, wherein the compound of said composition is compound 112, or a salt thereof.

183. The method according to claim 174, wherein the compound of said composition is compound 113, or a salt thereof.

184. The method according to claim 174, wherein the compound of said composition is compound 114, or a salt thereof.

185. The method according to claim 131, wherein the compound of said composition has the formula

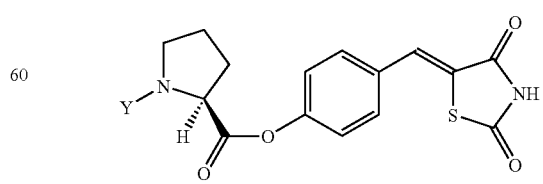

and wherein Y is defined as:

| Compound Number | Y |
|---|---|
| 115 | 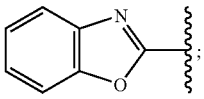 |
| 116 | 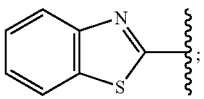 |
| 117 | 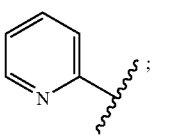 |
| 118 | 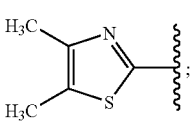 |
| 119 | 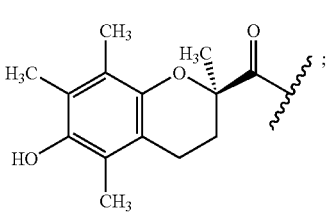 |
| 120 | 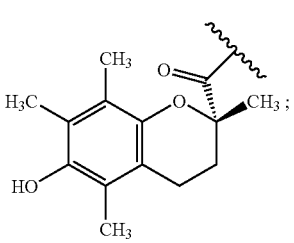 |
| 121 | 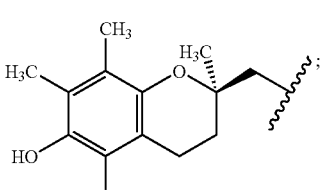 |
| 122 | 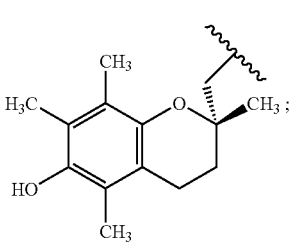 |

-continued

| Compound Number | Y |
|---|---|
| 123 | 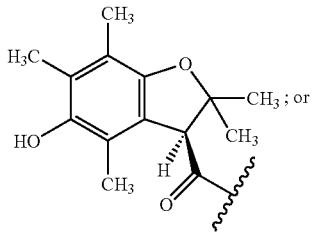 ; or |
| 124 | 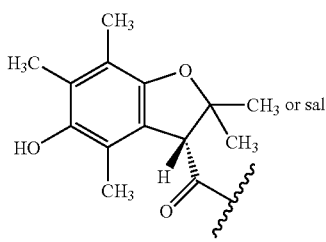 or salts thereof. |

186. The method according to claim 185, wherein the compound of said composition is compound 115, or a salt thereof.

187. The method according to claim 185, wherein the compound of said composition is compound 116, or a salt thereof.

188. The method according to claim 185, wherein the compound of said composition is compound 117, or a salt thereof.

189. The method according to claim 185, wherein the compound of said composition is compound 118, or a salt thereof.

190. The method according to claim 185, wherein the compound of said composition is compound 119, or a salt thereof.

191. The method according to claim 185, wherein the compound of said composition is compound 120, or a salt thereof.

192. The method according to claim 185, wherein the compound of said composition is compound 121, or a salt thereof.

193. The method according to claim 185, wherein the compound of said composition is compound 122, or a salt thereof.

194. The method according to claim 185, wherein the compound of said composition is compound 123, or a salt thereof.

195. The method according to claim 185, wherein the compound of said composition is compound 124, or a salt thereof.

196. The method according to claim 131, wherein the compound of said composition has the formula

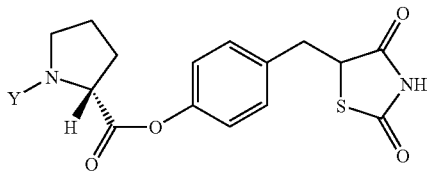

and wherein Y is defined as:

| Compound Number | Y |
|---|---|
| 125 | benzoxazol-2-yl |
| 126 | benzothiazol-2-yl |
| 127 | pyridin-2-yl |
| 128 | 4,5-dimethylthiazol-2-yl |
| 129 | (2,7,8-trimethyl-6-hydroxy-5-methylchroman-2-yl)carbonyl |
| 130 | (2,7,8-trimethyl-6-hydroxy-5-methylchroman-2-yl)carbonyl |
| 131 | 2-(2,7,8-trimethyl-6-hydroxy-5-methylchroman-2-yl)ethyl |
| 132 | 2-(2,7,8-trimethyl-6-hydroxy-5-methylchroman-2-yl)ethyl |
| 133 | (2,3-dihydro-2,7-dimethyl-6-hydroxy-4-methylbenzofuran-3-yl)carbonyl; or |
| 134 | (2,3-dihydro-2,7-dimethyl-6-hydroxy-4-methylbenzofuran-3-yl)carbonyl or salts thereof. |

197. The method according to claim 196, wherein the compound of said composition is compound 125, or a salt thereof.

198. The method according to claim 196, wherein the compound of said composition is compound 126, or a salt thereof.

199. The method according to claim 196, wherein the compound of said composition is compound 127, or a salt thereof.

200. The method according to claim 196, wherein the compound of said composition is compound 128, or a salt thereof.

201. The method according to claim 196, wherein the compound of said composition is compound 129, or a salt thereof.

202. The method according to claim 196, wherein the compound of said composition is compound 130, or a salt thereof.

203. The method according to claim 196, wherein the compound of said composition is compound 131, or a salt thereof.

204. The method according to claim 196, wherein the compound of said composition is compound 132, or a salt thereof.

205. The method according to claim 196, wherein the compound of said composition is compound 133, or a salt thereof.

206. The method according to claim 196, wherein the compound of said composition is compound 134, or a salt thereof.

207. The method according to claim 131, wherein the compound of said composition has the formula

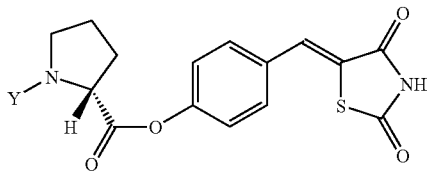

and wherein Y is defined as:

| Compound Number | Y |
|---|---|
| 135 | benzoxazol-2-yl |
| 136 | benzothiazol-2-yl |
| 137 | pyridin-2-yl |
| 138 | 4,5-dimethylthiazol-2-yl |
| 139 | (2-methyl-5,7,8-trimethyl-6-hydroxychroman-2-yl)carbonyl |
| 140 | (2-methyl-5,7,8-trimethyl-6-hydroxychroman-2-yl)carbonyl |
| 141 | 2-(2-methyl-5,7,8-trimethyl-6-hydroxychroman-2-yl)ethyl |
| 142 | 2-(2-methyl-5,7,8-trimethyl-6-hydroxychroman-2-yl)ethyl |
| 143 | (2,2-dimethyl-4,6,7-trimethyl-5-hydroxy-2,3-dihydrobenzofuran-3-yl)carbonyl; or |
| 144 | (2,2-dimethyl-4,6,7-trimethyl-5-hydroxy-2,3-dihydrobenzofuran-3-yl)carbonyl or salts thereof. |

208. The method according to claim 207, wherein the compound of said composition is compound 135, or a salt thereof.

209. The method according to claim 207, wherein the compound of said composition is compound 136, or a salt thereof.

210. The method according to claim 207, wherein the compound of said composition is compound 137, or a salt thereof.

211. The method according to claim 207, wherein the compound of said composition is compound 138, or a salt thereof.

212. The method according to claim 207, wherein the compound of said composition is compound 139, or a salt thereof.

213. The method according to claim 207, wherein the compound of said composition is compound 140, or a salt thereof.

214. The method according to claim 207, wherein the compound of said composition is compound 141, or a salt thereof.

215. The method according to claim 207, wherein the compound of said composition is compound 142, or a salt thereof.

216. The method according to claim 207, wherein the compound of said composition is compound 143, or a salt thereof.

217. The method according to claim 207, wherein the compound of said composition is compound 144, or a salt thereof.

218. The method according to claim 131, wherein the compound of said composition has the formula

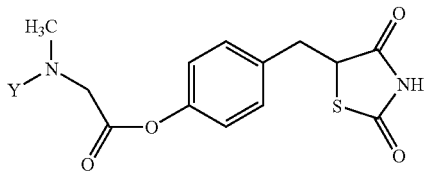

and wherein Y is defined as:

| Compound number | Y |
|---|---|
| 185 | benzoxazol-2-yl |
| 186 | benzothiazol-2-yl |
| 187 | pyridin-2-yl |
| 188 | 4,5-dimethylthiazol-2-yl |
| 189 | (2-methyl-6-hydroxy-5,7,8-trimethylchroman-2-yl)carbonyl |
| 190 | (2-methyl-6-hydroxy-5,7,8-trimethylchroman-2-yl)carbonyl |
| 191 | 2-(2-methyl-6-hydroxy-5,7,8-trimethylchroman-2-yl)ethyl |

-continued

| Compound number | Y |
|---|---|
| 192 | 2,2-dimethyl-6-hydroxy-5,7,8-trimethylchroman-2-ylmethyl |
| 193 | (2,2-dimethyl-6-hydroxy-4,7-dimethylbenzofuran-3-yl)carbonyl; or |
| 194 | (2,2-dimethyl-6-hydroxy-4,7-dimethylbenzofuran-3-yl)carbonyl or salts thereof. |

219. The method according to claim 218, wherein the compound of said composition is compound 185, or a salt thereof.

220. The method according to claim 218, wherein the compound of said composition is compound 186, or a salt thereof.

221. The method according to claim 218, wherein the compound of said composition is compound 187, or a salt thereof.

222. The method according to claim 218, wherein the compound of said composition is compound 188, or a salt thereof.

223. The method according to claim 218, wherein the compound of said composition is compound 189, or a salt thereof.

224. The method according to claim 218, wherein the compound of said composition is compound 190, or a salt thereof.

225. The method according to claim 218, wherein the compound of said composition is compound 191, or a salt thereof.

226. The method according to claim 218, wherein the compound of said composition is compound 192, or a salt thereof.

227. The method according to claim 218, wherein the compound of said composition is compound 193, or a salt thereof.

228. The method according to claim 218, wherein the compound of said composition is compound 194, or a salt thereof.

229. The method according to claim 131, wherein the compound of said composition has the formula

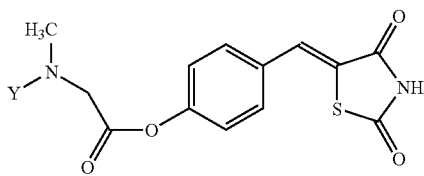

and wherein Y is defined as:

| Compound number | Y |
|---|---|
| 195 | benzoxazol-2-yl |
| 196 | benzothiazol-2-yl |
| 197 | pyridin-2-yl |
| 198 | 4,5-dimethylthiazol-2-yl |
| 199 | (2-methyl-6-hydroxy-5,7,8-trimethylchroman-2-yl)carbonyl |
| 200 | (2-methyl-6-hydroxy-5,7,8-trimethylchroman-2-yl)carbonyl |
| 201 | 2-ethyl-6-hydroxy-2,5,7,8-tetramethylchroman-2-ylmethyl |
| 202 | 2,2-dimethyl-6-hydroxy-5,7,8-trimethylchroman-2-ylmethyl |
| 203 | (2,3-dimethyl-6-hydroxy-4,7-dimethyl-2,3-dihydrobenzofuran-3-yl)carbonyl |
| 204 | (2,3-dimethyl-6-hydroxy-4,7-dimethyl-2,3-dihydrobenzofuran-3-yl)carbonyl or salts thereof. |

230. The method according to claim 229, wherein the compound of said composition is compound 195, or a salt thereof.

231. The method according to claim 229, wherein the compound of said composition is compound 196, or a salt thereof.

232. The method according to claim 229, wherein the compound of said compound is compound 197, or a salt thereof.

233. The method according to claim 229, wherein the compound of said composition is compound 198, or a salt thereof.

234. The method according to claim 229, wherein the compound of said composition is compound 199, or a salt thereof.

235. The method according to claim 229, wherein the compound of said composition is compound 200, or a salt thereof.

236. The method according to claim 229, wherein the compound of said composition is compound 201, or a salt thereof.

237. The method according to claim 229, wherein the compound of said composition is compound 202, or a salt thereof.

238. The method according to claim 229, wherein the compound of said composition is compound 203, or a salt thereof.

239. The method according to claim 229, wherein the compound of said composition is compound 204, or a salt thereof.

240. The method according to claim 131, wherein the compound of said composition has the formula

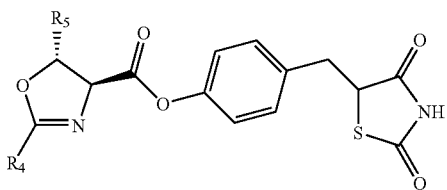

and wherein R$_4$ and R$_5$ are defined as:

| Compound number | R$_4$ | R$_5$ |
|---|---|---|
| 225 | phenyl | H; |
| 226 | phenyl | CH$_3$; |
| 227 | 4-F-phenyl | H; |
| 228 | 4-F-phenyl | CH$_3$; |
| 229 | 4-H$_3$CO-phenyl | H; |
| 230 | 4-H$_3$CO-phenyl | CH$_3$; |
| 231 | 3-methylthien-2-yl | H; |
| 232 | 3-methylthien-2-yl | CH$_3$; |
| 233 | 5-methylthien-2-yl | H; |
| 234 | 5-methylthien-2-yl | CH$_3$; |
| 235 | 5-methylisoxazol-3-yl | H; |
| 236 | 5-methylisoxazol-3-yl | CH$_3$; |
| 237 | pyridin-2-yl | H; |
| 238 | pyridin-2-yl | CH$_3$; |
| 239 | pyridin-4-yl | H; |
| 240 | pyridin-4-yl | CH$_3$; |
| 241 | pyrazin-2-yl | H; or |
| 242 | pyrazin-2-yl | CH$_3$; or salts thereof. |

241. The method according to claim 240, wherein the compound of said composition is compound 225, or a salt thereof.

242. The method according to claim 240, wherein the compound of said composition is compound 226, or a salt thereof.

243. The method according to claim 240, wherein the compound of said composition is compound 227, or a salt thereof.

244. The method according to claim 240, wherein the compound of said composition is compound 228, or a salt thereof.

245. The method according to claim 240, wherein the compound of said composition is compound 229, or a salt thereof.

246. The method according to claim 240, wherein the compound of said composition is compound 230, or a salt thereof.

247. The method according to claim 240, wherein the compound of said composition is compound 231, or a salt thereof.

248. The method according to claim 240, wherein the compound of said composition is compound 232, or a salt thereof.

249. The method according to claim 240, wherein the compound of said composition is compound 233, or a salt thereof.

250. The method according to claim 240, wherein the compound of said composition is compound 234, or a salt thereof.

251. The method according to claim 240, wherein the compound of said composition is compound 235, or a salt thereof.

252. The method according to claim 240, wherein the compound of said composition is compound 236, or a salt thereof.

253. The method according to claim 240, wherein the compound of said composition is compound 237, or a salt thereof.

254. The method according to claim 240, wherein the compound of said composition is compound 238, or a salt thereof.

255. The method according to claim 240, wherein the compound of said composition is compound 239, or a salt thereof.

256. The method according to claim 240, wherein the compound of said composition is compound 240, or a salt thereof.

257. The method according to claim 240, wherein the compound of said composition is compound 241, or a salt thereof.

258. The method according to claim 240, wherein the compound of said composition is compound 242, or a salt thereof.

259. The method according to claim 131, wherein:
A is NH and B is sulfur;
$D_1$–$D_6$ are C;
E can be attached to one or more of the atoms located at $D_2$, $D_3$, $D_5$ or $D_6$;
P and Q are a double bond;
E can be the same or different and is a moiety selected from the group consisting of H, $C_{1-10}$ alkyl, and substituted alkyl groups; and
X is a substituted carboxylic group comprising —N—(C)$_{1-3}$—C(O)O— that is attached to $D_1$;
or salts of the compound of Formula I.

260. The method according to claim 131, wherein:
A is NH and B is sulfur;
$D_1$–$D_6$ are C;
E can be attached to one or more of the atoms located at $D_2$, $D_3$, $D_5$ or $D_6$;
P and Q are hydrogen;
E is hydrogen; and
X is a substituted carboxylic group comprising —N—(C)$_{1-3}$—C(O)O— that is attached to $D_1$;
or salts of the compound of Formula I.

* * * * *